United States Patent
Saitou et al.

(10) Patent No.: US 10,563,171 B2
(45) Date of Patent: Feb. 18, 2020

(54) METHOD FOR INDUCING DIFFERENTIATION OF PLURIPOTENT STEM CELLS INTO GERM CELLS

(71) Applicant: Kyoto University, Kyoto-shi, Kyoto (JP)

(72) Inventors: Mitinori Saitou, Kyoto (JP); Kotaro Sasaki, Kyoto (JP); Shihori Yokobayashi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/740,454

(22) PCT Filed: Jun. 29, 2016

(86) PCT No.: PCT/JP2016/069360
§ 371 (c)(1),
(2) Date: Dec. 28, 2017

(87) PCT Pub. No.: WO2017/002888
PCT Pub. Date: Jan. 5, 2017

(65) Prior Publication Data
US 2018/0187147 A1     Jul. 5, 2018

(30) Foreign Application Priority Data

Jun. 29, 2015   (JP) ................................. 2015-130501

(51) Int. Cl.
*C12N 5/0735* (2010.01)
*G01N 33/569* (2006.01)

(52) U.S. Cl.
CPC ..... *C12N 5/0611* (2013.01); *G01N 33/56966* (2013.01); *C12N 2500/90* (2013.01); *C12N 2500/98* (2013.01); *C12N 2501/11* (2013.01); *C12N 2501/15* (2013.01); *C12N 2501/155* (2013.01); *C12N 2501/20* (2013.01); *C12N 2501/999* (2013.01); *C12N 2506/03* (2013.01); *G01N 2333/705* (2013.01); *G01N 2333/70546* (2013.01)

(58) Field of Classification Search
None
See application file for complete search history.

(56) References Cited

U.S. PATENT DOCUMENTS

| | | | |
|---|---|---|---|
| 2013/0122536 A1 | 5/2013 | Osafune et al. | |
| 2013/0143321 A1 | 6/2013 | Saitou et al. | |
| 2014/0315301 A1 | 10/2014 | Hanna et al. | |

FOREIGN PATENT DOCUMENTS

| | | |
|---|---|---|
| JP | 2013-530680 A | 8/2013 |
| JP | 2013-538038 A | 10/2013 |
| WO | WO 2014/174470 A1 | 10/2014 |

OTHER PUBLICATIONS

Brons et al., "Derivation of pluripotent epiblast stem cells from mammalian embryos," *Nature*, 448: 191-195 (2007).
Hayashi et al., "Reconstitution of the Mouse Germ Cell Specification Pathway in Culture by Pluripotent Stem Cells," *Cell*, 146(4): 519-532 (2011).
Hayashi et al., "Germline development from human pluripotent stem cells toward disease modeling of infertility," *Fertility and Sterility*, 97(6): 1250-1259 (2012).
Hayashi et al., "Offspring from Oocytes Derived from in Vitro Primordial Germ Cell-like Cells in Mice," *Science*, 338(6109): 971-975 (2012).
Irie et al., "SOX17 Is a Critical Specifier of Human Primordial Germ Cell Fate," *Cell*, 160(1-2): 253-268 (2015).
Park et al., "Preliminary Evaluation of PGC Differentiation Protocol in Rhesus Model," *Fertility and Sterility*, 102(3 Suppl.): e103, Abstract No. O-303 (2014).
Sugawa et al., "Human primordial germ cell commitment in vitro associates with a unique PRDM14 expression profile," *EMBO J.*, 34(8): 1009-1024 (2015).
Takahashi et al., "Induction of Pluripotent Stem Cells from Adult Human Fibroblasts by Defined Factors," *Cell*, 131(5): 861-872 (2007).
Tesar et al., "New cell lines from mouse epiblast share defining features with human embryonic stem cells," *Nature*, 448: 196-199 (2007).
Thomson et al., "Embryonic Stem Cell Lines Derived from Human Blastocysts," *Science*, 282(5391): 1145-1147 (1998).
Ying et al., "The ground state of embryonic stem cell self-renewal," *Nature*, 453(7184): 519-523 (2008).
Japanese Patent Office, International Search Report in International Patent Application No. PCT/JP2016/069360 (dated Sep. 27, 2016).

*Primary Examiner* — Daniel C Gamett
(74) *Attorney, Agent, or Firm* — Leydig, Voit & Mayer, Ltd.

(57) ABSTRACT

The invention provides a method for inducing human primordial germ cell-like (PGC-like) cells from human pluripotent stem cells, with high efficiency and high reproducibility, and a cell surface marker for identifying human PGC-like cells. In particular, the invention provides a method for producing a human PGC-like cell from a human pluripotent stem cell, includes a step of producing a mesoderm-like cell by culturing a human pluripotent stem cell in a culture medium comprising activin A and a GSK3β inhibitor, and a step of culturing the mesoderm-like cell in a culture medium containing BMP. The invention also provides a method for producing an isolated human PGC-like cell, which includes the aforementioned two steps and the additional step of selecting a cell positive to at least one cell surface marker selected from the group consisting of PECAM (CD31), INTEGRINα6 (CD49f), INTEGRINβ3 (CD61), KIT (CD117), EpCAM, PODOPLANIN and TRA1-81.

20 Claims, 14 Drawing Sheets

Specification includes a Sequence Listing.

SEQUENCE LISTING

<160> NUMBER OF SEQ ID NOS: 111

<210> SEQ ID NO 1
<211> LENGTH: 22
<212> TYPE: DNA
<213> ORGANISM: Artificial Sequence
<220> FEATURE:
<223> OTHER INFORMATION: Synthetic sequence - BLIMP1 Forward primer

<400> SEQUENCE: 1
aaaccaaagc atcacgttga ca                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence - BLIMP1 Reverse primer

<400> SEQUENCE: 2
ggatggatgg tgagagaagc aa                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence - TFAP2C Forward primer

<400> SEQUENCE: 3
attaagagga tgctgggctc tg                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence - TFAP2C Reverse primer

<400> SEQUENCE: 4
cactgtactg cacactcacc tt                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic sequence - NANOS3 Forward primer

<400> SEQUENCE: 5
tggcaaggga agagctgaaa tc                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic sequence - NANOS3 Reverse primer

<400> SEQUENCE: 6
ttattgaggg ctgactggat gc                                              22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic sequence - DAZL Forward primer

<400> SEQUENCE: 7
tggcccttct ttcagtgact tc                                              22

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence - DAZL Reverse primer

<400> SEQUENCE: 8
gaccctaggg ggcactagta a                                               21

<210> SEQ ID NO 9
<211> LENGTH: 22
<212> TYPE: DNA
<213> ORGANISM: Artificial Sequence
<220> FEATURE:
<223> OTHER INFORMATION: Synthetic sequence - DPPA3 Forward primer

<400> SEQUENCE: 9
aagcccaaag tcagtgagat ga                                              22

<210> SEQ ID NO 10
<211> LENGTH: 23
<212> TYPE: DNA
<213> ORGANISM: Artificial Sequence
<220> FEATURE:
<223> OTHER INFORMATION: Synthetic sequence - DPPA3 Reverse primer

<400> SEQUENCE: 10
gctatagccc aactacctaa tgc                                             23

<210> SEQ ID NO 11
<211> LENGTH: 22
<212> TYPE: DNA
<213> ORGANISM: Artificial Sequence
<220> FEATURE:
<223> OTHER INFORMATION: Synthetic sequence - DDX4 Forward primer

<400> SEQUENCE: 11
ttcttcacaa gctcccaatc ca                                              22

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence - DDX4 Reverse primer

<400> SEQUENCE: 12
ttcttctctg catcaaaacc aca                                             23

<210> SEQ ID NO 13
<211> LENGTH: 23
<212> TYPE: DNA
<213> ORGANISM: Artificial Sequence
<220> FEATURE:
<223> OTHER INFORMATION: Synthetic sequence - ZFP42 Forward primer

<400> SEQUENCE: 13
ccagactgga taacagcaag agc                                             23
```

<210> SEQ ID NO 14
<211> LENGTH: 24
<212> TYPE: DNA
<213> ORGANISM: Artificial Sequence
<220> FEATURE:
<223> OTHER INFORMATION: Synthetic sequence - ZFP42 Reverse primer

<400> SEQUENCE: 14 tgcaaattt tcattctcta gggc                                    24

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence - PRDM14 Forward primer

<400> SEQUENCE: 15
tatcatactg tgcacttggc agaa                                   24

<210> SEQ ID NO 16
<211> LENGTH: 23
<212> TYPE: DNA
<213> ORGANISM: Artificial Sequence
<220> FEATURE:
<223> OTHER INFORMATION: Synthetic sequence - PRDM14 Reverse primer

<400> SEQUENCE: 16
agcaactggg actacaggtt tgt                                    23

<210> SEQ ID NO 17
<211> LENGTH: 22
<212> TYPE: DNA
<213> ORGANISM: Artificial Sequence
<220> FEATURE:
<223> OTHER INFORMATION: Synthetic sequence - KLF2 Forward primer

<400> SEQUENCE: 17
actagaggat cgaggcttgt ga                                     22

<210> SEQ ID NO 18
<211> LENGTH: 22
<212> TYPE: DNA
<213> ORGANISM: Artificial Sequence
<220> FEATURE:
<223> OTHER INFORMATION: Synthetic sequence - KLF2 Reverse primer

<400> SEQUENCE: 18
tgcccacctg tctctctatg ta                                     22

<210> SEQ ID NO 19
<211> LENGTH: 22
<212> TYPE: DNA
<213> ORGANISM: Artificial Sequence
<220> FEATURE:
<223> OTHER INFORMATION: Synthetic sequence - KLF4 Forward primer

<400> SEQUENCE: 19
agcctaaatg atggtgcttg gt                                     22

<210> SEQ ID NO 20
<211> LENGTH: 22
<212> TYPE: DNA
<213> ORGANISM: Artificial Sequence
<220> FEATURE:
<223> OTHER INFORMATION: Synthetic sequence - KLF4 Reverse primer

```
<400> SEQUENCE: 20
ccttgtcaaa gtatgcagca gt                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic sequence - TCL1B Forward primer

<400> SEQUENCE: 21 caaatccect tcatacccac ca                                              22

<210> SEQ ID NO 22
<211> LENGTH: 22
<212> TYPE: DNA
<213> ORGANISM: Artificial Sequence
<220> FEATURE:
<223> OTHER INFORMATION: Synthetic sequence - TCL1B Reverse primer

<400> SEQUENCE: 22
tgccatctct taaaccgaac ca                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic sequence - TFCP2L1 Forward primer

<400> SEQUENCE: 23
agctcaaagt tgtcctactg cc                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic sequence - TFCP2L1 Reverse primer

<400> SEQUENCE: 24
ttctaaccca agcacagatc cc                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic sequence - ESRRB Forward primer

<400> SEQUENCE: 25
taaaatggca gttccccatt gc                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic sequence - ESRRB Reverse primer

<400> SEQUENCE: 26
ccagatacat gggaccagga tg                                              22

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic sequence - POU5F1 Forward primer

<400> SEQUENCE: 27
ctgtctccgt caccactctg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic sequence - POU5F1 Reverse primer

<400> SEQUENCE: 28
aaaccctggc acaaactcca                                              20

<210> SEQ ID NO 29
<211> LENGTH: 22
<212> TYPE: DNA
<213> ORGANISM: Artificial Sequence
<220> FEATURE:
<223> OTHER INFORMATION: Synthetic sequence - NANOG Forward primer

<400> SEQUENCE: 29
agaggtctcg tatttgctgc at                                           22

<210> SEQ ID NO 30
<211> LENGTH: 22
<212> TYPE: DNA
<213> ORGANISM: Artificial Sequence
<220> FEATURE:
<223> OTHER INFORMATION: Synthetic sequence - NANOG Reverse primer

<400> SEQUENCE: 30
aaacactcgg tgaaatcagg gt                                           22

<210> SEQ ID NO 31
<211> LENGTH: 22
<212> TYPE: DNA
<213> ORGANISM: Artificial Sequence
<220> FEATURE:
<223> OTHER INFORMATION: Synthetic sequence - SOX2 Forward primer

<400> SEQUENCE: 31
tgaatcagtc tgccgagaat cc                                           22

<210> SEQ ID NO 32
<211> LENGTH: 23
<212> TYPE: DNA
<213> ORGANISM: Artificial Sequence
<220> FEATURE:
<223> OTHER INFORMATION: Synthetic sequence - SOX2  Reverse primer

<400> SEQUENCE: 32
tctcaaactg tgcataatgg agt                                          23

<210> SEQ ID NO 33
<211> LENGTH: 22
<212> TYPE: DNA
<213> ORGANISM: Artificial Sequence
<220> FEATURE:
<223> OTHER INFORMATION: Synthetic sequence - SOX15  Forward primer

<400> SEQUENCE: 33
```
ttttaatcca gcagcatccc ct                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic sequence - SOX15 Reverse primer

<400> SEQUENCE: 34
aattgtatgt tgtgcggctc tc                                              22

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence - SOX17 Forward primer

<400> SEQUENCE: 35
ttcgtgtgca agcctgagat                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic sequence - SOX17 Reverse primer

<400> SEQUENCE: 36
taatataccg cggagctggc                                                 20

<210> SEQ ID NO 37
<211> LENGTH: 22
<212> TYPE: DNA
<213> ORGANISM: Artificial Sequence
<220> FEATURE:
<223> OTHER INFORMATION: Synthetic sequence - GATA4 Forward primer

<400> SEQUENCE: 37
cctctttctc agcagagctg ta                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic sequence - GATA4 Reverse primer

<400> SEQUENCE: 38
ctctgctaca gccagtagga tt                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic sequence - GATA6 Forward primer

<400> SEQUENCE: 39
acagggcgat ttcctttcag tt                                              22

<210> SEQ ID NO 40
<211> LENGTH: 22
<212> TYPE: DNA

```
<213> ORGANISM: Artificial Sequence
<220> FEATURE:
<223> OTHER INFORMATION: Synthetic sequence - GATA6  Reverse primer

<400> SEQUENCE: 40
cttctgttgg gggtaacgtc tg                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic sequence - FOXA2  Forward primer

<400> SEQUENCE: 41
acccggtttt atcccttgaa tc                                              22

<210> SEQ ID NO 42
<211> LENGTH: 22
<212> TYPE: DNA
<213> ORGANISM: Artificial Sequence
<220> FEATURE:
<223> OTHER INFORMATION: Synthetic sequence - FOXA2  Reverse primer

<400> SEQUENCE: 42
atacaacctg caaccagaca gg                                              22

<210> SEQ ID NO 43
<211> LENGTH: 22
<212> TYPE: DNA
<213> ORGANISM: Artificial Sequence
<220> FEATURE:
<223> OTHER INFORMATION: Synthetic sequence - MIXL1 Forward primer

<400> SEQUENCE: 43
tgctttcaaa acactcgagg ac                                              22

<210> SEQ ID NO 44
<211> LENGTH: 22
<212> TYPE: DNA
<213> ORGANISM: Artificial Sequence
<220> FEATURE:
<223> OTHER INFORMATION: Synthetic sequence - MIXL1 Reverse primer

<400> SEQUENCE: 44
gagtgatcga agtaacaggt gc                                              22

<210> SEQ ID NO 45
<211> LENGTH: 22
<212> TYPE: DNA
<213> ORGANISM: Artificial Sequence
<220> FEATURE:
<223> OTHER INFORMATION: Synthetic sequence - SP5 Forward primer

<400> SEQUENCE: 45
gagatttgaa acagtgctcg gg                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic sequence - SP5  Reverse primer

<400> SEQUENCE: 46
ggagctgaag acaaaagcaa ca                                              22
```

```
<210> SEQ ID NO 47
<211> LENGTH: 22
<212> TYPE: DNA
<213> ORGANISM: Artificial Sequence
<220> FEATURE:
<223> OTHER INFORMATION: Synthetic sequence - EOMES  Forward primer

<400> SEQUENCE: 47 aagggagag tttcatcatc cc                                               22

<210> SEQ ID NO 48
<211> LENGTH: 23
<212> TYPE: DNA
<213> ORGANISM: Artificial Sequence
<220> FEATURE:
<223> OTHER INFORMATION: Synthetic sequence - EOMES  Reverse primer

<400> SEQUENCE: 48
ggcgcaagaa gaggatgaaa tag                                             23

<210> SEQ ID NO 49
<211> LENGTH: 22
<212> TYPE: DNA
<213> ORGANISM: Artificial Sequence
<220> FEATURE:
<223> OTHER INFORMATION: Synthetic sequence - NODAL  Forward primer

<400> SEQUENCE: 49
cattgcctca ggctgggttg gt                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic sequence - NODAL  Reverse primer

<400> SEQUENCE: 50
acagctcatt agcagagaac ca                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic sequence - T  Forward primer

<400> SEQUENCE: 51
agccaaagac aatcagcaga aa                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic sequence - T Reverse primer

<400> SEQUENCE: 52
cacaaaagga ggggcttcac ta                                              22

<210> SEQ ID NO 53
<211> LENGTH: 22
<212> TYPE: DNA
<213> ORGANISM: Artificial Sequence
<220> FEATURE:
```

<223> OTHER INFORMATION: Synthetic sequence - EVX1 Forward primer

<400> SEQUENCE: 53
caaatcctca ctcccacact ca                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic sequence - EVX1 Reverse primer

<400> SEQUENCE: 54
gaagaaccac tccctctcag tc                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic sequence - GSC Forward primer

<400> SEQUENCE: 55
gtcgagaaag aggaacgagg ag                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic sequence - GSC Reverse primer

<400> SEQUENCE: 56
aaatactacg gtgggggcta gt                                              22

<210> SEQ ID NO 57
<211> LENGTH: 22
<212> TYPE: DNA
<213> ORGANISM: Artificial Sequence
<220> FEATURE:
<223> OTHER INFORMATION: Synthetic sequence - MSX2 Forward primer

<400> SEQUENCE: 57
ggcagaaggt aaagccatgt tt                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetic sequence - MSX2 Reverse primer

<400> SEQUENCE: 58
taaaggtata ccggagggag gg                                              22

<210> SEQ ID NO 59
<211> LENGTH: 23
<212> TYPE: DNA
<213> ORGANISM: Artificial Sequence
<220> FEATURE:
<223> OTHER INFORMATION: Synthetic sequence - PAX6 Forward primer

<400> SEQUENCE: 59
gcgggtgaca aaatagttgt ctt                                             23

```
<210> SEQ ID NO 60
<211> LENGTH: 22
<212> TYPE: DNA
<213> ORGANISM: Artificial Sequence
<220> FEATURE:
<223> OTHER INFORMATION: Synthetic sequence - PAX6 Reverse primer

<400> SEQUENCE: 60
gccaggatgt caaatctctc ca                                              22

<210> SEQ ID NO 61
<211> LENGTH: 22
<212> TYPE: DNA
<213> ORGANISM: Artificial Sequence
<220> FEATURE:
<223> OTHER INFORMATION: Synthetic sequence - SOX1 Forward primer

<400> SEQUENCE: 61
ggccaaggta acactcatcg ta                                              22

<210> SEQ ID NO 62
<211> LENGTH: 22
<212> TYPE: DNA
<213> ORGANISM: Artificial Sequence
<220> FEATURE:
<223> OTHER INFORMATION: Synthetic sequence - SOX1 Reverse primer

<400> SEQUENCE: 62
accctgtgat ttgggaagtg aa                                              22

<210> SEQ ID NO 63
<211> LENGTH: 22
<212> TYPE: DNA
<213> ORGANISM: Artificial Sequence
<220> FEATURE:
<223> OTHER INFORMATION: Synthetic sequence - DNMT3A Forward primer

<400> SEQUENCE: 63
tgggattcat ccagactcat gc                                              22

<210> SEQ ID NO 64
<211> LENGTH: 22
<212> TYPE: DNA
<213> ORGANISM: Artificial Sequence
<220> FEATURE:
<223> OTHER INFORMATION: Synthetic sequence - DNMT3A  Reverse primer

<400> SEQUENCE: 64
aaagtgagaa actgggcctg aa                                              22

<210> SEQ ID NO 65
<211> LENGTH: 21
<212> TYPE: DNA
<213> ORGANISM: Artificial Sequence
<220> FEATURE:
<223> OTHER INFORMATION: Synthetic sequence - DNMT3B Forward primer

<400> SEQUENCE: 65
taactggagc cacgacgtaa c                                               21

<210> SEQ ID NO 66
<211> LENGTH: 22
<212> TYPE: DNA
<213> ORGANISM: Artificial Sequence
<220> FEATURE:
<223> OTHER INFORMATION: Synthetic sequence - DNMT3B Reverse primer
```

```
<400> SEQUENCE: 66
gcatccgtca tctttcagcc ta                                              22

<210> SEQ ID NO 67
<211> LENGTH: 20
<212> TYPE: DNA
<213> ORGANISM: Artificial Sequence
<220> FEATURE:
<223> OTHER INFORMATION: Synthetic sequence - DNMT3L Forward primer

<400> SEQUENCE: 67
agccataagg agcaggcact                                                 20

<210> SEQ ID NO 68
<211> LENGTH: 23
<212> TYPE: DNA
<213> ORGANISM: Artificial Sequence
<220> FEATURE:
<223> OTHER INFORMATION: Synthetic sequence - DNMT3L Reverse primer

<400> SEQUENCE: 68
ggggagaaag cagttcttca cca                                             23

<210> SEQ ID NO 69
<211> LENGTH: 22
<212> TYPE: DNA
<213> ORGANISM: Artificial Sequence
<220> FEATURE:
<223> OTHER INFORMATION: Synthetic sequence - HOXD1 Forward primer

<400> SEQUENCE: 69
agctgcttca gtgatcttca ca                                              22

<210> SEQ ID NO 70
<211> LENGTH: 22
<212> TYPE: DNA
<213> ORGANISM: Artificial Sequence
<220> FEATURE:
<223> OTHER INFORMATION: Synthetic sequence - HOXD1 Reverse primer

<400> SEQUENCE: 70
acccattctg tggatttgtt ca                                              22

<210> SEQ ID NO 71
<211> LENGTH: 22
<212> TYPE: DNA
<213> ORGANISM: Artificial Sequence
<220> FEATURE:
<223> OTHER INFORMATION: Synthetic sequence - PPIA Forward primer

<400> SEQUENCE: 71
ttgatcattt ggtgtgttgg gc                                              22

<210> SEQ ID NO 72
<211> LENGTH: 22
<212> TYPE: DNA
<213> ORGANISM: Artificial Sequence
<220> FEATURE:
<223> OTHER INFORMATION: Synthetic sequence - PPIA Reverse primer

<400> SEQUENCE: 72
aagactgaga tgcacaagtg gt                                              22

<210> SEQ ID NO 73
<211> LENGTH: 22
```

```
<212> TYPE: DNA
<213> ORGANISM: Artificial Sequence
<220> FEATURE:
<223> OTHER INFORMATION: Synthetic sequence - ARBP Forward primer

<400> SEQUENCE: 73
gaaactctgc attctcgctt cc                                              22

<210> SEQ ID NO 74
<211> LENGTH: 22
<212> TYPE: DNA
<213> ORGANISM: Artificial Sequence
<220> FEATURE:
<223> OTHER INFORMATION: Synthetic sequence - ARBP Reverse primer

<400> SEQUENCE: 74
actcgtttgt acccgttgat ga                                              22

<210> SEQ ID NO 75
<211> LENGTH: 23
<212> TYPE: DNA
<213> ORGANISM: Artificial Sequence
<220> FEATURE:
<223> OTHER INFORMATION: Synthetic sequence - ERCC 1806 Forward primer

<400> SEQUENCE: 75
gatcccggaa gatacgctct aag                                             23

<210> SEQ ID NO 76
<211> LENGTH: 23
<212> TYPE: DNA
<213> ORGANISM: Artificial Sequence
<220> FEATURE:
<223> OTHER INFORMATION: Synthetic sequence - ERCC 1806 Reverse primer

<400> SEQUENCE: 76
cgcaggttga tgcttccaat aaa                                             23

<210> SEQ ID NO 77
<211> LENGTH: 23
<212> TYPE: DNA
<213> ORGANISM: Artificial Sequence
<220> FEATURE:
<223> OTHER INFORMATION: Synthetic sequence - ERCC 451.5 Forward primer

<400> SEQUENCE: 77
caggcaagag ttcaatcgct tag                                             23

<210> SEQ ID NO 78
<211> LENGTH: 23
<212> TYPE: DNA
<213> ORGANISM: Artificial Sequence
<220> FEATURE:
<223> OTHER INFORMATION: Synthetic sequence - ERCC 451.5 Reverse primer

<400> SEQUENCE: 78
tagccttcag tgactgtgag atg                                             23

<210> SEQ ID NO 79
<211> LENGTH: 22
<212> TYPE: DNA
<213> ORGANISM: Artificial Sequence
<220> FEATURE:
<223> OTHER INFORMATION: Synthetic sequence - ERCC 56.4 Forward primer

<400> SEQUENCE: 79
```

```
ccaaccccac attgtaactt cg                                              22
```

<210> SEQ ID NO 80
<211> LENGTH: 22
<212> TYPE: DNA
<213> ORGANISM: Artificial Sequence
<220> FEATURE:
<223> OTHER INFORMATION: Synthetic sequence - ERCC 56.4 Reverse primer

<400> SEQUENCE: 80

```
gtctttactt acgcgctcct ct                                              22
```

<210> SEQ ID NO 81
<211> LENGTH: 25
<212> TYPE: DNA
<213> ORGANISM: Artificial Sequence
<220> FEATURE:
<223> OTHER INFORMATION: Synthetic sequence - monkey BLIMP1 Forward
      primer

<400> SEQUENCE: 81

```
ttcccaacta ctcgtttgtt ctttg                                           25
```

<210> SEQ ID NO 82
<211> LENGTH: 25
<212> TYPE: DNA
<213> ORGANISM: Artificial Sequence
<220> FEATURE:
<223> OTHER INFORMATION: Synthetic sequence - monkey BLIMP1 Reverse
      primer

<400> SEQUENCE: 82

```
catgtaagag gcagaaaaag gaagg                                           25
```

<210> SEQ ID NO 83
<211> LENGTH: 20
<212> TYPE: DNA
<213> ORGANISM: Artificial Sequence
<220> FEATURE:
<223> OTHER INFORMATION: Synthetic sequence - monkey TFAP2C Forward
      primer

<400> SEQUENCE: 83

```
tcggagatca agtcctctgg                                                 20
```

<210> SEQ ID NO 84
<211> LENGTH: 20
<212> TYPE: DNA
<213> ORGANISM: Artificial Sequence
<220> FEATURE:
<223> OTHER INFORMATION: Synthetic sequence - monkey TFAP2C Reverse
      primer

<400> SEQUENCE: 84

```
cctttgaaca cggggtttag                                                 20
```

<210> SEQ ID NO 85
<211> LENGTH: 22
<212> TYPE: DNA
<213> ORGANISM: Artificial Sequence
<220> FEATURE:
<223> OTHER INFORMATION: Synthetic sequence - monkey PRDM14 Forward
      primer

<400> SEQUENCE: 85

```
tgccctgttg ttttaggact gt                                              22
```

<210> SEQ ID NO 86
<211> LENGTH: 22
<212> TYPE: DNA
<213> ORGANISM: Artificial Sequence
<220> FEATURE:
<223> OTHER INFORMATION: Synthetic sequence - monkey PRDM14 Reverse primer

<400> SEQUENCE: 86
aaccagcagt taaggaaagg ct					22

<210> SEQ ID NO 87
<211> LENGTH: 26
<212> TYPE: DNA
<213> ORGANISM: Artificial Sequence
<220> FEATURE:
<223> OTHER INFORMATION: Synthetic sequence - monkey POU5F1 Forward primer

<400> SEQUENCE: 87
gggaggagct agggaaagag aaccta					26

<210> SEQ ID NO 88
<211> LENGTH: 21
<212> TYPE: DNA
<213> ORGANISM: Artificial Sequence
<220> FEATURE:
<223> OTHER INFORMATION: Synthetic sequence - monkey POU5F1 Reverse primer

<400> SEQUENCE: 88
cccccacccg ttgtgttccc a					21

<210> SEQ ID NO 89
<211> LENGTH: 21
<212> TYPE: DNA
<213> ORGANISM: Artificial Sequence
<220> FEATURE:
<223> OTHER INFORMATION: Synthetic sequence - monkey NANOG Forward primer

<400> SEQUENCE: 89
tgttccggtt tccattatgc c					21

<210> SEQ ID NO 90
<211> LENGTH: 20
<212> TYPE: DNA
<213> ORGANISM: Artificial Sequence
<220> FEATURE:
<223> OTHER INFORMATION: Synthetic sequence - monkey NANOG Reverse primer

<400> SEQUENCE: 90
taggctccaa ccatactcca					20

<210> SEQ ID NO 91
<211> LENGTH: 22
<212> TYPE: DNA
<213> ORGANISM: Artificial Sequence
<220> FEATURE:
<223> OTHER INFORMATION: Synthetic sequence - monkey GATA4 Forward primer

<400> SEQUENCE: 91
caaatcccct tcatacccac ca					22

<210> SEQ ID NO 92
<211> LENGTH: 22
<212> TYPE: DNA
<213> ORGANISM: Artificial Sequence
<220> FEATURE:
<223> OTHER INFORMATION: Synthetic sequence - monkey GATA4 Reverse primer

<400> SEQUENCE: 92
tgccatctct taaaccgaac ca                                          22

<210> SEQ ID NO 93
<211> LENGTH: 20
<212> TYPE: DNA
<213> ORGANISM: Artificial Sequence
<220> FEATURE:
<223> OTHER INFORMATION: Synthetic sequence - monkey T Forward primer

<400> SEQUENCE: 93
tgctgtccca agtggcttac                                             20

<210> SEQ ID NO 94
<211> LENGTH: 20
<212> TYPE: DNA
<213> ORGANISM: Artificial Sequence
<220> FEATURE:
<223> OTHER INFORMATION: Synthetic sequence - monkey T Reverse primer

<400> SEQUENCE: 94
ctggaccctg gcaaacatct                                             20

<210> SEQ ID NO 95
<211> LENGTH: 63
<212> TYPE: DNA
<213> ORGANISM: Artificial Sequence
<220> FEATURE:
<223> OTHER INFORMATION: Synthetic sequence - BATAG175

<400> SEQUENCE: 95
gggagcttca ccacttcatt gacggcttta atgagagaaa agcaactgga tgcgctatgt    60
gaa                                                                  63

<210> SEQ ID NO 96
<211> LENGTH: 59
<212> TYPE: DNA
<213> ORGANISM: Artificial Sequence
<220> FEATURE:
<223> OTHER INFORMATION: Synthetic sequence - BTAG196

<400> SEQUENCE: 96
gggagcttca ccacttcatt gacggcttta atgaaaagca actggatgcg ctatgtgaa     59

<210> SEQ ID NO 97
<211> LENGTH: 64
<212> TYPE: DNA
<213> ORGANISM: Artificial Sequence
<220> FEATURE:
<223> OTHER INFORMATION: Synthetic sequence - BTAG1724

<400> SEQUENCE: 97
gggagcttca ccacttcatt gacggcttta atgaagagaa aagcaactgg atgcgctatg    60
tgaa                                                                 64

<210> SEQ ID NO 98
<211> LENGTH: 71

```
<212> TYPE: DNA
<213> ORGANISM: Artificial Sequence
<220> FEATURE:
<223> OTHER INFORMATION: Synthetic sequence - BLIMP1-ref

<400> SEQUENCE: 98
tggtacctgt aaaggtcaaa caagaaacag ttgaaccaat ggatccttaa gattttcaga    60
aaacacttat t                                                         71

<210> SEQ ID NO 99
<211> LENGTH: 71
<212> TYPE: DNA
<213> ORGANISM: Artificial Sequence
<220> FEATURE:
<223> OTHER INFORMATION: Synthetic sequence - 585A1-1

<400> SEQUENCE: 99
tggtacctgt aaaggtcaaa caagaaacag ttgaaccaat ggatccttaa gattttcaga    60
aaacacttat t                                                         71

<210> SEQ ID NO 100
<211> LENGTH: 71
<212> TYPE: DNA
<213> ORGANISM: Artificial Sequence
<220> FEATURE:
<223> OTHER INFORMATION: Synthetic sequence - 585A1-4

<400> SEQUENCE: 100
tggtacctgt aaaggtcaaa caagaaacag ttgaaccaat ggatccttaa gattttcaga    60
aaacacttat t                                                         71

<210> SEQ ID NO 101
<211> LENGTH: 55
<212> TYPE: DNA
<213> ORGANISM: Artificial Sequence
<220> FEATURE:
<223> OTHER INFORMATION: Synthetic sequence - 585A1-23

<400> SEQUENCE: 101
tggtacctgt aaagttgaac caatggatcc ttaagatttt cagaaaacac ttatt         55

<210> SEQ ID NO 102
<211> LENGTH: 71
<212> TYPE: DNA
<213> ORGANISM: Artificial Sequence
<220> FEATURE:
<223> OTHER INFORMATION: Synthetic sequence - 585B1-3

<400> SEQUENCE: 102
tggtacctgt aaaggtcaaa caagaaacag ttgaaccaat ggatccttaa gattttcaga    60
aaacacttat t                                                         71

<210> SEQ ID NO 103
<211> LENGTH: 69
<212> TYPE: DNA
<213> ORGANISM: Artificial Sequence
<220> FEATURE:
<223> OTHER INFORMATION: Synthetic sequence - 585B1-6

<400> SEQUENCE: 103
tggtacctgt aaaggtcaaa caagacagtt gaaccaatgg atccttaaga ttttcagaaa    60
acacttatt                                                            69
```

```
<210> SEQ ID NO 104
<211> LENGTH: 71
<212> TYPE: DNA
<213> ORGANISM: Artificial Sequence
<220> FEATURE:
<223> OTHER INFORMATION: Synthetic sequence - 585B1-8

<400> SEQUENCE: 104
tggtacctgt aaaggtcaaa caagaaacag ttgaaccaat ggatccttaa gattttcaga      60
aaacacttat t                                                          71

<210> SEQ ID NO 105
<211> LENGTH: 70
<212> TYPE: DNA
<213> ORGANISM: Artificial Sequence
<220> FEATURE:
<223> OTHER INFORMATION: Synthetic sequence - TFAP2C-ref

<400> SEQUENCE: 105
ccctggagaa aatggagaaa cacaggaaat aaaattggaa cgaagaaagg ttaggagagt      60
agggaaggaa                                                            70

<210> SEQ ID NO 106
<211> LENGTH: 70
<212> TYPE: DNA
<213> ORGANISM: Artificial Sequence
<220> FEATURE:
<223> OTHER INFORMATION: Synthetic sequence - 585A1-27-3

<400> SEQUENCE: 106
ccctggagaa aatggagaaa cacaggaaat aaaattggaa cgaagaaagg ttaggagagt      60
agggaaggaa                                                            70

<210> SEQ ID NO 107
<211> LENGTH: 70
<212> TYPE: DNA
<213> ORGANISM: Artificial Sequence
<220> FEATURE:
<223> OTHER INFORMATION: Synthetic sequence - 585A1-27-4

<400> SEQUENCE: 107
ccctggagaa aatggagaaa cacaggaaat aaaattggaa cgaagaaagg ttaggagagt      60
agggaaggaa                                                            70

<210> SEQ ID NO 108
<211> LENGTH: 70
<212> TYPE: DNA
<213> ORGANISM: Artificial Sequence
<220> FEATURE:
<223> OTHER INFORMATION: Synthetic sequence - 585A1-27-6

<400> SEQUENCE: 108
ccctggagaa aatggagaaa cacaggaaat aaaattggaa cgaagaaagg ttaggagagt      60
agggaaggaa                                                            70

<210> SEQ ID NO 109
<211> LENGTH: 70
<212> TYPE: DNA
<213> ORGANISM: Artificial Sequence
<220> FEATURE:
<223> OTHER INFORMATION: Synthetic sequence - 585B1-8-2

<400> SEQUENCE: 109
```

```
ccctggagaa aatggagaaa cacaggaaat aaaattggaa cgaagaaagg ttaggagagt     60
agggaaggaa                                                           70

<210> SEQ ID NO 110
<211> LENGTH: 70
<212> TYPE: DNA
<213> ORGANISM: Artificial Sequence
<220> FEATURE:
<223> OTHER INFORMATION: Synthetic sequence - 585B1-8-3

<400> SEQUENCE: 110
ccctggagaa aatggagaaa cacaggaaat aaaattggaa cgaagaaagg ttaggagagt     60
agggaaggaa                                                           70

<210> SEQ ID NO 111
<211> LENGTH: 70
<212> TYPE: DNA
<213> ORGANISM: Artificial Sequence
<220> FEATURE:
<223> OTHER INFORMATION: Synthetic sequence - 585B1-8-6

<400> SEQUENCE: 111
ccctggagaa aatggagaaa cacaggaaat aaaattggaa cgaagaaagg ttaggagagt     60
agggaaggaa                                                           70
```

METHOD FOR INDUCING DIFFERENTIATION OF PLURIPOTENT STEM CELLS INTO GERM CELLS

CROSS-REFERENCE TO RELATED APPLICATIONS

This patent application is the U.S. national phase of International Patent Application No. PCT/JP2016/069360, filed Jun. 29, 2016, which claims the benefit of Japanese Patent Application No. 2015-130501, filed on Jun. 29, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 25,186 bytes ASCII (Text) file named "736686Sequence-Listing.txt," created Dec. 27, 2017

TECHNICAL FIELD

The present invention relates to a method for inducing a primordial germ cell-like cell (PGC-like cell) from a pluripotent stem cell via a mesoderm-like cell, a reagent kit therefor, and a method for isolating a cell belonging to a reproductive cell line obtained by the method from a cell population thereof of the cell.

BACKGROUND ART

The germline is the basis for totipotency and persistence and diversity of a multicellular organism are imparted by transmitting genetic information and epigenetic information to the next generation in many multicellular organisms. When an abnormality occurs in the germ line in which human primordial germ cells (PGCs) develop and form spermatozoon or ovum via a complicated and diversified developmental pathway, various developmental disorders such as genetic or acquired diseases and developmental disorders, functional disorders, infertility and the like appear in the offsprings. Therefore, understanding of the mechanism of germ cell formation is very important for the understanding of not only biology but also disease.

The mechanism of gametogenesis in mammals has been studied in mice and many findings were obtained. They provide important information possibly applicable to all animals including human. However, in variously existing animal species, elaborate mechanisms concerning germ cell development vary markedly among species. For accurate understanding in each species, findings in each animal species are considered to be necessary.

Information on the mechanism of germ cell development in human is very lacking. This is caused by the difficulty in obtaining experiment materials. As described above, since the mechanism of human germ cell formation is unknown, diagnosis/treatment of diseases caused by defects in human germ cells has been difficult.

Breakthrough is said to occur by reconstituting the development of human germ cells in vitro using human pluripotent stem cells (hPSCs) such as human embryonic stem cells (hESCs) (non-patent document 1) and human induced pluripotent stem cells (hiPSCs) (non-patent document 2).

Induction from pluripotent stem cells (PSCs) to mouse germline and the development thereafter have been reproduced in vitro (non-patent document 3 and non-patent document 4). That is, recent studies have clarified that mouse (m) with pluripotency of ground state ESCs/iPSCs (non-patent document 5) is induced to pre-gastrulation ectoderm-like cells (EpiLCs), and successively to PGC-like cells (PGCLCs) having epigenetic properties extremely similar to migratory PGCs and global transcription. Surprisingly, PGCLCs induced in this manner have high capacity in both the formation of spermatozoon and ovum and progeny generation, and these facts propose a conceptual framework for the reconstruction of human germ cell development in vitro and suggest that such reconstruction can be realized.

However, hESCs/iPSCs are different from mESCs/iPSCs in terms of gene expression profile, epigenetic property, cytokine dependency, and differentiation potency, and are considered to be in pluripotency state similar to mouse ectoderm stem cells (epiblast stem cells (EpiSCs)) (non-patent document 6 and non-patent document 7). Such state is similar to post-gastrulation mouse epiblast, which means that capacity of germ cell differentiation is limited (non-patent document 4). Therefore, whether hESCs/iPSCs are efficiently induced to the human germ cell fate is unknown; however, there are many reports teaching that random differentiation of hESCs/iPSCs produces germ cell-like cells with low efficiency (non-patent document 8).

DOCUMENT LIST

Non-Patent Documents non-patent document 1: Thomson J A, et al., Science. 282, 1145-1147, 1998
non-patent document 2: Takahashi K, et al., Cell. 131, 861-872, 2007
non-patent document 3: Hayashi K, et al., Science. 338, 971-975, 2012
non-patent document 4: Hayashi K, et al., Cell. 146, 519-532, 2011
non-patent document 5: Ying Q L, et al., Nature. 453, 519-523, 2008
non-patent document 6: Brons I G, et al. Nature. 448, 191-195, 2007
non-patent document 7: Tesar P J, et al., Nature. 448, 196-199, 2007
non-patent document 8: Hayashi Y, et al., Fertil Steril. 97, 1250-1259, 2012

SUMMARY OF THE INVENTION

Problems to be Solved by the Invention

Therefore, an object of the present invention is to provide a method for inducing human primordial germ cell-like (PGC-like) cells from human pluripotent stem cells, which method having high efficiency and high reproducibility, thereby achieving functional reconstitution of germ cell differentiation determination pathway from pluripotent stem cells including ESC and iPSC in vitro. Another object of the present invention is to provide a cell surface marker to identify human PGC-like cells.

Means of Solving the Problems

It was considered that differentiation of human pluripotent stem cell into human PGC-like cell could be induced by the method described in Hayashi K, et al., Cell. 146, 519-532, 2011 as in mouse. However, the present inventors used this method and found that many dead cells were developed and the induction efficiency was markedly low.

To achieve an object of efficient induction of human PGC-like cells, the present inventors cultured human pluripotent stem cells in a culture medium containing activin A and GSK3β inhibitor, induced mesoderm-like cells, and subjected the mesoderm-like cells to induction conditions for mouse PGC-like cells. Surprisingly, they have found that the induction efficiency of PGC-like cells increased and the development of dead cells can be suppressed.

Furthermore, the present inventors have found at least one marker gene selected from the group consisting of PECAM (CD31), INTEGRINα6 (CD49f), INTEGRINβ3 (CD61), KIT (CD117), EpCAM, PODOPLANIN and TRA1-81 as a cell surface marker for identifying human PGC-like cells. They have conducted further studies based on these findings and completed the present invention.

That is, the present invention relates to the following.

[1] A method for producing a human primordial germ cell-like (PGC-like) cell from a human pluripotent stem cell, comprising the following steps I) and II):
I) a step of producing a mesoderm-like cell by culturing a human pluripotent stem cell in a culture medium comprising activin A and a GSK3β inhibitor,
II) a step of culturing the mesoderm-like cell obtained in step I) in a culture medium containing BMP.
[2] The method of [1] wherein the culture in the aforementioned step I) is performed for less than 60 hr.
[3] The method of [2] wherein the culture in the aforementioned step I) is performed for 42 hr.
[4] The method of [1] wherein the aforementioned GSK3β inhibitor is CHIR99021.
[5] The method of any one of [1] to [4] wherein the culture medium in the aforementioned step I) further comprises a fibroblast growth factor receptor (FGFR) inhibitor.
[6] The method of [5] wherein the aforementioned FGFR inhibitor is PD173074.
[7] The method of any one of [1] to [6] wherein the culture medium in the aforementioned step I) does not contain bFGF and BMP.
[8] The method of any one of [1] to [7] wherein the culture medium in the aforementioned step II) further comprises at least one cytokine selected from the group consisting of SCF, EGF and LIF.
[9] The method of any one of [1] to [8] wherein the aforementioned pluripotent stem cell is a pluripotent stem cell cultured under serum-free and feeder-free conditions.
[10] The method of [9] wherein the culturing under the aforementioned feeder-free conditions is culturing on laminin511 or laminin511 fragment.
[11] The method of any one of [1] to [10] further comprising III) a step of selecting a cell positive to at least one cell surface marker selected from the group consisting of PECAM (CD31), INTEGRINα6 (CD49f), INTEGRINβ3 (CD61), KIT (CD117), EpCAM, PODOPLANIN and TRA1-81 from the cells obtained in the aforementioned step II).
[12] The method of [11] wherein the aforementioned step III) is a step of selecting a double positive cell of INTEGRINα6 (CD49f) and EpCAM.
[13] The method of any one of [1] to [12] wherein the aforementioned human pluripotent stem cell is a human iPS cell.
[14] A cell population comprising a human primordial germ cell-like (PGC-like) cell produced by the method of any one of [1] to [13].
[15] A method for sorting a human primordial germ cell-like (PGC-like) cell comprising selecting a cell positive to at least one cell surface marker selected from the group consisting of PECAM (CD31), INTEGRINα6 (CD49f), INTEGRINβ3 (CD61), KIT (CD117), EpCAM, PODOPLANIN and TRA1-81.
[16] The method of [15] wherein the aforementioned selection is performed by selecting a double positive cell of INTEGRINα6 (CD49f) and EpCAM.
[17] A reagent kit for inducing differentiation of a human pluripotent stem cell into a human primordial germ cell-like (PGC-like) cell comprising the following (1) and (2):
(1) a reagent for inducing a human pluripotent stem cell into a mesoderm-like cell comprising activin A and a GSK3β inhibitor,
(2) a reagent for inducing a mesoderm-like cell into a human primordial germ cell-like (PGC-like) cell comprising BMP.
[18] The kit of [17] wherein the aforementioned GSK3β inhibitor is CHIR99021.
[19] The kit of [17] or [18] wherein the induction reagent of the aforementioned (1) further comprises a fibroblast growth factor receptor (FGFR) inhibitor.
[20] The kit of [19] wherein the aforementioned FGFR inhibitor is PD173074.
[21] The kit of any one of [17] to [20] wherein the induction reagent of the aforementioned (2) further comprises at least one cytokine selected from the group consisting of SCF, EGF and LIF.
[22] The kit of any one of [17] to [21] further comprising (3) a reagent for isolating a human primordial germ cell-like (PGC-like) cell comprising an antibody to at least one cell surface marker selected from the group consisting of PECAM (CD31), INTEGRINα6 (CD49f), INTEGRINβ3 (CD61), KIT (CD117), EpCAM, PODOPLANIN and TRA1-81.
[23] The kit of [22] wherein the isolation reagent of the aforementioned (3) comprises an antibody to INTEGRINα6 (CD49f) and an antibody to EpCAM.

Effect of the Invention

When human pluripotent stem cells are cultured in a culture medium containing activin A and a GSK3β inhibitor to induce mesoderm-like cells, and the cells are cultured under conditions for induction into mouse PGC-like cells, the induction efficiency of human PGC-like cells increases and the development of dead cells can be suppressed. Thus, human PGC-like cells can be induced from human pluripotent stem cells with high efficiency and good reproducibility. In addition, using the cell surface marker identified by the present invention as an index, human PGC-like cells can be efficiently isolated and purified from a cell population.

BRIEF DESCRIPTION OF THE DRAWINGS

FIG. 1A shows bright field images of BTAG 585B1-868 hiPSCs (left figure), and the results of FACS measurement of expression of OCT3/4, SOX2, NANOG, TRA-1-60 and SSEA-4 (right figure). FIG. 1B is an outline figure showing the scheme for directly inducing BTAG(+) cells from hiPSCs. FIG. 1C shows bright field image (BF) and fluorescence images (AG and BT) of floating aggregates of hiPSCs stimulated by BMP4, SCF, EGF and LIF (left figure), and bright field image (BF) and fluorescence images (AG and BT) of floating aggregates of hiPSCs under conditions without addition of cytokine (right figure). FIG. 1D shows the results of FACS analysis of the expression of BTAG up to day 8 during direct induction from hiPSCs by BMP4, SCF, EGF and LIF (left figure), and the results of FACS analysis of the expression of BTAG up to day 8 of hiPSCs under conditions without addition of cytokine (right figure). In the figures, the numbers show content percentage of BTAG(+) cells. FIG. 1E shows the results the number of BTAG(+) cells plotted for each aggregate. The average is shown with the horizontal line, percentile from 25 to 75 are shown in box, and the maximum value and minimum value of the two results are shown with error bars. FIG. 1F shows the results of gene expression during induction of BTAG(+) cells (hiPSCs, 2 days of induction (day 2) and 6 days of induction (day 6)) measured by Q-PCR. The expression level of each gene is shown by ΔCT from average CT value of two housekeeping genes of Arbp (attachment region binding protein) and Ppia (peptidylprolyl Isomerase A).

FIG. 2A is an outline figure showing the scheme for inducing BTAG(+) cells via iMeLCs. FIG. 2B shows phase contrast microscopic images of hiPSCs (left figure) and iMeLCs (right figure). FIG. 2C shows the results of expression of OCT3/4, SOX2 and NANOG in iMeLCs on day 42 of induction measured by FACS. FIG. 2D shows bright field image (BF) and fluorescence images (AG and BT) of floating aggregates of hiPSCs stimulated by BMP4, SCF, EGF and LIF at respective induction days (day 2, day 4, day 6 and day 8) (left figure), and bright field image (BF) and fluorescence images (AG and BT) of floating aggregates of hiPSCs under conditions without addition of cytokine (right figure). FIG. 2E shows coagulation of iMeLCs stimulated by BMP4, SCF, EGF and LIF (top figure), and BTAG positive cells measured by FACS under conditions without addition of cytokine (lower figure). In the figures, the numbers show content percentage of BTAG(+) cells. FIG. 2F shows content percentage of BTAG(+) cells (left figure) and the results the number of BTAG(+) cells plotted for each aggregate (right figure). The average is shown with the horizontal line, percentile from 25 to 75 are shown in box, and the maximum value and minimum value of the two results are shown with error bars. FIG. 2G shows the results of gene expression during induction of BTAG(+) cells (hiPSCs, iMeLCs, 2 days of induction (day 2), 4 days of induction (day 4), 6 days of induction (day 6), 8 days of induction (day 8)) measured by Q-PCR. The expression level of each gene is shown by ΔCT from average CT value of two housekeeping genes of Arbp and Ppia. FIG. 2H shows the results of FACS measurement of the expression of OCT3/4, SOX2 and NANOG in BTAG (+) cell on induction day 4. FIG. 2I shows fluorescent staining images of BLIMP1, TFAP2C, SOX2 and SOX17 in BTAG(+)PGCLCs (primordial germ cell-like cells) (middle figure eGFP) on induction day 8 (right figure). In the right figure, the broken line shows BTAG(+)PGCLCs in the middle figure.

FIG. 3A shows the cluster analysis results of transcriptome of BTAG(+) cells (BTAG+d6) directly induced from hiPSCs, iMeLCs, BTAG(+) cells (induction day 2 (d 2), induction day 4 (d 4), induction day 6 (d 6) and induction day 8 (d 8) from iMeLCs) and hiPSCs. FIG. 3B shows PCA analysis results during induction of hiPSCs, iMeLCs and BTAG(+) cells (induction day 2 (d2 BTAG+) and induction day 4 (d4 BTAG+) from iMeLCs). FIG. 3C shows the results of plotting of a gene with upward change or downward change between cyESCs (CMK9) and cyPGCs by comparison of expression respective cells (left figure) and a graph of frequency distribution of the gene (right figure). FIG. 3D shows cluster analysis results during BTAG (+) positive cell induction and based on gene expression of cell types of cyESCs (CMK9) and cyPGCs (PGCd43, PGCd50 and PGCd51). FIG. 3E shows expression change gene (DEG) between hPGCs and H9 ESCs plotted in d6 BTAG(+) cells and iMeLCs (top figure) and a graph of frequency distribution of the gene (lower figure). FIG. 3F shows cluster analysis results during BTAG(+) positive cell induction and based on gene expression of ESC and PGC. FIG. 3G shows scatter diagram plotting a gene with log 2 fold change between cells before induction and d4 TNAP/ NANOS3(+) cells and a gene with log 2 fold change between iMeLCs and d4 BTAG(+) cells (top figure), and scatter diagram plotting a gene with log 2 fold change between cells before induction and d4 TNAP/NANOS3(+) cells and a gene with log 2 fold change between iMeLCs and d4 TNAP/NANOS3(+) cells (lower figure).

FIG. 4A shows the measurement results of the number of genes with an increase and decrease in the expression between cells of human (left figure) and mouse (right figure) in the main stage. FIG. 4B shows the results of gene ontology (GO) analysis between the cells of FIG. 4A. FIG. 4C shows measurement results of the number of genes showing high expression in each cell type between PGCLC of human (left figure) and mouse (right figure). FIG. 4D shows the results of gene ontology (GO) analysis between the cells of FIG. 4C. FIG. 4E shows Venn diagram showing overlap of human and mouse d2 PGCLC genes shown in FIG. 4C. FIG. 4F and FIG. 4G show the results of plotting of the expression of human d2 PGCLC gene (FIG. 4F) and mouse d2 PGCLC gene (FIG. 4G) in each human cell (left figure) and each mouse cell (right figure). The average is shown with the horizontal line, percentile from 25 to 75 are shown in box, and the maximum value and minimum value of the two results are shown with error bars. FIG. 4H shows heat map of the expression of a gene relating to mouse primitive pluripotency and epiblast (left figure) and a gene relating to mesoderm and endoderm (right figure) in mESCs, mEpiLCs, mEpiSCs, hiPSCs and iMeLCs. The gene expression data was obtained from microarray analysis and RNA-seq.

FIG. 5A shows FACS analysis results of the expression of EpCAM and INTEGRINα6 in aggregates on day 6 of induction from hiPSCs via iMeLCs. FIG. 5B shows the FACS analysis results of the expression of EpCAM and INTEGRINα6 in aggregates up to induction day 8 from hiPSCs via iMeLCs (top figure). In the figure, Full shows induction results in BMP4, LIF, SCF and EGF, No cytokine shows induction results under conditions without addition of cytokine. The lower figure shows the measurement results of the content percentage of BTAG(+) cells in the gates (P3 and P5) under respective conditions. FIG. 5C shows the FACS analysis results of the expression of EpCAM and INTEGRINα6 in aggregates up to induction day 6 from 585A1 hiPSCs (cells free of knockin with BT and AG) via hPGCLC. In the figure, Full shows induction results in BMP4, LIF, SCF and EGF, No cytokine shows induction results under conditions without addition of cytokine. FIG. 5D shows the cluster analysis results of transcriptome of hiPSCs, iMeLCs, BTAG(+) cells induced via iMeLCs (day 2, day 4, day 6 and day 8) and high expressing cells (day 6) of EpCAM and INTEGRINα6 induced from 585A1 hiPSCs via iMeLCs. FIG. 5E shows FACS analysis results of the expression of EpCAM and INTEGRINα6 in aggregates on day 6 of induction via iMeLCs induced from 1383D2 (left figure) and 1383D6 (right figure) using FGFRi (top figure). The middle figure and lower figure shows FACS analysis results of the expression of EpCAM and INTEGRINα6 in aggregates on day 4 of induction via iMeLCs (middle figure) induced from 201B7 without using FGFRi or iMeLCs (lower figure) induced using FGFRi.

FIG. 6A shows construction figure of targeting vector for BLIMP1. FIG. 6B shows immunostaining figures of the expression of AG and BLIMP1 in hPGCLCs induced from hiPSCs (BLIMP1+/+ cells (1-7, or 1-9) or BTAG−/− cells (1-7-5 or 1-9-6)) via iMeLCs. The broken line in the lower figure shows the position of AG positive cell. FIG. 6C shows a bright field image (BF) and fluorescence images (AG and BT) of cell aggregates (day 2, day 4 and day 6) induced from wild-type (left figure), BLIMP1+/− (middle figure) or BLIMP1−/− (right figure) via iMeLCs. FIG. 6D shows FACS analysis results of the content percentage of AG positive cells in cell aggregates (day 2, day 4, day 6 and day 8) induced from wild-type (top figure), BLIMP1+/− (middle figure) or BLIMP1−/− (lower figure) via iMeLCs, hiPSCs and iMeLCs. FIG. 6E shows the number of AG positive cells in the cell aggregates induced from wild-type (wt), BLIMP1+/− (het) or BLIMP1−/− (ko) via iMeLCs. FIG. 6F shows Q-PCR measurement results of the expression of each gene in AG positive cells on day 2 or day 4 of induction from wild-type (wt) or BLIMP1−/− (ko) via iMeLCs.

FIG. 7A shows cluster analysis results of the transcriptome of hiPSCs (wild-type (wt), BLIMP1+/− (het) or BLIMP1−/− (ko)) and AG positive cells on induction day 2 and day 4 from hiPSCs. FIG. 7B shows PCA analysis results in FIG. 7A. FIG. 7C shows the number of genes that showed increased or decreased expression in BLIMP1−/− hiPSCs and AG positive cells on induction day 2 and day 4 as compared to wild-type. FIG. 7D shows the results of gene ontology (GO) analysis shown in FIG. 7C. FIG. 7E shows the results of plotting of the increased gene (left figure) and decreased gene (right figure) in the expression in each cell in FIG. 7C. The average is shown with the horizontal line, percentile from 25 to 75 are shown in box, and the maximum value and minimum value of the two results are shown with error bars. FIG. 7F shows change of gene relating to neuron differentiation from the genes that showed expression change in hiPSCs and d2 and d4 hPGCLCs.

FIG. 8A shows single-strand annealing (SSA) activity of TALEN relative to TFAP2C (left figure) or BLIMP1 (right figure). FIG. 8B shows schematic showing of BLIMP1 and TFAP2C gene loci and schematic showing of the knockin strategy. FIG. 8C shows PCR screening results of the homologous recombination of BLIMP1-2A-tdTomato (top figure) and TFAP2C-2A-EGFP (lower figure). FIG. 8D shows karyotype analysis results of 585A1, 585B1 and BTAG 585B1-868 hiPSCs. FIG. 8E shows fluorescent staining images of BLIMP1-2A-tdTomato (two top figures) and TFAP2C-2A-EGFP (lower figure). FIG. 8F shows FACS measurement results of the content percentage of BTAG(+) cells per cell aggregate when BMP4, LIF, SCF and EGF were used, LIF alone was used, and KSR at each concentration was used during BTAG(+) cell induction.

FIG. 9A shows bright field image, fluorescence image and FACS analysis results of BTAG(+) cells (day 4) induced via iMeLCs or directly induced BTAG(+) cells (day 6). FIG. 9B shows FACS analysis results during induction of iMeLCs (top figure) and cell number measurement results (lower figure). FIG. 9C shows Q-PCR measurement results of each gene during induction of iMeLCs from hiPSCs.

FIG. 10A to 10E show FACS measurement results of the content percentage of BTAG(+) cells when the concentration of activin A (ACTA) (FIG. 10A), Wnt3A (FIG. 10B), CHIR99021 (FIG. 10C), BMP4 (FIG. 10D) or bFGF (FIG. 10E) was changed during induction of iMeLC from hiPSCs. FIG. 10F shows phase contrast microscopic images of the cells after 42 hr from the induction of hiPSCs using ACTA and CHIR99021, ACTA alone, CHIR99021 alone or without addition thereof. FIG. 10G shows bright field image, fluorescence image and measurement results of cell number of BTAG(+) cells when a FGFR inhibitor (FGFRi) was used. FIG. 10H shows Q-PCR measurement results of the expression of gene BTAG(+) in the cells when a FGFR inhibitor (FGFRi) was used.

FIG. 11A to FIG. 11D show bright field image, fluorescence image and FACS analysis results of BTAG(+) cells when the concentration of BMP4, the addition concentration of LDN193189, the addition of BMPs (BMP2, BMP4, BMP7 and BMP8a), or the combination of BMP4, LIF, SCF and EGF was changed. FIG. 11E shows change of each gene in BTAG(+) cells up to day 12.

FIG. 12A shows the measurement results, by the immunostaining method, of the expression of OCT3/4, BLIMP1, TFAP2C and DDX4 in gonad of Macaca fascicularis. FIG. 12B shows the measurement results, by single cell Q-PCR, of the expression of PPIA, POU5F1, NANOG, PRDM1 and TFAP2C in gonad of Macaca fascicularis. FIG. 12C shows a phase contrast microscopic image of cyESCs. FIG. 12D shows the measurement results, by single cell Q-PCR, of the expression of PPIA, POU5F1, NANOG, PRDM14, GATA4 and T in cyESCs. FIG. 12E shows PCA analysis results of cyESC and cyPGCs. FIG. 12F shows heat map of suppression of the expression of HOX gene during PGCLC induction in human (left figure) and mouse (right figure). FIG. 12G shows cluster analysis results of the gene expression in mESCs, EpiLCs and EpiSCs. FIG. 12H shows the measurement results of the expression of 4 clusters of the gene in FIG. 12G.

FIG. 13A shows stained images of H3K9me2, H3K27me3 and 5mC and cell distribution of the fluorescence intensity. FIG. 13B shows the ratio of CpG methylation of H19, MEG3, KCNQ1 and PEG10. FIG. 13C shows the analysis results, the RNA-seq method, of the expression of gene in cyESCs and gonad PGCs during hPGCLC induction.

FIG. 14A shows SSA activity of TALEN when targeting exon4 of BLIMP1. FIG. 14B shows homologous recombination of TFAP2C-2A-EGFP (top figure), BLIMP1-exon4-2A-tdTomato (middle figure) and PCR analysis results of targeting vector. FIG. 14C shows scatter diagram of comparison of the expression of RNA-seq of BLIMP1+/+ (wt) cells (left figure) and d2 BTAG(+) cells (middle figure) and d4 BTAG(+) cells (right figure) relative to BLIMP1−/− (ko) cells. FIG. 14D shows variation in the expression of epigenetic-related genes of hPGCLC induced from BLIMP1+/+ (wt) cells, BLIMP1+/− (het) cells and BLIMP1−/− (ko) cells. FIG. 14E shows change of gene relating to neuron differentiation from the genes that showed expression change in BLIMP1+/+ (wt) or BLIMP1−/− (ko) hiPSCs and d2 and d4 hPGCLCs induced from said cells.

DESCRIPTION OF EMBODIMENTS

Figure 1:
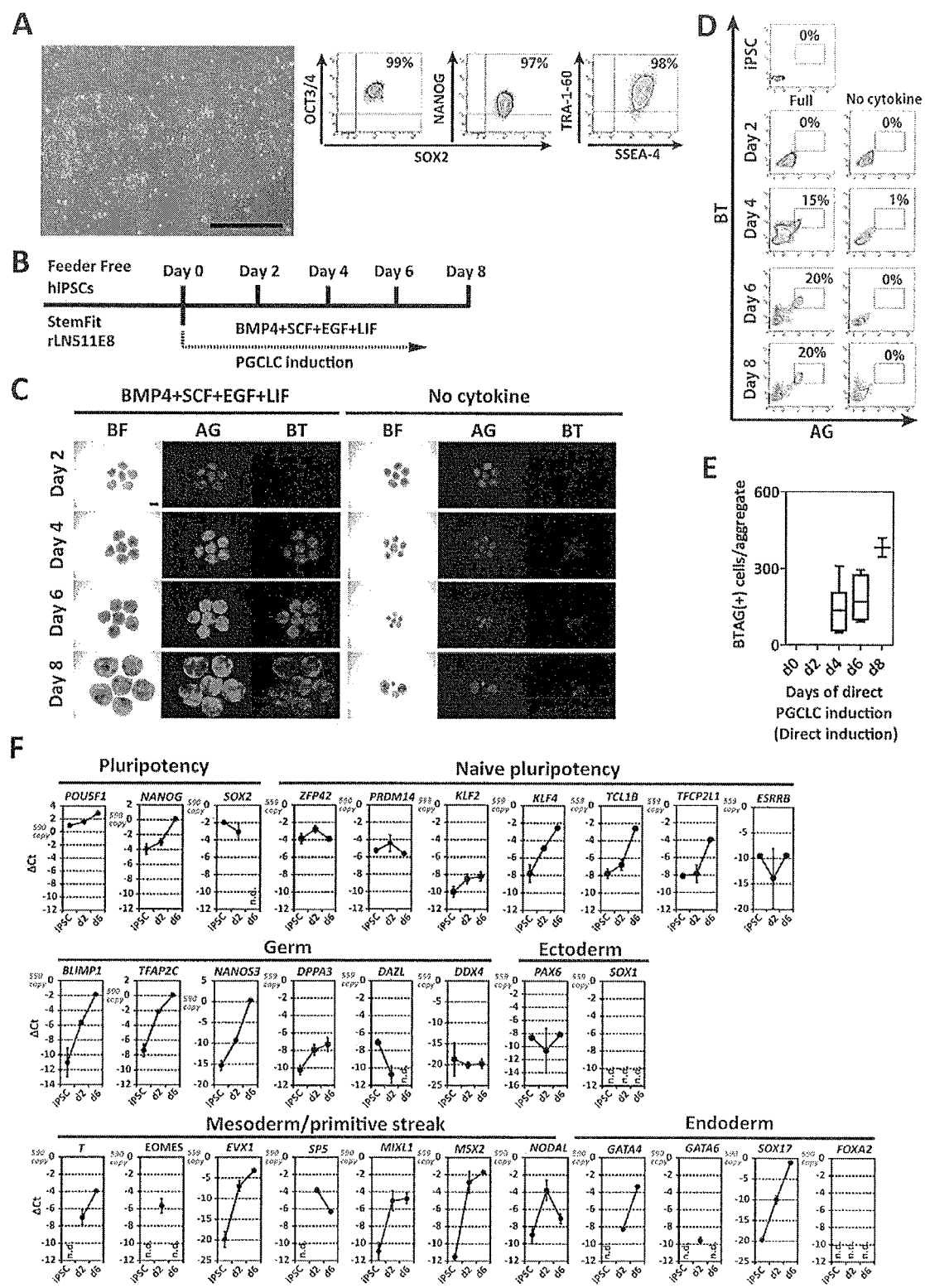
FIG. 1 shows the results of direct induction of BTAG(+) cells from hiPSCs.

The present invention provides a method for producing mesoderm-like cells from human pluripotent stem cells, which is a method for culturing the aforementioned human pluripotent stem cells in a culture medium added with activin A and a glycogen synthase kinase (GSK) 3β inhibitor.

The human pluripotent stem cell to be used as a starting material may be any undifferentiated cell as long as it has "self-replication competence" permitting proliferation while maintaining an undifferentiated state, and "differentiation pluripotency" permitting differentiation into all three primary germ layers. For example, iPS cell, ES cell, embryonic germ (EG) cell, embryonic carcinoma (EC) cell and the like can be mentioned, with preference given to iPS cell or ES cell.

(1) Production of Human Pluripotent Stem Cell
(i) ES Cell

Pluripotent stem cell can be obtained by a method known per se. For example, as a production method of ES cells, a method including culturing inner cell mass of mammalian blastocyst stage (Thomson J A, et al., Science. 282, 1145-1147, 1998) can be mentioned, but the method is not limited thereto. ES cell can be obtained from given institutions and a commercially available product can also be purchased. For example, human ES cell lines H1 and H9 are available from WiCell Institute of University of Wisconsin, and KhES-1, KhES-2 and KhES-3 are available from Institute for Frontier Medical Science, Kyoto University.

(ii) iPS Cell iPS cell can be produced by transferring a nuclear reprogramming substance to the somatic cell.

(A) Sources of Somatic Cells

Examples of somatic cells that can be used as a starting material for the production of iPS cell include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigmenT cells (e.g., retinal pigment epithelial cells), progenitor cells thereof (tissue progenitor cells) and the like. There is no limitation on the degree of cell differentiation, and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as fat derived from stroma (stem) cells, neural stem cells, hematopoietic stem cells, mesenchymal stem cells, and dental pulp stem cells.

Somatic cells isolated from a mammal can be pre-cultured using a medium known per se suitable for their cultivation according to the choice of cells. Examples of such media include, but are not limited to, minimal essential medium (MEM) containing about 5 to 20% fetal bovine serum (FCS), Dulbecco's modified Eagle medium (DMEM), RPMI1640 medium, 199 medium, F12 medium, and the like. When a transfer reagent such as cationic liposome, for example, is used in bringing a cell into contact with nuclear reprogramming substances and another iPS cell establishment efficiency improver, it is sometimes preferable that the medium have been replaced in advance with a serum-free medium so as to prevent the transfer efficiency from decreasing.

(b) Nuclear Reprogramming Substance

In the present invention, "a nuclear reprogramming substance" may be configured with any substance, such as a proteinous factor or a nucleic acid that encodes the same (including a form integrated in a vector), or a low molecular compound, as long as it is a substance (substances) capable of inducing an iPS cell from a somatic cell. When the nuclear reprogramming substance is a proteinous factor or a nucleic acid that encodes the same, preferable nuclear reprogramming substance is exemplified by the following combinations (hereinafter, only the names for proteinous factors are shown).

(1) Oct3/4, Klf4, c-Myc
(2) Oct3/4, Klf4, c-Myc, Sox2 (here, Sox2 is replaceable with Sox1, Sox3, Sox15, Sox17 or Sox18; Klf4 is replaceable with Klf1, Klf2 or Klf5; c-Myc is replaceable with T58A (active mutant), N-Myc or L-Myc)
(3) Oct3/4, Klf4, c-Myc, Sox2, Fbx15, Nanog, Eras, ECAT15-2, Tcll, β-catenin (active mutant S33Y)
(4) Oct3/4, Klf4, c-Myc, Sox2, TERT, SV40 Large T antigen (hereinafter SV40 LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV16 E6, HPV16 E7
(8) Oct3/4, Klf4, c-Myc, Sox2, TERT, Bmi1
[For further information of the above-mentioned factors, see WO 2007/069666 (however, in the combination (2) above, for replacement of Sox2 with Sox18, and replacement of Klf4 with Klf1 or Klf5, see *Nature Biotechnology*, 26, 101-106 (2008)); for details of the combination "Oct3/4, Klf4, c-Myc, Sox2", see also *Cell*, 126, 663-676 (2006), Cell, 131, 861-872 (2007) and the like. For details of the combination of "Oct3/4, Klf4, c-Myc, Sox2", see also Cell, 126, 663-676 (2006), Cell, 131, 861-872 (2007) and the like. For details of the combination of "Oct3/4, Klf2 (or Klf5), c-Myc, Sox2", see also Nat. Cell Biol., 11, 197-203 (2009). For details of the combination of "Oct3/4, Klf4, c-Myc, Sox2, hTERT, SV40LT", see also Nature, 451, 141-146 (2008).)
(9) Oct3/4, Klf4, Sox2 (see also Nature Biotechnology, 26, 101-106 (2008))
(10) Oct3/4, Sox2, Nanog, Lin28 (see Science, 318, 1917-1920 (2007))
(11) Oct3/4, Sox2, Nanog, Lin28, hTERT, SV40LT (see Stem Cells, 26, 1998-2005 (2008))

(12) Oct3/4, Klf4, c-Myc, Sox2, Nanog, Lin28 (see Cell Research (2008) 600-603)
(13) Oct3/4, Klf4, c-Myc, Sox2, SV40LT (see also Stem Cells, 26, 1998-2005 (2008))
(14) Oct3/4, Klf4 (see Nature 454:646-650 (2008), Cell Stem Cell, 2:525-528 (2008))
(15) Oct3/4, c-Myc (see Nature 454:646-650 (2008))
(16) Oct3/4, Sox2 (see Nature, 451, 141-146 (2008), WO 2008/118820)
(17) Oct3/4, Sox2, Nanog (see WO 2008/118820)
(18) Oct3/4, Sox2, Lin28 (see WO 2008/118820)
(19) Oct3/4, Sox2, c-Myc, Esrrb (Esrrb is replaceable with Esrrg. See Nat. Cell Biol., 11, 197-203 (2009))
(20) Oct3/4, Sox2, Esrrb (see Nat. Cell Biol., 11, 197-203 (2009))
(21) Oct3/4, Klf4, L-Myc
(22) Oct3/4, Nanog
(23) Oct3/4
(24) Oct3/4, Klf4, c-Myc, Sox2, Nanog, Lin28, SV40LT (see Science, 324:797-801 (2009))

In the above-mentioned (1)-(24), a member of other Oct family, for example, Oct1A, Oct6 and the like can also be used instead of Oct3/4. In addition, a member of other Sox family, for example, Sox7 and the like can also be used instead of Sox2 (or Sox1, Sox3, Sox15, Sox17, Sox18). Furthermore, a member of other Lin family, for example, Lin28b and the like can also be used instead of Lin28.

Any combination that does not fall in (1) to (24) above but comprises all the constituents of any one of (1) to (22) and further comprises an optionally chosen other substance can also be included in the scope of "nuclear reprogramming substance" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the one or more constituents can also be included in the scope of "nuclear reprogramming substance" in the present invention.

Of these combinations, at least one, preferably two or more, more preferably three or more selected from Oct3/4, Sox2, Klf4, c-Myc, Nanog, Lin28 and SV40LT are preferable nuclear reprogramming substances.

Among these combinations, when the obtained iPS cell is to be used for therapeutic purposes, a combination of 3 factors of Oct3/4, Sox2 and Klf4 (i.e., the above-mentioned (9)) is preferable. On the other hand, when the iPS cell is not to be used for therapeutic purposes (e.g., used as an investigational tool for drug discovery screening and the like), 4 factors of Oct3/4, Sox2, Klf4 and c-Myc, 5 factors of Oct3/4, Klf4, c-Myc, Sox2 and Lin28, or 6 factors further including Nanog (i.e., the above-mentioned (12)) or 7 factors further including SV40 Large T (i.e., the above-mentioned (24)), is preferable.

Furthermore, the above-mentioned combination with L-Myc instead of c-Myc is also a preferable example of a nuclear reprogramming substance.

Information on the mouse and human cDNA sequences of the aforementioned nuclear reprogramming substances is available with reference to the NCBI accession numbers mentioned in WO 2007/069666 (in the publication, Nanog is described as ECAT4. Mouse and human cDNA sequence information on Lin28, Lin28b, Esrrb, Esrrg and L-Myc can be acquired by referring to the following NCBI accession numbers, respectively); those skilled in the art are easily able to isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

When a proteinous factor is used as a nuclear reprogramming substance, it can be prepared by inserting the cDNA obtained into an appropriate expression vector, transferring it into a host cell, culturing the cell, and recovering the recombinant proteinous factor from the cultured cells or a conditioned medium therefor. Meanwhile, when a nucleic acid that encodes a proteinous factor is used as a nuclear reprogramming substance, the cDNA obtained is inserted into a viral vector, plasmid vector, episomal vector or the like to construct an expression vector, which is subjected to the nuclear reprogramming step.

(c) Method of Introducing Nuclear Reprogramming Substance into Somatic Cell

Introduction of the nuclear reprogramming substance with a somatic cell, when the substance is a proteinaceous factor, can be achieved using a method known per se for protein transfer into a cell. In consideration of clinical application to human, iPS cell to be the starting material therefore is also preferably produced without gene manipulation.

Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactive hemagglutinating virus of Japan) and the like. The transfer can be achieved per the protocols attached to these reagents, a common procedure being as described below. The nuclear reprogramming substance is diluted in an appropriate solvent (e.g., a buffer solution such as PBS or HEPES), a transfer reagent is added, the mixture is incubated at room temperature for about 5 to for 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, Cell 55, 1189-93 (1988) or Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1

(Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyargininies such as 11R (*Cell Stem Cell*, 4, 381-384 (2009)) and 9R (*Cell Stem Cell*, 4, 472-476 (2009)).

A fused protein expression vector incorporating cDNA of a nuclear reprogramming substances and PTD or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 µm, and injecting the solution into a cell, ensures the transfer of the protein into the cell.

When the establishment efficiency of iPS cells is important, the nuclear reprogramming substance is also preferably used in the form of a nucleic acid encoding a proteinaceous factor rather than the proteinaceous factor itself. The nucleic acid may be a DNA or an RNA, or a DNA/RNA chimera. The nucleic acid may be double-stranded or single-stranded. Preferably, the nucleic acid is a double-stranded DNA, particularly cDNA.

cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpes virus and Sendai virus, plasmids for the expression in animal cells (e.g., pA1-11, pXT1, pRc/CMV, pRc/RSV, pcDNAI/Neo) and the like.

The type of a vector to be used can be chosen as appropriate according to the intended use of the iPS cell to be obtained. Useful vectors include adenoviral vector, plasmid vector, adeno-associated viral vector, retroviral vector, lentiviral vector, Sendai viral vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

Nucleic acid as a nuclear reprogramming substance (reprogramming gene) may be incorporated on individual expression vectors, 2 or more kinds, preferably 2-3 kinds, of genes may be incorporated into one expression vector. The former case is preferable when using a retroviral or lentiviral vector that offers high gene transfer efficiency, and the latter is preferable when using a plasmid, adenoviral, or episomal vector and the like. Furthermore, an expression vector incorporating 2 or more kinds of genes, and other expression vector incorporating one gene alone can also be used in combination.

In the context above, when multiple reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (PLoS ONE 3, e2532, 2008, Stem Cells 25, 1707, 2007), the IRES sequence (U.S. Pat. No. 4,937,190) and the like, with preference given to the 2A sequence.

An expression vector harboring a nucleic acid which is a nuclear reprogramming substance can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to a cell by a method suitable for the viral vector. For example, specific means using a retroviral vector are disclosed in WO2007/69666, *Cell*, 126, 663-676 (2006) and *Cell*, 131, 861-872 (2007). Specific means using a lentiviral vector is disclosed in *Science*, 318, 1917-1920 (2007). When PGC-like cell induced from iPS cell is utilized as a regenerative medicine for infertility treatment, gene therapy of germ cell and the like, since expression (reactivation) of reprogramming gene may increase the carcinogenic risk of germ cell or reproductive tissue regenerated from PGC-like cell derived from iPS cell, nucleic acid encoding a nuclear reprogramming substance is preferably expressed transiently, without being integrated into the chromosome of the cells. From this viewpoint, it is preferable to use an adenoviral vector, which is unlikely to be integrated into the chromosome, is preferred. Specific means using an adenoviral vector is disclosed in *Science*, 322, 945-949 (2008). Adeno-associated virus vector is unlikely to be integrated into the chromosome, and is less cytotoxic and less phlogogenic than adenoviral vectors, so that it is another preferred vector. Sendai virus vectors are capable of being stably present outside of the chromosome, and can be degraded and removed using an siRNA as required, so that they are preferably utilized as well. Useful Sendai virus vectors are described in *J. Biol. Chem.*, 282, 27383-27391 (2007) or JP-B-3602058.

When a retroviral vector or a lentiviral vector is used, even if silencing of the transgene has occurred, it possibly becomes reactive; therefore, for example, a method can be used preferably wherein a nucleic acid encoding nuclear reprogramming substance is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactive (SIN) LTR prepared by deleting the sequence, or substituting the sequence with a polyadenylation sequence such as of SV40. Specific means using the Cre-loxP system and SIN LTR is disclosed in Chang et al., *Stem Cells*, 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, Science, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., Nature, 458: 771-775 (2009), Woltjen et al., Nature, 458: 766-770 (2009).

Another preferable non-integration type vector is an episomal vector, which is capable of self-replication outside of the chromosome. Specific means using an episomal vector is disclosed by Yu et al., in Science, 324, 797-801 (2009). Where necessary, an expression vector may be constructed by inserting a reprogramming gene into an episomal vector having loxP sequences placed in the same orientation on the 5' and 3' sides of a vector component essential for the replication of the episomal vector, and transferred to a somatic cell.

Examples of the episomal vector include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin ori and the SV40 large T antigen gene for SV40.

The episomal expression vector comprises a promoter that controls the transcription of a reprogramming gene. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

An episomal vector can be transferred into a cell using, for example, the lipofection method, liposome method, electroporation method, calcium phosphate co-precipitation method, DEAE dextran method, microinjection method, gene gun method and the like. Specifically, for example, methods described in Science, 324: 797-801 (2009) and elsewhere can be used.

Whether or not the vector component necessary for the replication of the reprogramming gene has been removed from the iPS cell can be confirmed by performing a Southern blot analysis or PCR analysis using a part of the vector as a probe or primer, with the episome fraction isolated from the iPS cell as a template, and determining the presence or absence of a band or the length of the band detected. The episome fraction can be prepared by a method obvious in the art; for example, methods described in Science, 324: 797-801 (2009) can be used.

When the nuclear reprogramming substance is a low-molecular-weight compound, the substance can be introduced into a somatic cell by dissolving the substance at a suitable concentration in an aqueous or non-aqueous solvent, adding the solution to a medium suitable for the culture of somatic cell isolated from human or mouse (e.g., minimum essential medium (MEM), Dulbecco's modified Eagle medium (DMEM), RPMI1640 medium, 199 medium, F12 medium and the like containing about 5-20% fetal bovine serum such that the concentration of a nuclear reprogramming substance is sufficient to cause nuclear reprogramming in the somatic cell and free of cytotoxicity, and culturing the cells for a given period. While the concentration of the nuclear reprogramming substance varies depending on the kind of the nuclear reprogramming substance to be used, it is appropriately selected from the range of about 0.1 nM-about 100 nM. The contact period is not particularly limited as long as it is sufficient for achieving nuclear reprogramming of the cell. Generally, they may be co-existed in the medium until positive colony emerges.

(d) Establishment Efficiency Improving Substance for iPS Cell

Since the iPS cell establishment efficiency has been low, various substances that improve the efficiency have recently been proposed one after another. It can be expected, therefore, that the iPS cell establishment efficiency will be increased by bringing another establishment efficiency improver, in addition to the aforementioned nuclear reprogramming substance, into contact with the transfer subject somatic cell.

Examples of the iPS cell establishment efficiency improving substance include, but are not limited to, histone deacetylase (HDAC) inhibitors [e.g., low-molecular inhibitors such as valproic acid (VPA) (Nat. Biotechnol., 26(7): 795-797 (2008), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29 mer shRNA Constructs against HDAC1 (OriGene) and the like), and the like], DNA methyl transferase inhibitors (e.g., 5-azacytidine) (Nat. Biotechnol., 26(7):795-797 (2008)), G9a histone methyl transferase inhibitors [for example, low-molecular inhibitors such as BIX-01294 (Cell Stem Cell, 2:525-528 (2008)), and nucleic acid-based expression inhibitors such as siRNAs and shRNAs (Cell Stem Cell, 3, 475-479 (2008)) against G9a], L-channel calcium agonist (e.g., Bayk8644) (Cell Stem Cell, 3, 568-574 (2008)), p53 inhibitor (e.g., siRNA and shRNA to p53, UTF1 (Cell Stem Cell, 3, 475-479 (2008)), Wnt Signaling (e.g., soluble Wnt3a) (Cell Stem Cell, 3, 132-135 (2008)), 2i/LIF (2i is inhibitor of mitogen-activated protein kinase signalling and glycogen synthase kinase-3, PloS Biology, 6(10), 2237-2247 (2008)) and the like. The nucleic acid-based expression inhibitors mentioned above may be in the form of expression vectors harboring a DNA that encodes an siRNA or shRNA.

Of the aforementioned constituents of nuclear reprogramming substances, SV40 large T, for example, can also be included in the scope of iPS cell establishment efficiency improvers because it is an auxiliary factor unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances or iPS cell establishment efficiency improvers. Hence, because the somatic cell nuclear reprogramming process is taken as an overall event resulting from contact of a nuclear reprogramming substance and an iPS cell establishment efficiency improver with a somatic cell, it does not always seems to be essential for those skilled in the art to distinguish between the two.

An iPS cell establishment efficiency improver can be contacted with a somatic cell as mentioned above for each of (a) when the substance is a proteinous factor and (b) when the substance is a nucleic acid encoding the proteinous factor, or (c) when the substance is a low-molecular-weight compound.

An iPS cell establishment efficiency improver may be contacted with a somatic cell simultaneously with a nuclear reprogramming substance, and either one may be contacted in advance, as far as the iPS cell establishment efficiency from a somatic cell improves significantly compared with the efficiency obtained in the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, for example, when the nuclear reprogramming substance and iPS cell establishment efficiency improver are both used in the form of a viral vector or plasmid vector, both may be simultaneously transferred into the cell.

(e) Improving the Establishment Efficiency by Culture Conditions

The iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

While any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). The start time may be before or after the somatic cell is contacted with the nuclear reprogramming substance, or at the same time as the contact, or after the contact, it is preferable, for example, that the culture under hypoxic conditions be started just after the somatic cell is contacted with the nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, for 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

After contacting a nuclear reprogramming substance (and iPS cell establishment efficiency improving substance), for example, 10-15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for primate ES cell (culture medium for primate ES/iPS cell, Reprocell), serum-free medium (mTeSR, Stemcell Technologies)] and the like.

Examples of the culture method include contacting a somatic cell with a reprogramming factor on 10% FBS-containing DMEM or DMEM/F12 culture medium at 37° C. in the presence of 5% $CO_2$ and culturing for about 4-7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby iPS-like colonies can be obtained after about 30-about 45 days or longer from the contact.

Alternatively, the cells are cultured on feeder cells (e.g., mitomycin C-treated STO cells, SNL cells etc.) at 37° C. in the presence of 5% $CO_2$ in a 10% FBS-containing DMEM culture medium (which can further contain LIF, penicillin/streptomycin, puromycin, L-glutamine, nonessential amino acids, β-mercaptoethanol and the like as appropriate), whereby ES-like colonies can be obtained after about 25-about 30 days or longer. Desirably, a method using a somatic cell itself to be reprogrammed, instead of the feeder cells (Takahashi K, et al. (2009), PLoS One. 4:e8067 or WO2010/137746), or an extracellular substrate (e.g., Laminin-5 (WO2009/123349) and Matrigel (BD)).

A candidate colony of iPS cells can be selected in two ways: methods with drug resistance and reporter activity as indicators, and methods based on macroscopic examination of morphology. As an example of the former, a colony positive for drug resistance and/or reporter activity is selected using a recombinant cell wherein the locus of a gene highly expressed specifically in pluripotenT cells (e.g., Fbx15, Nanog, Oct3/4 and the like, preferably Nanog or Oct3/4) is targeted by a drug resistance gene and/or a reporter gene. Examples of such recombinan T cells include MEFs derived from a mouse having the βgeo (which encodes a fusion protein of β-galactosidase and neomycin phosphotransferase) gene knocked in to the Fbx15 gene locus [Takahashi & Yamanaka, Cell, 126, 663-676 (2006)], and MEFs derived from a transgenic mouse having the green fluorescent protein (GFP) gene and the puromycin resistance gene integrated in the Nanog gene locus [Okita et al., Nature, 448, 313-317 (2007)]. On the other hand, methods for selecting a candidate colony by macroscopic examination of morphology include, for example, the method described by Takahashi et al. in Cell, 131, 861-872 (2007). Although the methods using reporter cells are convenient and efficient, colony selection by macroscopic examination is desirable from the viewpoint of safety when iPS cells are prepared for therapeutic purposes in humans. When 3 factors of Oct3/4, Klf4 and Sox2 are used as the nuclear reprogramming substance, the number of the established clones decreases, but almost all resulting colonies are iPS cells having high quality comparable to that of ES cell. Therefore, iPS cell can be established efficiently even without using a reporter cell.

The identity of the cells of the selected colony as iPS cells can be confirmed by positive responses to Nanog (or Oct3/4) reporters (puromycin resistance, GFP positivity and the like), as well as by the visible formation of an ES cell-like colony, as described above; however, to ensure greater accuracy, it is possible to perform tests such as analyzing the expression of various ES-cell-specific genes, and transplanting the selected cells to a mouse and confirming teratoma formation.

The human pluripotent stem cells obtained by the aforementioned method and cultured using feeder cells and serum show diversity, and therefore, are desirably cultured under restricted culture conditions. Such serum-free and feeder-free conditions include, for example, the method described in Nakagawa M, et al., Sci Rep. 4, 3594, 2014 and the like, and a method including culturing on an extracellular substrate (e.g., laminin5 (WO 2009/123349), laminin5 fragment (e.g., Laminin-5E8 (Nippi. Inc.)) and Matrigel (BD)) in a serum-free medium (e.g., mTeSR (Stemcell Technology), Essential 8 (Life Technologies) and StemFit (Ajinomoto Co., Inc.)).

(2) Differentiation Induction from Human Pluripotent Stem Cell into Mesoderm-Like Cell (Step I))

Examples of the basic medium for differentiation induction which is used in step I) include, but are not limited to, Neurobasal medium, Neural Progenitor Basal medium, NS-A medium, BME medium, BGJb medium, CMRL 1066 medium, minimum essential medium (MEM), Eagle MEM medium, aMEM medium, Dulbecco's modified Eagle medium (DMEM), Glasgow MEM medium, Improved MEM Zinc Option medium, IMDM medium, Medium 199 medium, DMEM/F12 medium, ham medium, RPMI 1640 medium, Fischer's medium, and a mixed medium of these and the like.

The medium may be a serum-containing medium or serum-free medium. Preferably, a serum-free medium is used. The serum-free medium (SFM) means a medium free of an untreated or unpurified serum, and therefore, a medium containing purified blood-derived component or animal tissue-derived component (growth factor and the like) can be mentioned. The concentration of the serum (e.g., fetal bovine serum (FBS), human serum and the like) may be 0-20%, preferably 0-5%, more preferably 0-2%, most preferably 0% (that is, serum-free). SFM may or may not contain an optional serum replacement. Examples of the serum replacement include albumin (e.g., lipid-rich albumin, albumin substitute recombinant albumin and the like, plant starch, dextran and protein hydrolysate etc.), transferrin (or other iron transporter), fatty acid, insulin, collagen precursor, trace element, 2-mercaptoethanol, 3'-thioglycerol or a substance containing an equivalent of these and the like as appropriate. Such serum replacement can be prepared, for example, by the method described in WO 98/30679. To simplify more, a commercially available product can be utilized. Examples of such commercially available substance include Knockout (trade mark) Serum Replacement (KSR), Chemically-defined Lipid concentrated, and Glutamax (Invitorogen).

The medium may contain other additives known per se. The additive is not particularly limited as long as mesoderm-like cell equivalent to epiblast cell before intestinal invagination is produced by the method of the present invention. For example, growth factors (e.g., insulin and the like), polyamines (e.g., putrescine and the like), minerals (e.g., sodium selenite and the like), saccharides (e.g., glucose and the like), organic acids (e.g., pyruvic acid, lactic acid and the like), amino acids (e.g., non-essential amino acid (NEAA), L-glutamine and the like), reducing agents (e.g., 2-mercaptoethanol and the like), vitamins (e.g., ascorbic acid, d-biotin and the like), steroids (e.g., [beta]-estradiol, progesterone and the like), antibiotics (e.g., streptomycin, penicillin, gentamicin and the like), buffering agents (e.g., HEPES and the like), nutrition additives (e.g., B27 supplement, N2 supplement, StemPro-Nutrient Supplement and the like) can be mentioned. Each additive is preferably contained in a concentration range known per se.

The medium for differentiation induction of human pluripotent stem cells into mesoderm-like cells contains a basal medium and activin A and a GSK-3β inhibitor as essential additives.

The concentration of activin A in the medium for differentiation induction is, for example, not less than about 5 ng/ml, preferably not less than about 10 ng/ml, more preferably not less than about 15 ng/ml and, for example, not more than about 40 ng/ml, preferably not more than about 30 ng/ml, more preferably not more than 25 ng/ml.

In the present invention, the GSK-3β inhibitor is defined as a substance that inhibits kinase activity of GSK-3β protein (e.g., phosphorylation capacity against β catenin), and many are already known. Examples thereof include lithium chloride (LiCl) first found as a GSK-3β inhibitor, BIO, which is an indirubin derivative (alias, GSK-3β inhibitor IX; 6-bromo indirubin 3'-oxime), SB216763 which is a maleimide derivative (3-(2,4-dichlorophenyl)-4-(1-methyl-1H-indol-3-yl)-1H-pyrrole-2,5-dione), GSK-3β inhibitor VII which is a phenyl α-bromomethyl ketone compound (4-dibromoacetophenone), L803-mts which is a cell membrane-permeable type-phosphorylated peptide (alias, GSK-3β peptide inhibitor; Myr-N-GKEAPPAPPQSpP-NH$_2$) and CHIR99021 having high selectivity (6-[2-[4-(2,4-Dichlorophenyl)-5-(4-methyl-1H-imidazol-2-yl)pyrimidin-2-ylamino]ethylamino]pyridine-3-carbonitrile). These compounds are commercially available from, for example, Calbiochem, Biomol and the like, and can be easily utilized. They may be obtained from other sources, or may be directly produced.

The GSK-3β inhibitor used in step I) can preferably be CHIR99021.

The concentration of CHIR99021 in the medium is, though not particularly limited to, for example, 0.1 µM-50 µM is preferable, for example, 1 µM, 2 µM, 3 µM, 4 µM, 5 µM, 6 µM, 7 µM, 8 µM, 9 µM, 10 µM or a concentration not less than these. Preferably, a concentration higher than the concentration 1 µM of a drug generally used for inhibition of GSK-3β is used, and it is more preferably not less than 3 µM.

In consideration of the subsequent induction step (step II)) into PGC-like cell, the medium is preferably free of basic fibroblast growth factor (bFGF) and bone morphogenic protein (BMP).

The medium preferably further contains a fibroblast growth factor receptor (FGFR) inhibitor.

In the present invention, the FGFR inhibitor is not particularly limited as long as it is a drug inhibiting binding of FGF receptor and FGF or signal transduction occurring after the binding. For example, PD173074 or BGJ398 can be mentioned.

When PD173074 is used, the concentration in the medium is not particularly limited. It is preferably 1 nM-50 nM, for example, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 25 nM, 30 nM, 35 nM, 40 nM, 45 nM, 50 nM, more preferably 25 nM.

The medium preferably further contains KSR. KSR present in an effective concentration range remarkably increases induction efficiency of mesoderm-like cell. The concentration of KSR is, for example, 5%, 10%, 15%, 20% or above, more preferably 15%.

In culturing here, the medium preferably further contains a ROCK inhibitor to suppress apoptosis during separation of human pluripotent stem cells into single cells. The ROCK inhibitor is not particularly limited as long as it can suppress function of the Rho kinase (ROCK). For example, Y-27632 may be preferably used in the present invention.

The concentration of Y-27632 in the medium is, though not particularly limited to, preferably 1 µM-50 µM, for example, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 25 µM, 30 µM, 35 µM, 40 µM, 45 µM, 50 µM, more preferably 10 µM.

An incubator used for inducing pluripotent stem cells into mesoderm-like cells is not particularly limited, and flask, tissue culture flask, dish, petri dish, tissue culture dish, multidish, microplate, microwell plate, multiplate, multiwell plate, microslide, chamber slide, petri dish, tube, tray, culture bag, and roller bottle can be mentioned. The incubator may be cell adhesive. A cell adhesive incubator may be coated with any cell adhesion substrate such as extracellular matrix (ECM) and the like for the purpose of improving adhesiveness of the incubator surface to the cells. The cell adhesion substrate may be any substance aiming at adhesion of pluripotent stem cells or feeder cells (when used). As the cell adhesion substrate, collagen, gelatin, poly-L-lysine, poly-D-lysine, poly-L-ornithine, laminin, and fibronectin and a mixture thereof, such as Matrigel and lysed cellular membrane preparations can be mentioned. More preferred is an incubator coated with fibronectin.

For culturing, human pluripotent stem cells are seeded on the above-mentioned incubator to a cell density of, for example, about $10^4$-$10^5$ cells/cm$^2$, preferably about 2-6×$10^4$ cells/cm$^2$, and cultured under an atmosphere of 1-10% CO$_2$/99-90% air in an incubator at about 30-40° C., preferably about 37° C., for less than 60 hr, preferably 42 hr (e.g., error of ±2 hr is tolerable).

The fact of differentiation into mesoderm-like cells can be confirmed, for example, by analyzing the expression level of the marker gene of mesoderm-like cell and/or pluripotent stem cell by RT-PCR. Mesoderm-like cells are defined as cells having either or both of the following properties:

(1) an increase in at least one gene expression selected from T, EOMES (Eomesodermin), EVX1 (Even-Skipped Homeobox 1), SP5 (Sp5 transcription factor), MIXL1 (Mix Paired-Like Homeobox 1) and NODAL, compared to pluripotent stem cell before differentiation induction, (2) a decrease in at least one gene expression selected from POU5F1 (POU domain, class 5, transcription factor 1), NANOG and SOX2 (SRY (Sex Determining Region Y)-Box 2), compared to pluripotent stem cell before differentiation induction.

As mentioned above, the medium for differentiation induction into mesoderm-like cell contains activin A and a GSK3β inhibitor. Therefore, the present invention also provides a reagent kit for differentiation induction of pluripotent stem cells into mesoderm-like cells, which contains activin A and a GSK3β inhibitor. These components may be provided in the form of being dissolved in water or a suitable buffer, provided as a freeze-dry powder and can also be used upon dissolution in a suitable solvent when in use. Also, these components may be placed in a kit each as a single reagent, or two or more kinds thereof may be mixed and provided as a single reagent as long as they do not adversely influence each other.

(3) Differentiation Induction of Mesoderm-Like Cell into Human PGC-Like Cell (Step II))

Differentiation of the thus-obtained mesoderm-like cells into PGC-like cells can be induced by culturing in the presence of BMP. Therefore, a second aspect of the present invention relates to a method for producing human PGC-like cells from human pluripotent stem cells via mesoderm-like cells obtained by the method of the above-mentioned (2). Therefore, the method for inducing differentiation of human pluripotent stem cells into human PGC-like cells of the present invention includes I) a step of producing mesoderm-like cells from human pluripotent stem cells according to any method described in the above-mentioned (2); and II) a step of culturing the mesoderm-like cells obtained in step I) in the presence of BMP.

The basal medium for differentiation induction of human PGC-like cells in step II), the basal medium exemplified to be used in step I) is preferably used in the same manner.

The medium may be a serum-containing medium or serum-free medium (SFM). Preferably, a serum-free medium is used. The medium preferably further contains KSR. KSR present in an effective concentration range remarkably increases induction efficiency of mesoderm-like cell. The concentration of KSR is, for example, 5%, 10%, 15%, 20% or above, more preferably 15%.

BMP used as an essential additive for the medium for differentiation induction of mesoderm-like cells into PGC-like cells is BMP2, BMP4 or BMP7. A more preferable BMP is BMP 2 or BMP 4. The concentration of BMP is, for example, not less than about 100 ng/ml, not less than about 200 ng/ml, not less than about 300 ng/ml, not less than about 400 ng/ml.

The medium for differentiation induction into PGC-like cells preferably further contains at least one cytokine selected from the group consisting of stem cell factor (SCF), epithelial cell growth factor (EGF) and leukemia inhibitory factor (LIF) as an additive.

The concentration of SCF is, for example, not less than about 50 ng/ml, not less than about 100 ng/ml, not less than about 200 ng/ml, not less than about 300 ng/ml, more preferably 100 ng/ml.

The concentration of LIF is, for example, not less than about 300 U/ml, not less than about 500 U/ml, not less than about 800 U/ml, or not less than about 1000 U/ml, more preferably 1,000 U/ml.

The concentration of SCF is, for example, not less than about 30 ng/ml, not less than about 50 ng/ml, not less than about 80 ng/ml, not less than about 100 ng/ml, more preferably 100 ng/ml.

The concentration of EGF is, for example, not less than about 10 ng/ml, not less than about 20 ng/ml, not less than about 30 ng/ml, not less than about 40 ng/ml, not less than about 50 ng/ml, more preferably 50 ng/ml.

In culturing in step II), the medium preferably further contains a ROCK inhibitor to suppress apoptosis during separation of mesoderm-like cells into single cells. As the ROCK inhibitor, one which is the same as the above is used.

For culturing, mesoderm-like cells are seeded in a cell non-adhesive or low adhesive incubator known per se to a cell density of, for example, about $1-50 \times 10^3$ cells/cm$^2$, preferably about $5-20 \times 10^3$ cells/cm$^2$, and cultured under an atmosphere of 1-10% $CO_2$/99-90% air in an incubator at about 30-40° C., preferably about 37° C., for about 4-10 days, preferably 4-8 days, more preferably about 6 days (e.g., 144±12 hr, preferably 144±6 hr).

The fact of differentiation into PGC-like cells can be confirmed, for example, by analyzing the expression of BLIMP1 by RT-PCR and the like. Where necessary, expression of other gene and cellular surface antigen can also be examined. As other gene, TFAP2C can be mentioned. When pluripotent stem cells having a fluorescence protein gene under control of BLIMP1- and/or TFAP2C-promoter is used as a starting material, the fact of differentiation into PGC-like cells can be confirmed by FACS analysis. When pluripotent stem cells derived from human or other non-mouse mammal such as ESC or iPSC and the like do not have an appropriate transgenic reporter, the fact of differentiation into PGC-like cells is preferable confirmed by FACS analysis and the like using one or more kinds of cellular surface antigens specifically expressed in PGC-like cells. Examples of the cellular surface antigen include at least one marker gene selected from the group consisting of PECAM (CD31), INTEGRINα6 (CD49f), INTEGRINβ3 (CD61), KIT (CD117), EpCAM, PODOPLANIN and TRA1-81, with preference given to INTEGRINα6 (CD49f) and EpCAM.

To isolate PGC-like cell, it is preferable to further perform, as step III), a step of selecting a cell positive to the aforementioned cellular surface antigen from the cells obtained in the aforementioned step II).

Isolation of PGC-like cell can be performed by a method known per se. For example, isolation of PGC-like cell may be performed by cell sorting using an antibody to the cellular surface antigen described above.

As mentioned above, in a preferable embodiment, the medium for differentiation induction of mesoderm-like cells into PGC-like cells contains BMP. Therefore, the present invention also provides a reagent kit containing BMP for differentiation induction of mesoderm-like cells into PGC-like cells. These components may be provided in the form of being dissolved in water or a suitable buffer, provided as a freeze-dry powder and can also be used upon dissolution in a suitable solvent when in use. Also, these components may be placed in a kit each as a single reagent, or two or more kinds thereof may be mixed and provided as a single reagent as long as they do not adversely influence each other.

Assuming isolation of PGC-like cells, the reagent kit for differentiation induction may contain an antibody to the aforementioned cellular surface antigen.

(4) Cell Population Containing Pluripotent Stem Cell-Derived PGC-Like Cells Via Mesoderm-Like Cell The present invention also provides a cell population containing pluripotent stem cell-derived PGC-like cells, which is produced by the aforementioned steps I) and II). The cell population is preferably a purified population of PGC-like cells, and preferably a cell population purified by the aforementioned step III).

While the present invention is more specifically explained by referring to the following Examples, it is needless to say that the present invention is not limited thereby.

EXAMPLES

Experiment Method

Ethical Guidelines

All animal experiments were performed according to the ethical guidelines of Kyoto University and Siga University of Medical Science. The induction experiments from hiPSCs into hPGCLCs were approved by the Kyoto University Institutional Review Board (Institutional Ethics Committee).

Culture of hiPSCs hiPSC strains (201B7, 585A1, 585B1) (Takahashi K, et al., Cell. 131, 861-872, 2007 and Okita K, et al., Stem Cells. 31, 458-466, 2013) were subjected to maintenance culture under mitomycin C (MMC)-treated SNL feeder cell by a conventional method [Dulbecco's Modified Eagle Medium (DMEM/F12; Life Technologies) added with 20% (v/v) Knockout Serum Replacement (KSR; Life Technologies), 1% GlutaMax (Life Technologies), 0.1 mM non-essential amino acid, 4 ng/ml recombinant human bFGF (Wako), and 0.1 mM 2-mercaptoethanol], and then adapted to feeder-free conditions [on recombinant laminin511 (rLN511E8) (iMatrix-511, Nippi)-coated cell culture plate, StemFit™ (Ajinomoto, Tokyo, Japan) medium] (Nakagawa M, et al., Sci Rep. 4, 3594, 2014). To separate the cells to single cells for passage culture and differentiation induction, the cells were treated with a 1:1 mixed solution of TrypLE Select (Life Technologies) and 0.5 mM EDTA/PBS, and 10 µM ROCK inhibitor (Y-27632; Wako Pure Chemical Industries) was added for 24 hr after seeding.

Production of BTAG Knockin Reporter Strain

For construction of a donor vector for isolating BLIMP1-p2A-tdTomato (hereinafter BT) or TFAP2C-p2A-eGFP (hereinafter AG) knockin hiPSC strains, the homology arm of BLIMP1 [left (5-prime)arm: 1148 bp; right (3-prime)arm: 1192 bp] and the homology arm of TFAP2C [left arm: 1144 bp; right arm: 1162 bp] were amplified by PCR and subcloned to pCR2.1 vector (TOPO TA Cloning; Life Technologies). p2A-tdTomato fragment or p2A-eGFP fragment respectively having PGK-Neo cassette or PGK-Puro cassette each having adjacent loxP moiety was amplified by PCR and, using GeneArt Seamless Cloning & Assembly Kit (Life Technologies), inserted into the 3'-terminal of BLIMP1 coding sequence or TFAP2C coding sequence of the above-mentioned subclone vector containing a homology arm. Then, MC1-DT-A-polyA cassette was introduced into the downstream of the right (3') homology arm of BLIMP1-p2A-tdTomato donor vector or TFAP2C-p2A-eGFP donor vector by restriction enzyme NotI/XbaI or SacI/KpnI.

TALEN sequence targeting a sequence adjacent to the stop codon of BLIMP1 and TFAP2C was produced using GoldenGate TALEN and TAL Effector kit (Addgene, #1000000016). The RVD sequences of TALEN are described below;

```
BLIMP1-left (5-prime), NN NN NG NI HD HD NG NN NG
NI NI NI NN NN NG HD NI NI NI;
BLIMP1-right (3-prime), HD NG NG NI NI NN NN NI NG
HD HD NI NG NG NN NN NG NG HD;
TFAP2C-left, NN NN NI NN NI NI NT HD NI HD NI NN
NN NI NI NI NG;
TFAP2C-right, NI HD NG HD NG HD HD NG NI NI HD HD
NG NG NG HD NG.
```

The TALEN activity was evaluated by SSA assay (FIG. 8A) (Sakuma T, et al., Genes Cells. 18, 315-326, 2013). As the control in this evaluation, pGL4-SSA empty reporter plasmid, pGL4-SSA-HPRT1 reporter plasmid, and TALEN pair targeting human HPRT1 were used.

Using NEPA21 type II (Nepa gene), BLIMP1-p2A-tdTomato donor vector or TFAP2C-p2A-eGFP donor vector (5 µg) and TALEN plasmid (2.5 µg each) were introduced into hiPSCs (585A1 or 585B1) by electroporation. About 12 days later, a single colony was isolated, and whether it was targeting integration or random integration was evaluated by PCR of extraction genome DNA. To exclude indel mutation, untargeted allele (Non-targeted alleles) was further screened by the Sanger sequence method. To remove PGK-Neo cassette and PGK-Puro cassette, a plasmid expressing Cre recombinase was transfected into a strain having an insertion targeting both BLIMP1 and TFAP2C gene locus.

Differentiation Induction into Endoderm or Trophectoderm

Aiming at endoderm differentiation, hiPSCs having BLIMP1-p2A-tdTomato knockin gene locus or TFAP2C-p2A-eGFP knockin gene locus were seeded in iMatrix-511 coating plate and cultured in RPMI1640 (Wako Pure Chemical Industries) containing 2% B27 (Life Technologies), 100 ng/ml activin A (Peprotech, #120-14), and 3 µM CHIR99021 (Biovision, #1677-5). Aiming at differentiation into trophectoderm, iPSCs were seeded in iMatrix-511 (Nippi, 892001)-coating plate and cultured in bFGF-free StemFit™ (Human-Zyme, #HZ-1078) containing 10 ng/ml BMP4.

Production of BLIMP-Knockin/Knockout hiPSCs

For construction of donor vector isolating BLIMP1-p2A-tdTomato; BLIMP1$^{-/-}$ knockin/knockout hiPSC strain, a homology arm adjacent BLIMP1 exon 4 [left (5-prime)arm: 1517 bp; right (3-prime)arm: 1446 bp] was amplified by PCR, and subcloned to pCR2.1 vector. 2A-tdTomato-SV40 polyA fragment having PGK-Neo cassette adjacent to LoxP site was amplified by PCR. Then, using GeneArt Seamless Cloning & Assembly Kit, additional 30 bp sequence of intron 4 was inserted instead of exon4 analogue. Next, MC1-DT-A-polyA cassette was introduced into the downstream of right (3'-terminal) homology arm by using restriction enzymes XhoI and SacI.

TALEN construct having the RVD sequence shown below and targeting BLIMP1 exon 4 was produced by the aforementioned method;

```
left (5-prime), HD NI HD HD NI HD NG NG HD NI NG
NG NN NI HD NN NN HD;
right (3-prime), NI NN HD NN HD NI NG HD HD NI NN
NG NG NN HD NG NG NG.
```

Figure 14:
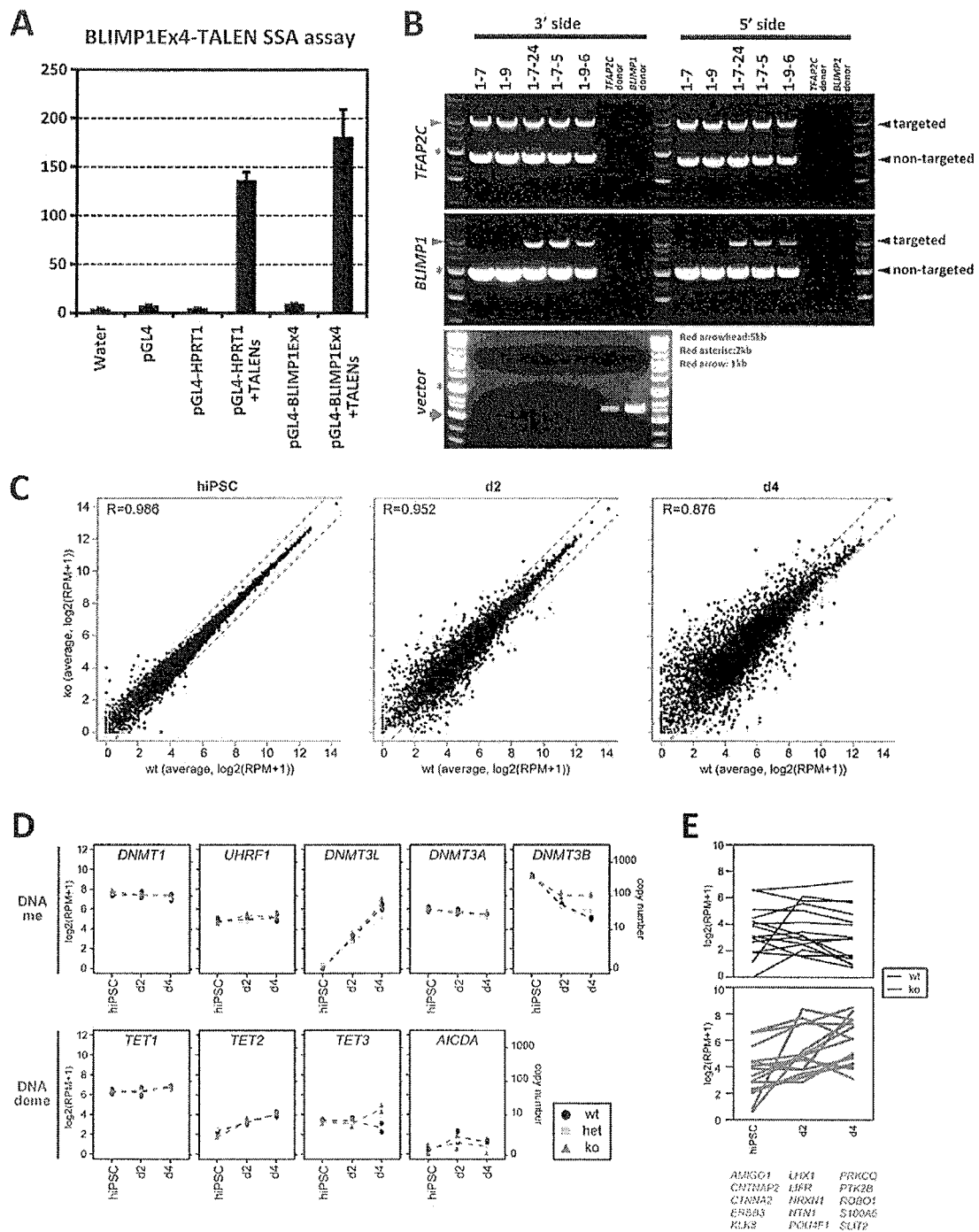
FIG. 14 shows production results of the BLIMP1 knockout cell line.

The TALEN activity was evaluated by SSA assay (FIG. 14A). For isolation of BTAG; BLIMP1$^{+/-}$ and BTAG; BLIMP1$^{-/-}$ hiPSCs strains, the aforementioned donor vector (5 µg) and TALEN plasmid (each 2.5 µg) were introduced into TFAP2C-p2A-eGFP (AG) knockin hiPSC strain. The success of random targeting unaccompanied by integration was evaluated by PCR of extracted genome DNA. Untargeted allele was further evaluated by Sanger sequence method, assuming presence (BTAG; BLIMP1$^{-/-}$) or absence (BTAG; BLIMP1$^{+/-}$) of frameshift indel mutation.

Karyotype Classification and Gband Analysis hiPSCs were incubated in 100 ng/ml demecolcine-containing medium for 8 hr. After separation with Accutase (Sigma-Aldrich), and the cells were treated with hypotonic buffer (Genial Genetics, GGS-JL006b) warmed in advance and incubated at 37° C. for 30 min. Then, the cells were fixed with Carnoy's solution (3:1 mixture of methanol and acetic acid), and added dropwise on a glass slide on paper sheet immersed in water. Chromosomes fluorescenced by DAPI staining were counted to determine karyotype. G band analysis was performed by Nihon Gene Research Laboratoryies Inc. (Sendai, Japan).

Induction of iMeLCs and hPGCLCs

Initial mesoderm-like cells (iMeLCs) were induced by seeding hiPSCs maintained in StemFit™ in a 12 well plate coated with human plasma fibronectin (Millipore, FC010) at 1.0-2.0×10$^5$ cells per well in GK15 medium [GMEM containing 15% KSR, 0.1 mM NEAA, 2 mM L-glutamine, 1 mM sodium pyruvate and 0.1 mM 2-mercaptoethanol (Life Technologies)] containing 50 ng/ml activin A, 3 µM CHIR99021 and 10 µM ROCK inhibitor (Y-27632; Wako Pure Chemical Industries). The hiPSCs were induced by seeding in a low-cell-binding V-bottom 96 wellplate (Thermo, 81100574) at 3.0×10$^3$ cells per well in GK15 added with 1000 U/ml LIF (Millipore, #LIF1005), 200 ng/ml BMP 4,100 ng/ml SCF (R&D Systems, 455-MC), 50 ng/ml EGF (R&D Systems, 236-EG), and 10 µM ROCK inhibitor. For investigation of conditions and induction of iMeLCs or hPGCLC, PD173074 (StemGent, #04-0008) or LDN193189 (StemGent, #04-0074) was respectively added. Other than the above, WNT3A (R&D Systems, 5036-WN) was used instead of CHIR99021, and BMP2 (R&D Systems, 355-BM), BMP7 (R&D Systems, 354-BP), or BMP8A (R&D Systems, 1073-BP) was used instead of BMP4.

FACS Analysis

Floating aggregates containing hPGCLCs were separated by treating with 0.05% Trypsin-EDTA/PBS at 37° C. for 10 min. After washing with PBS containing FBS and 0.1%

BSA, the cell suspension was filtered by a cell strainer (BD Biosciences) and centrifuged to remove cell aggregates. The collected cells were suspended in FACS buffer (0.1% BSA in PBS) and analyzed by a flow cytometer (ARIA III; BD Biosciences). For the analysis of hPGCLCs or hiPSCs, the separated cells were stained with APC-conjugated anti-human CD326 (EpCAM), BV421-conjugated anti-human/mouse CD49f, PE-conjugated anti-TRA-1-60, or FITC-conjugated anti-SSEA-4. Furthermore, intracellular staining using Alexa fluor 647-conjugated anti-OCT3/4, Alexa Fluor 647-conjugated anti-NANOG or V450-conjugated anti-SOX2 was performed using BD cytofix/Cytoferm Fixation/Permeabilization kit (BD, 554714) and according to the Manufacturer's instructions. The antibodies used are shown in Table 1.

TABLE 1

| Antibody | Supplier | Catalogue# |
|---|---|---|
| APC-conjugated anti-CD326 | BioLegend | 324207 |
| Alexa Fluor 647-conjugated anti-OCT3/4 | BD Pharmingen | 560329 |
| Alexa Fluor 647-conjugated anti-NANOG | BD Pharmingen | 561300 |
| BV421-conjugated anti-CD49f | BioLegend | 313623 |
| FITC-conjugated anti-SSEA-4 | BD Pharmingen | 560126 |
| PE-conjugated anti-TRA-1-60 | BD Pharmingen | 560193 |
| V450-conjugated anti-SOX2 | BD Horizon | 561610 |

Preparation of Single Cell cDNA from cyESCs and cyPGCs cyESCs (CMK9) (*Macaca fascicularis* ES cell) were obtained from Dr. Suemori (Fujioka T, et al., Int J Dev Biol. 48, 1149-1154, 2004 and; Suemori H, et al., Dev Dyn. 222, 273-279, 2001) and cultured together with mouse fetal feeder cells (mouse embryonic feeders (MEFs)) in hESC medium [DMEM/FI2 (Life Technologies) added with 20% (vol/vol) KSR (Life Technologies), 1 mM sodium pyruvate (Life Technologies, 2 mM GlutaMax (Life Technologies), 0.1 mM non-essential amino acid (Life Technologies), 0.1 mM 2-mercaptoethanol (Sigma-Aldrich), 1000 U/mL ESGRO mouse LIF (Millipore), 4 ng/ml recombinant human bFGF (Wako Pure Chemical Industries)] in a conventional method. For SC3-seq analysis (Nakamura T, et al., Nucleic Acids Res. 43, e60. 2015), the cells were treated with CTK solution [0.25% trypsin (Life Technologies), 0.1 mg/mL of collagenase IV (Life Technologies), 1 mM $CaCl_2$ (Nacalai Tesque)], incubate at 37° C. for about 10 min and in 0.25% trypsin/PBS (Sigma-Aldrich) at 37° C. for about 10 min. Thereafter, the cells were dispersed in 1% (vol/vol) KSR/PBS to give single cells.

In *Macaca fascicularis*, ovumrecovery, intracytoplasm spermatozoon injection (ICSI), preimplantation embryo culture, and transplantation of preimplantation embryo to individual were performed according to conventional methods (Yamasaki J, et al., Theriogenology. 76, 33-38, 2011). The transferred embryos were monitored by ultrasonication diagnosis, and removed by caesarean section on embryonic days 43, 50 and 51. The gender of the embryo was determined by sex specific PCR of genome DNA isolated from the somatic cell tissue (Wilson and Erlandsson, Biol Chem. 379, 1287-1288, 1998). The genital ridge was incised, separated into single cells in 0.25% trypsin/PBS at 37° C. for about 10 min, and pipetting was repeated. The obtained single cells were dispersed in 0.1 mg/ml PVA/PBS (Sigma-Aldrich) and subjected to SC3-seq analysis.

Q-PCR and RNA-seq Analysis

RNA extraction for PCR was performed using RNeasy Micro Kit (QIAGEN) and according to the Manufacturer's instructions. cDNA synthesis and amplification using 1 ng of purified total RNA, and construction of cDNA library for RNA sequence were performed according to the method described in Nakamura T, et al., Nucleic Acids Res. 43, e60. 2015. Q-PCR was performed by measuring Power SYBR Green PCR Master mix (Life Technologies) along with amplified cDNA by using CFX384 real-time qPCR system (Bio-Rad). The gene expression level was evaluated by culculating $\Delta C_t$ (log 2 scale) normalized to average $\Delta C_t$ values of PPIA and ARBP. The primers used are shown in Table 2 (human gene) and Table 3 (*Macaca fascicularis* gene).

TABLE 2-1

| Gene | Forward primer | Reverse primer |
|---|---|---|
| BLIMP1 | AAACCAAAGCATCACGTTGACA | GGATGGATGGTGAGAGAAGCAA |
| TFAP2C | ATTAAGAGGATGCTGGGCTCTG | CACTGTACTGCACACTCACCTT |
| NANOS3 | TGGCAAGGGAAGAGCTGAAATC | TTATTGAGGGCTGACTGGATGC |
| DAZL | TGGCCCTTCTTTCAGTGACTTC | GACCCTAGGGGGCACTAGTAA |
| DPPA3 | AAGCCCAAAGTCAGTGAGATGA | GCTATAGCCCAACTACCTAATGC |
| DDX4 | TTCTTCACAAGCTCCCAATCCA | TTCTTCTCTGCATCAAAACCACA |
| ZFP42 | CCAGACTGGATAACAGCAAGAGC | TGCAAATTTTTCATTCTCTAGGGC |
| PRDM14 | TATCATACTGTGCACTTGGCAGAA | AGCAACTGGGACTACAGGTTTGT |
| KLF2 | ACTAGAGGATCGAGGCTTGTGA | TGCCCACCTGTCTCTCTATGTA |
| KLF4 | AGCCTAAATGATGGTGCTTGGT | CCTTGTCAAAGTATGCAGCAGT |
| TCL1B | CAAATCCCCTTCATACCCACCA | TGCCATCTCTTAAACCGAACCA |
| TFCP2L1 | AGCTCAAAGTTGTCCTACTGCC | TTCTAACCCAAGCACAGATCCC |
| ESRRB | TAAAATGGCAGTTCCCCATTGC | CCAGATACATGGGACCAGGATG |
| POU5F1 | CTGTCTCCGTCACCACTCTG | AAACCCTGGCACAAACTCCA |

TABLE 2-1-continued

| Gene | Forward primer | Reverse primer |
|---|---|---|
| NANOG | AGAGGTCTCGTATTTGCTGCAT | AAACACTCGGTGAAATCAGGGT |
| SOX2 | TGAATCAGTCTGCCGAGAATCC | TCTCAAACTGTGCATAATGGAGT |
| SOX15 | TTTTAATCCAGCAGCATCCCCT | AATTGTATGTTGTGCGGCTCTC |
| SOX17 | TTCGTGTGCAAGCCTGAGAT | TAATATACCGCGGAGCTGGC |
| GATA4 | CCTCTTTCTCAGCAGAGCTGTA | CTCTGCTACAGCCAGTAGGATT |
| GATA6 | ACAGGGCGATTTCCTTTCAGTT | CTTCTGTTGGGGGTAACGTCTG |
| FOXA2 | ACCCGGTTTTATCCCTTGAATC | ATACAACCTGCAACCAGACAGG |
| MIXL1 | TGCTTTCAAAACACTCGAGGAC | GAGTGATCGAAGTAACAGGTGC |
| SP5 | GAGATTTGAAACAGTGCTCGGG | GGAGCTGAAGACAAAAGCAACA |
| BOMES | AAGGGGAGAGTTTCATCATCCC | GGCGCAAGAAGAGGATGAAATAG |
| NODAL | CATTGCCTCAGGCTGGGTTG GT | ACAGCTCATTAGCAGAGAACCA |
| T | AGCCAAAGACAATCAGCAGAAA | CACAAAAGGAGGGGCTTCACTA |
| EVX1 | CAAATCCTCACTCCCACACTCA | GAAGAACCACTCCCTCTCAGTC |
| GSC | GTCGAGAAAGAGGAACGAGGAG | AAATACTACGGTGGGGGCTAGT |
| MSX2 | GGCAGAAGGTAAAGCCATGTTT | TAAAGGTATACCGGAGGGAGGG |
| PAX6 | GCGGGTGACAAAATAGTTGTCTT | GCCAGGATGTCAAATCTCTCCA |
| SOX1 | GGCCAAGGTAACACTCATCGTA | ACCCTGTGATTTGGGAAGTGAA |
| DNMT3A | TGGGATTCATCCAGACTCATGC | AAAGTGAGAAACTGGGCCTGAA |

TABLE 2-2

| Gene | Forward primer | Reverse primer |
|---|---|---|
| DNMT3B | TAACTGGAGCCACGACGTAAC | GCATCCGTCATCTTTCAGCCTA |
| DNMT3L | AGCCATAAGGAGCAGGCACT | GGGGAGAAAGCAGTTCTTCACCA |
| HOXD1 | AGCTGCTTCAGTGATCTTCACA | ACCCATTCTGTGGATTTGTTCA |
| PPIA | TTGATCATTTGGTGTGTTGGGC | AAGACTGAGATGCACAAGTGGT |
| ARBP | GAAACTCTGCATTCTCGCTTCC | ACTCGTTTGTACCCGTTGATGA |
| ERCC 1806 | GATCCCGGAAGATACGCTCTAAG | CGCAGGTTGATGCTTCCAATAAA |
| ERCC 451.5 | CAGGCAAGAGTTCAATCGCTTAG | TAGCCTTCAGTGACTGTGAGATG |
| ERCC 56.4 | CCAACCCCACATTGTAACTTCG | GTCTTTACTTACGCGCTCCTCT |

TABLE 3

| Gene | Forward primer | Reverse primer |
|---|---|---|
| BLIMP1 | TTCCCAACTACTCGTTTGTTCTTTG | CATGTAAGAGGCAGAAAAAGGAAGG |
| TFAP2C | TCGGAGATCAAGTCCTCTGG | CCTTTGAACACGGGGTTTAG |
| PRDM14 | TGCCCTGTTGTTTTAGGACTGT | AACCAGCAGTTAAGGAAAGGCT |
| POU5F1 | GGGAGGAGCTAGGGAAAGAGAACCTA | CCCCCACCCGTTGTGTTCCCA |
| NANOG | TGTTCCGGTTTCCATTATGCC | TAGGCTCCAACCATACTCCA |
| GATA4 | CAAATCCCCTTCATACCCACCA | TGCCATCTCTTAAACCGAACCA |
| T | TGCTGTCCCAAGTGGCTTAC | CTGGACCCTGGCAAACATCT |

Reading of Mapping of RNA-Seq and Conversion to Gene Expression Level

Genome sequences [mouse GRCm38/mm10, human GRCh37/hg19, and *Macaca fascicularis* MacFas5.0] and transcript annotation (mouse ref_GRCm38, human ref_GRCh37, and *Macaca fascicularis* ref_MacFas5.0) were obtained from NCBI ftp site (ftp://ftp-trace.ncbi.nlm.nih.gov/genomes/Macaca_fascicularis).

Read trimming, mapping and expression level were evaluated according to the method described above (Nakamura T, et al., Nucleic Acids Res. 43, e60. 2015). Library adapter and poly-A sequence were eliminated by cut adapt-1.3. The reads smaller than 30 bp were eliminated. All remaining reads were mapped on the genome by using "no-coverage-search" option (Kim D, et al., Genome Biol. 14, R36, 2013) and utilizing ERCC spike-in RNAs (Life Technologies) accompanying top hat-1.4.1/bowtie1.0.1. The reads mapped on the genome from ERCC spike-in RNAs using Perl script were separated, and cufflinks-2.2.0 program (Trapnell C et al., Nat Biotechnol. 28, 511-515, 2010) was performed on ref_MacFas5.0 transcription annotation by using "compatible-hits-norm", "no-length-correction" and "library-type fr-secondstrand" options. All reference copies were extended by 10 Kb from the transcription termination site (TTSs) to correct insufficient annotation data (Nakamura T, et al., Nucleic Acids Res. 43, e60. 2015). All reads mapped on the ERCC spike-in RNA sequence were used for evaluation of the transcription copy number per cell. The expression level was normalized only for all mapping reads (RPM), and further analyzed by $\log_2(RPM+1)$.

Comparison of Gene Expression in Human, *Macaca fascicularis* and Mouse

For comparison of *Macaca fascicularis* gene and human gene, a one-to-one correspondence table of genes was made by genome genomic coordinate comparison. First, all human transcription annotations (ref_GRCh37 containing all exon data) were converted to genome gene loci of *Macaca fascicularis* by using LiftOver utility (https://genome.ucsc.edu/cgi-bin/hgLiftOver). The chain files used for LiftOver (hg19ToMacFas5.over.chain and macFas5ToHg19.over.chain) were obtained from http://hg-download-test.cse.ucsc.edu/goldenPath/. Then, human genome annotation at MacFas5.0 gene loci was compared with ref_MacFas5.0, and searches for gene locusting Mac-Fas5.0 transcription product were successively performed. The same method for ref_MacFas5.0 was performed, the transcription annotation at ref_MacFas5.0 was converted to hg19 gene loci by using LiftOver, and searches for gene locusting human transcription product were performed. The whole 17,932 genes were identified by two kinds of comparison to find a gene that definitely matches between human (24,968) and *Macaca fascicularis* gene (29,437). In human and mouse genes (ref_GRCm38,26,556 genes), the same comparison was performed, and 15,941 genes matched. Since KLF2 gene was not annotated by ref_MacFas5.0, annotation of this gene was added to ref_MacFas5.0 reference gff file in the corresponding region of human KLF2.

Transcriptome Analysis

To analyze specifically expressing genes, UHC analysis (R3.1.1 Euclidean distances and hclust function accompanying Ward distance function) and PCA analysis (R3.1.1 prcomp function) were used. In this case, genes showing maximum $\log_2$ (RPM+1) value of less than 4 were excluded. The genes (DEGs) specifically expressed in hPGCLC induction were selected based on P value of one-way Anova test (calculated by value function of false positive rate <0.01, R3.1.1) and fold changes of two sequential time point (>2). DEGs in BLIMP1$^{-/-}$ cell as compared with wild-type sample were selected based on the P value (<0.05) of the student t-test and fold change (>2). GO analysis was performed using DAVID web tool (Huang da W, et al., Nat Protoc. 4, 44-57, 2009). A heatmap was made using R3.1.1, gplotspackage, heatmap.2 function. For comparison of RNA-seq data and GSE30056 data (Affymetrix GeneChip Mouse Genome 430 2.0 Array), RNA-seq data of mESCs after normalization using the standard curve of the mESCs array data was calculated.

Immunofluorescence Analysis

For immunofluorescent staining of hPGCLCs, BTAG positive cells in the cell aggregates on day 8 of induction from BTAG 585B1-868 hiPSCs via iMeLC were selected by FACS, mixed with BTAG 585B1-868 hiPSCs at 1:1 ratio and spread on MAS-coated slide glass (Matsunami). The slide was fixed with 4% para-formaldehyde (PFA) for 15 min, and washed 3 times with PBS and once with PBST. After a permeation treatment with PBS containing 0.5% triton X at room temperature for 5 min, the slide was washed 3 times with PBS. Then, the slide was incubated in a blocking solution (5% normal goat serum, 0.2% tween 20, 1×PBS) at room temperature for 2 hr, and incubated at 4° C. overnight in the blocking solution added with the primary antibody. After washing 6 times with PBS, the slide was incubated in the blocking solution containing the secondary antibody and 1 μg/mL DAPI for 50 min. After washing 6 times with PBS, confocal laser scanning microscopic analysis (Olympus FV1000) was performed using Vectashield mounting medium (Vector Laboratories). For 5mC immunofluorescent staining, the slide was treated with 4N HCl/0.1% Triton X at room temperature for 10 min, washed twice with PBS and treated with the blocking solution. The primary antibody and secondary antibody used are described.

For immunofluorescent staining of cyPGCs, the genital ridge cut out from E50 (XX) embryo was fixed with 4% PFA/PBS for 15 min at room temperature. The tissue was continuously immersed in 10% and 30% sucrose/PBS, embedded in OCT compound (Sakura), freezed and a section with 10 um thickness was produced. The air-dried section was washed 3 times with PBS, and incubated in a blocking solution for 1 hr. The section was incubated with the primary antibody contained in the blocking solution at room temperature for 2 hr, and washed 4 times with PBS. Then, the section was incubated with the secondary antibody contained in the blocking solution at room temperature for 50 min, washed 4 times with PBS, and confocallaser scanning microscopic analysis was performed using Vectashield mounting medium. The antibodies used are shown in Table 4.

TABLE 4

| Antibody | Supplier | Catalogue# |
| --- | --- | --- |
| Mouse anti-BLIMP1 | R&D Systems | MAB36081 |
| Mouse anti-OCT3/4 | SantaCruz Biotechnology | sc-5379 |
| Mouse anti-SOX2 | R&D Systems | MAB2018 |
| Mouse anti-5 methylcytosine (5-mC) | Active Motif | 39649 |
| Rabbit anti-DDX4 | Abcam | ab13840 |
| Rabbit anti-H3K9Me2 | Millipore | 07-441 |
| Rabbit anti-H3K27Me3 | Millipore | 07-449 |
| Rabbit anti-TFAP2C SantaCruz | Biotechnology | sc-8977 |
| Goat anti-SOX17 | Neuromics | GT15094 |

TABLE 4-continued

| Antibody | Supplier | Catalogue# |
| --- | --- | --- |
| AlexaFluor 488 conjugated goat anti-rat IgG | Life Technologies | A11006 |
| AlexaFluor 488 conjugated goat anti-mouse IgG | Life Technologies | A11001 |
| AlexaFluor 568 conjugated goat anti-rabbit IgG | Life Technologies | A11011 |
| AlexaFluor 633 conjugated goat anti-rabbit IgG | Life Technologies | A21070 |
| AlexaFluor 633 conjugated goat anti-mouse IgG | Life Technologies | A21052 |

Example 1

Establishment of hiPSCs Having Dual Germ Line Reporter

To examine in vitro induction conditions for differentiation from hiPSCs into germ cells, hiPSC strain having reporter for BLIMP1 (also known as PRDM1) and TFAP2C (also known as AP2γ) was established. BLIMP1 and TFAP2C were considered to be useful since expression in human germ cell has been reported (Eckert D, et al., BMC Dev Biol. 8, 106, 2008 and Pauls K, et al., Int J Cancer. 115, 470-477, 2005).

Figure 8:
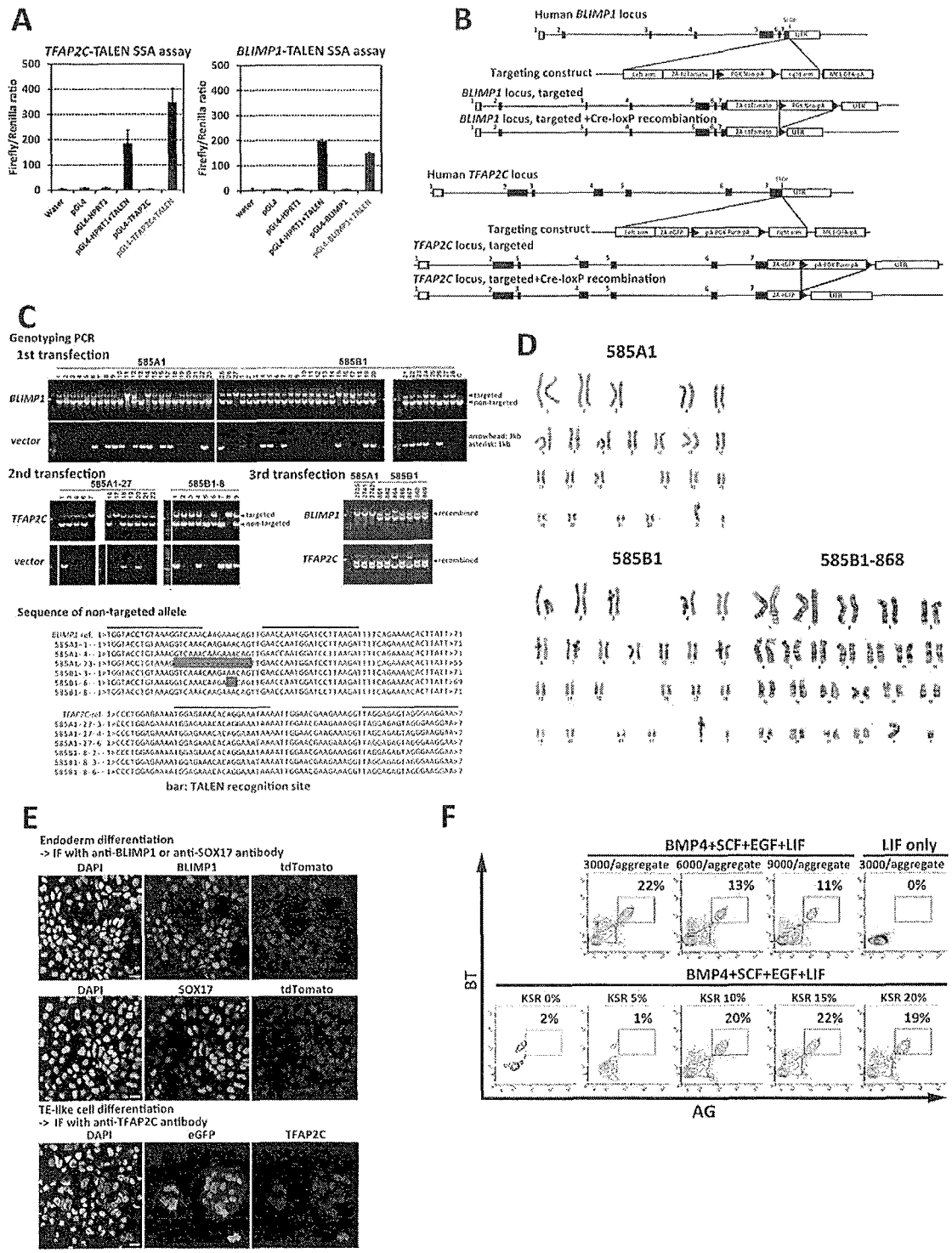
FIG. 8 shows production of BTAG-knockin hiPSCs.

In this case, 585A1 and 585B1, which are two line independent straoms of male hiPSC derived from peripheral mononuclear blood cells were used as hiPSC (Okita K, et al., Stem Cells. 31, 458-466, 2013). This cell line was cultured on E8 fragment (rLN511E8) of recombinant laminin511 in a given medium containing basic fibroblast growth factor (bFGF), whereby single cell passage culture with colony forming ability became possible (Nakagawa M, et al., Sci Rep. 4, 3594, 2014). hiPSCs cultured under such conditions showed more uniform property than culturing under conditions using conventional feeder cells, and gene expression property in multipotency state, which is essentially free of expression of gene relating to the primitive pluripotency of mouse (Nakamura T, et al., Nucleic Acids Res. 43, e60. 2015). Using TALEN (transcription activator-like effector nucleases), dual homologous recombinant iPS cell having both BLIMP1-2A-tdTomato and TFAP2C-2A-EGFP allele (alleles) was isolated. When BLIMP1 and TFAP2C were expressed, the iPS cell showed fluorescence of each of tdTomato and EGFP (FIG. 8B, FIG. 8C and FIG. 8E). From double homologous recombinants, BLIMP1-2A-tdTomato; TFAP2C-2A-EGFP 585B1-868 strain (hereinafter to be referred to as BTAG 585B1-868), which is a recombinant allele showing both heterozygote and normal karyotype, was used (FIG. 1A, FIG. 8D).

Direct Induction of BTAG Positive Cell from hiPSCs

First, whether BTAG 585B1-868 hiPSCs are directly induced into hPGCLCs under conditions for inducing mEpiLCs in a transient state extremely similar to pre-gastrulation mouse ectoderm into mPGCLCs (Hayashi K, et al., Cell. 146, 519-532, 2011) was examined. BTAG hiPSCs were separated into single cells and cultured under floating conditions in GMEM+15% knockout serum replacement (KSR) (GK15) added with major cytokines such as bone morphogenetic 4 (BMP4), stem cell factor (SCF), leukemia suppress factor (LIF), and epidermal growth factor (EGF) (3,000 cells/cell aggregate) and the like in the presence of a ROCK inhibitor (FIG. 1B) (Watanabe K, et al., Nat Biotechnol. 25, 681-686, 2007).

In mEpiLCs, cell aggregate of hiPSC did not express BT and AG even after 2 days from cytokine stimulation and appeared to be loosely bound by observation under a fluorescence Anatomy microscope, rather than strongly expressing Blimp1 and other PGC specific gene in early stages of day 2 of stimulation (Hayashi K, et al., Cell. 146, 519-532, 2011) (FIG. 1C). However, on day 4, some cells started to express BTAG, and a cell population showed strong BTAG expression on day 6 which was maintained at least up to day 8 (FIG. 1C). FACS analysis similarly showed shift of the whole aggregates on day 2 of stimulation to a weak BTAG positive state, about 15% of cells became BTAG positive on day 4, and BT and AG were upregulated by a similar mechanism. On day 6, cell aggregates (about 20%) strongly showing BTAG positive were observed which was confirmed to have been maintained at least up to day 8 (FIG. 1D). However, it should have been noted that a considerable number of cells die through induction. Induction was started at 3,000 cells/aggregate, induction efficiency of BTAG positive cells showed the highest value when not less than 10% of KSR was used as the basal medium for induction (FIG. 8F), and the average number of BTAG positive cells per cell aggregate was about 200 cells/cell aggregate on day 6 of induction (FIG. 1E). The above finding suggests that, different from mEpiSCs and similar to mEpiLCs, hiPSCs show comparatively strong germ cell formation capacity under appropriate conditions.

The dynamics of the gene expression when BTAG positive cells are induced from hiPSCs were quantitatively examined by PCR. hiPSCs express multipotency marker genes POU5F1, NANOG and SOX2 at a high or moderate level, whereas show low or no confirmed expression of genes relating to primitive multipotency such as KLF2, KLF4, TCL1B, TFCP2 L1, ESRRB, and DPPA3 and the like in mouse (FIG. 1F), which was consistent with the report of Nakamura T, et al., Nucleic Acids Res. 43, e60. 2015. However, it should be noted that hiPSCs express ZFP42 and PRDM14 at a comparatively high level (FIG. 1F). hiPSCs did not express or showed only very low expression of genes relating to PGCs (BLIMP1, TFAP2C, NANOS3, DPPA3, DAZL, and DDX4), neuroectoderm (PAX6 and SOX1), mesoderm (T, EOMES, EVX1, SP5, MIXL1, MSX2, and NODAL) and endoderm (GATA4, GATA6, SOX17, and FOXA2) (FIG. 1F).

On the other hand, in cell aggregates on day 2 of cytokine stimulation, expression of major multipotency gene increased, expression of primitive pluripotency gene was maintained low, and some genes relating to PGCs (BLIMP1 and TFAP2C), mesoderm (T, EOMES, SP5 and NODAL), and endoderm (GATA4 and SOX17) started to increase (FIG. 1F).

Furthermore, BTAG positive cells on day 6 of cytokine stimulation markedly increased the expression of POU5F1 and NANOG, but SOX2 did not show such tendency (FIG. 1F). This does not contradict with the results that hPGCs lack SOX2 expression (de Jong J, et al., J Pathol. 215, 21-30, 2008; Perrett R M, et al., Biol Reprod. 78, 852-858, 2008). Mouse early PGC markers such as BLIMP1, TFAP2C and NANOS3 and the like showed a high expression level like SOX17, but expression of DPPA3 was low, and substantial expression of late PGC genes such as DAZL and DDX4 and the like could not be confirmed (FIG. 1F). In BTAG positive cells, the expression level of T and PRDM14 essential for identification of mouse PGC was low (FIG. 1F). Furthermore, it was found that BTAG positive cells increase genes relating to primitive pluripotency (KLF4, TCL1B, and TFCP2L1), mesoderm (EVX1 and MSX2) and endoderm (GATA4) of mouse (FIG. 1F). While decision is difficult since information relating to the gene expression property of early hPGCs is not available, these findings suggest that BTAG positive cells may correspond to early hPGCs. These suggest that hPSC may show a state like former/proximal-gastrula formation ectoderm having an ability to determine the germ cell fate.

Example 2

Strong Induction of BTAG Positive Cell Via Initial Mesoderm-Like State

While BTAG positive cells are directly induced from hiPSCs, cell aggregates contained a considerable number of dead cells, and the amount of the obtained BTAG positive cells was comparatively small (FIG. 1E). Direct induction of germ cell differentiation via formation of floating T cell aggregation may not be an optimal pathway. Thus, the conditions for inducing hiPSCs into an appropriate precursor for germ cell differentiation induction were studied. Prior to germ cell differentiation, based on the finding of the activation of induction into mesoderm lineage induced by BMP4 and WNT3 signal in mouse (Aramaki S, et al., Dev Cell. 27, 516-529, 2013 and Saitou M, et al., Nature. 418, 293-300, 2002), the effect of previously contacting hiPSCs with BMP4, WNT3 and other signaling molecule, which is similar to the use of various extracellular matrix (ECM) constituent components, was examined for induction of a precursor for inducing BTAG positive cell.

Figure 2:
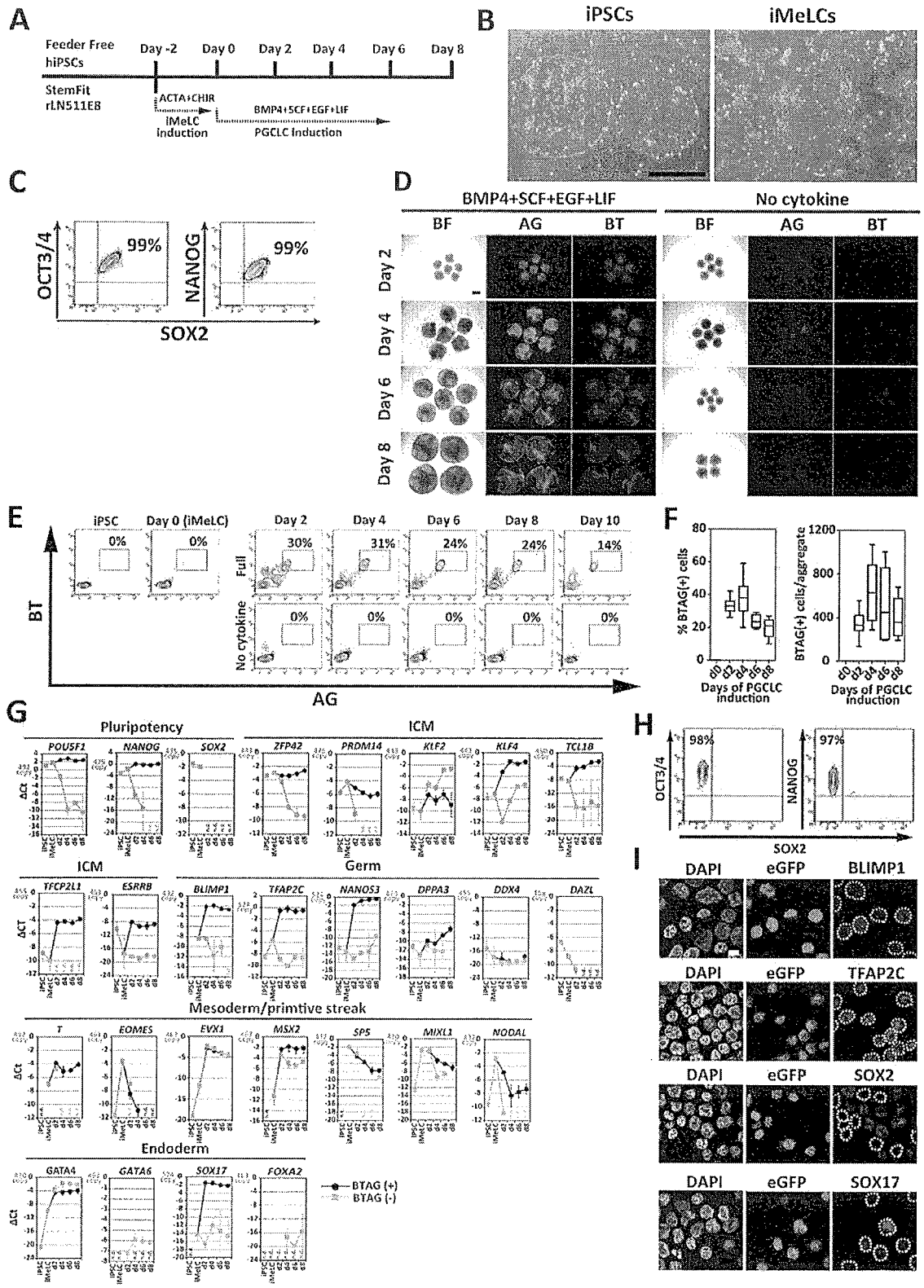
FIG. 2 shows the results of induction of BTAG(+) cells from hiPSCs via mesoderm-like cell (iMeLCs).

It was found that, among the conditions studied, a precursor strongly and stably producing BTAG positive cells is induced by stimulating hiPSCs in GK15 containing activin A (ACTA, 50 ng/ml) and GSK3 inhibitor (CHIR99021 (3 µM)) on a fibronectin coating plate for about 2 days, and forming floating T cell aggregates under conditions with addition of BMP4, LIF, SCF, and EGF (FIG. 2A-F, FIG. 9A and FIG. 9B). When stimulated with ACTA and CHIR, hiPSCs are differentiated into cell having clear boundary between cells (this cell is referred to as initial mesoderm-like cell (iMeLCs)) (FIG. 2A and FIG. 2B), in the formation of floating cell aggregates accompanying cytokine stimulation, these cells start enforced BTAG activation (about 30-40%) on day 2, and the BTAG positive cells (about 60% on day 4) were maintained at least up to day 10 after cytokine stimulation (FIG. 2D, FIG. 2E and FIG. 2F). The number of BTAG positive cells per cell aggregate induced from iMeLCs was about 400 to 1000 cells/cell aggregate on day 6, which is markedly larger than cells directly induced from hiPSCs (FIG. 2F), and cell death was hardly observed in the induction of BTAG positive cells from iMeLCs.

Figure 9:
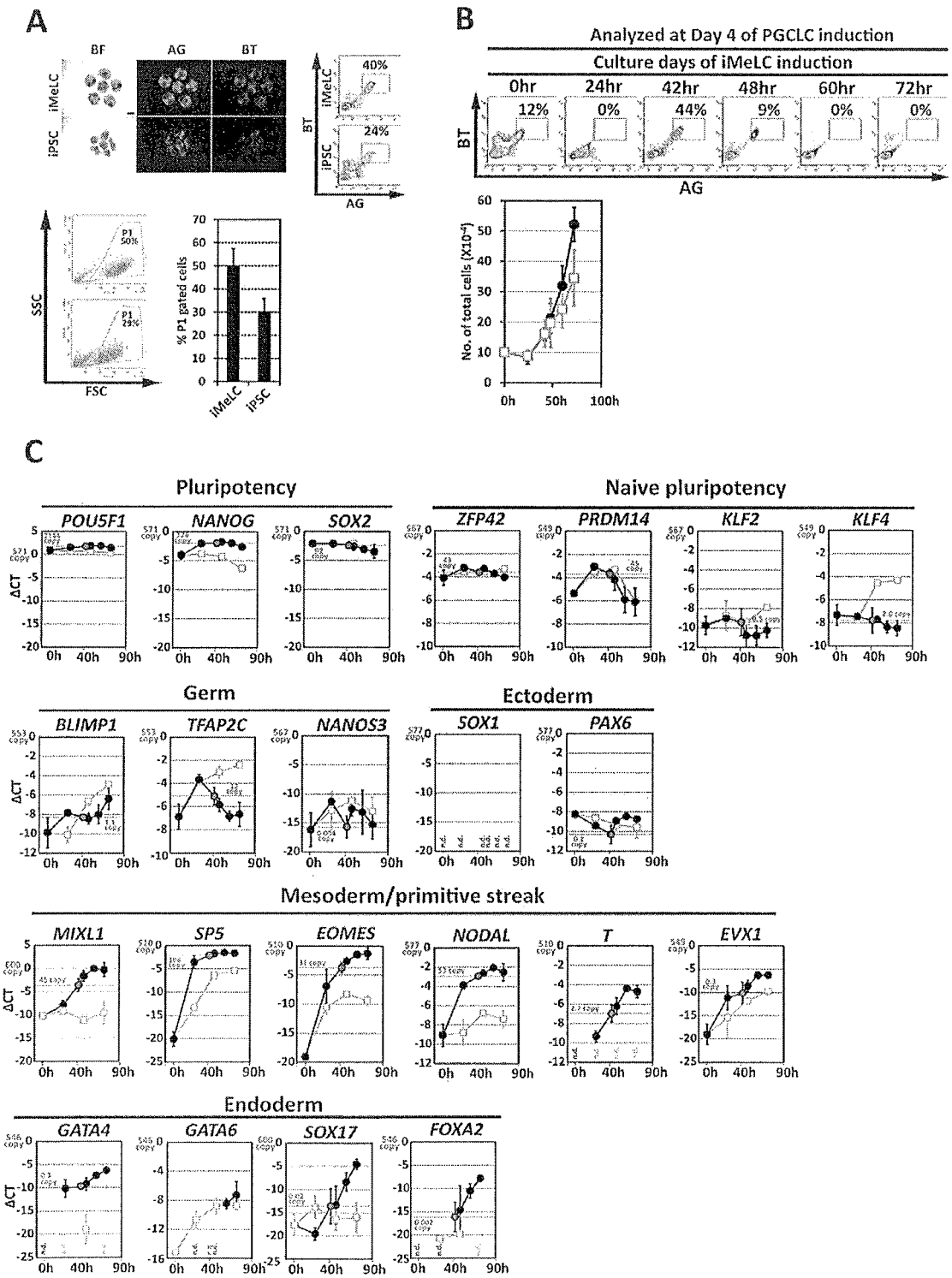
FIG. 9 shows analysis results of the iMeLCs induction and properties thereof.
Figure 10:
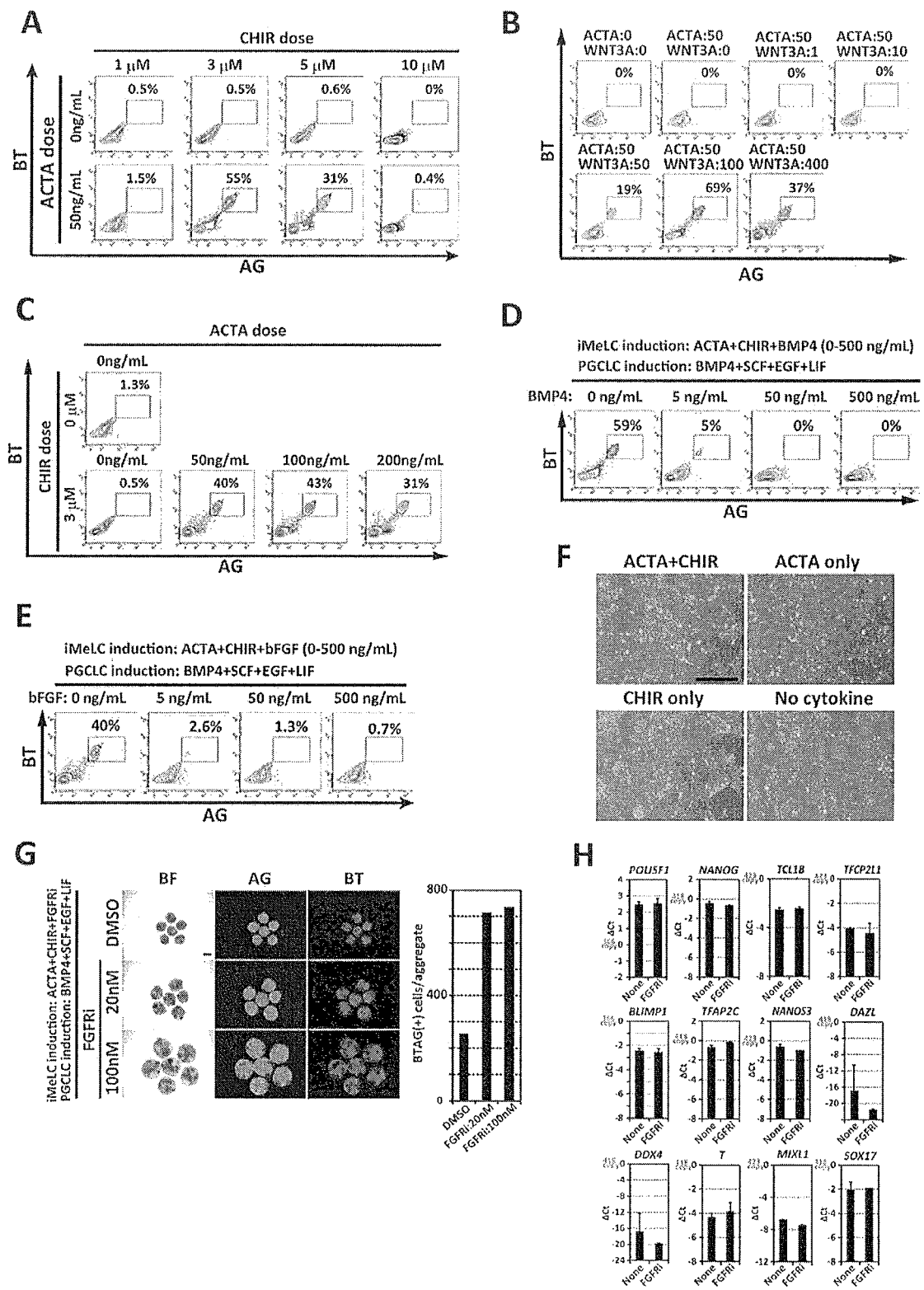
FIG. 10 shows study results of the induction method of iMeLC.

Successively, the effect of the related signaling pathway/culture conditions in the induction of iMeLCs having induction capacity into BTAG positive cells was evaluated. Like the induction of mEpiLC from mESCs/iPSCs, the efficiency of BTAG positive cell induction largely depends on the induction time of iMeLCs, and the optimal time for BTAG 585B1-868hiPSCs was about 42 hr (FIG. 9B). When stimulation with ACTA and CHIR was elongated, the property of mesoderm (T, EOMES, EVX1, SP5, MIXL1, and NODAL) and the property of endoderm (GATA4, GATA6, SOX17, and FOXA2) were further increased and BTAG positive cell induction capacity was lost (FIG. 9B and FIG. 9C). While ACTA (not less than 50 ng/ml) and CHIR (3-5 µM) are essential for the induction of iMeLCs having induction capacity into BTAG positive cells, it was shown that CHIR is replaceable with WNT3A (not less than 50 ng/ml), and WNT signaling is essential for iMeLCs induction (FIG. 10A-C). On the other hand, the signaling of BMP4 and bFGF acts negatively to the iMeLCs induction (FIG. 10D and FIG. 10E). In the induction of iMeLCs, when FGF receptor (FGFR) signaling is inhibited by a specific inhibitor (PD173074 (FGFRi)), the cells in the cell aggregates such as BTAG positive cell and the like were more strongly proliferated and survived, and the number of BTAG-positive cells per cell aggregate increased (FIG. 10G and FIG. 10H). From these findings, it was clarified that the induction of iMeLCs having strong BTAG positive cell induction capacity requires a specific signaling pathway. It was confirmed that iMeLCs is a precursor of mesoderm and embryonic endoderm.

Figure 11:
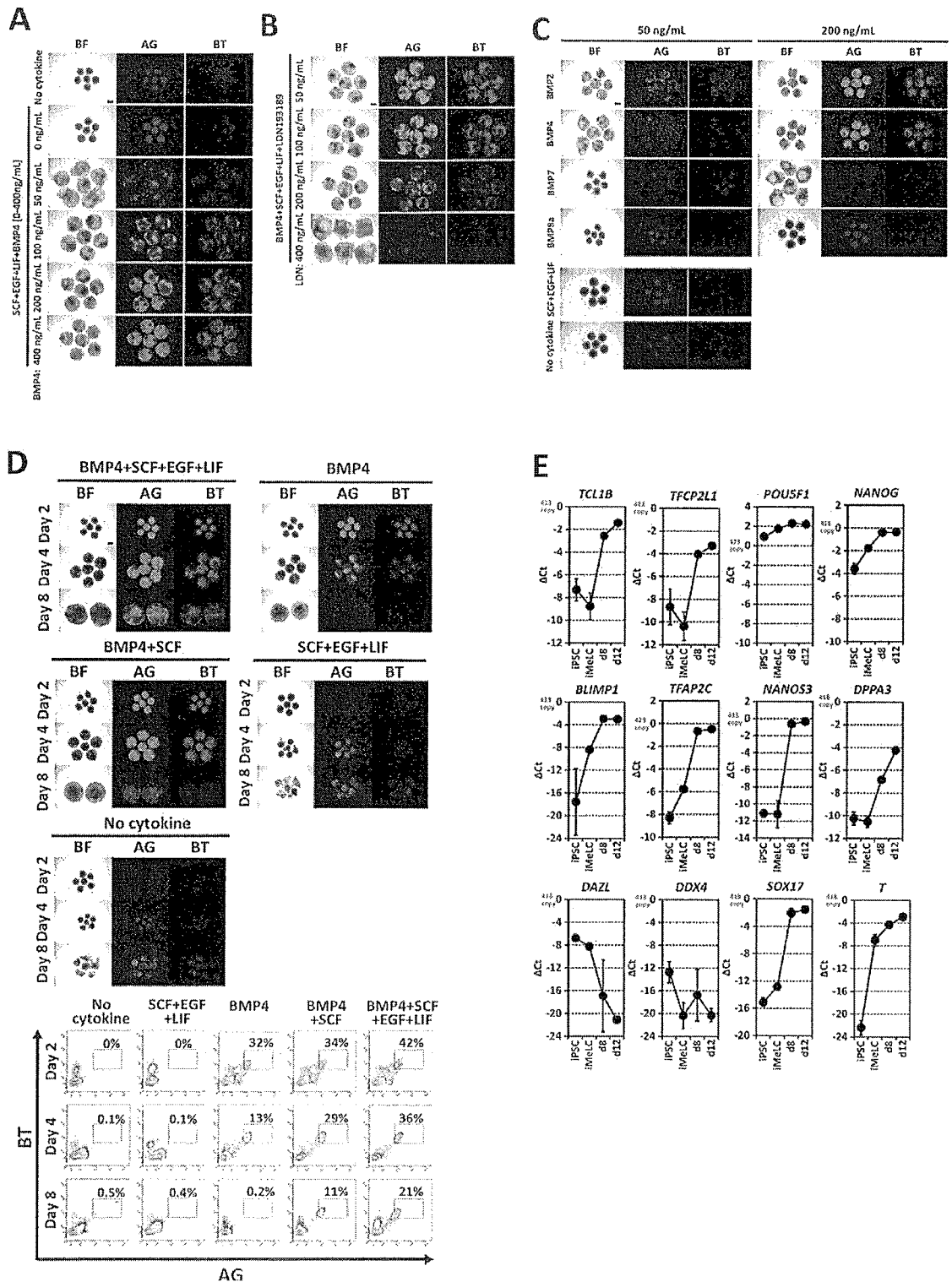
FIG. 11 shows study results of the signal necessary for the induction of BTAG(+) cells.

Next, signal pathway necessary for induction of iMeLCs into BTAG positive cells was examined. While BMP4 is essential for the induction of BTAG positive cells, SCF, LIF and EGF had a role of maintaining rather than inducing BTAG positive cells in the cell aggregates (FIG. 11A-D). Since the effect of BMP4 is blocked by activin receptor-like kinase2/3 (ALK2/3) inhibitor LDN193189, it was shown that the signal from BMP4 goes through ALK2/3 receptor (FIG. 11B). From the above, it was confirmed that induction of BTAG positive cell from iMeLCs and proliferation/survival thereof requires a signal similar to that of the induction from mEpiLCs to mPGCLCs and proliferation/survival of mPGCLC (Hayashi K, et al., Cell. 146, 519-532, 2011).

The dynamics of gene expression in the induction of BTAG positive cells via iMeLCs were confirmed by Q-PCR. In iMeLC induction, the expression levels of multipotency marker gene (POU5F1, NANOG and SOX2), primitive pluripotency gene (KLF2, KLF4, TCL1B, TFCP2L1, ESRRB and DPPA3), and PGC-related gene (BLIMP1, TFAP2C, NANOS3, DPPA3, DAZL and DDX4) and endoderm-related gene (GATA4 and SOX17) did not change. However, the genes relating to the development of mesoderm showed a mild increase (T, EOMES, SP5, MIXL1 and NODAL) (FIG. 2G and FIG. 9C), and it was shown that stimulation with ACTA and CHIR induces hiPSCs into initial mesoderm-like/development initial streak-like state. The gene expression property of BTAG positive cells induced from iMeLCs was essentially the same as that of BTAG positive cells directly induced from hiPSCs. That is, the expression of POU5F1 and NANOG was high, SOX2 rapidly decreased, initial PGC marker markedly increased like SOX17 and SOX15 (BLIMP1, TFAP2C and NANOS3), and the late PGC genes (DAZL and DDX4) were not substantially expressed (FIG. 2G and FIG. 11E).

The expression of OCT4, NANOG, BLIMP1, TFAP2C and SOX17 and the suppression of SOX2 in BTAG positive cells were also confirmed by FACS and immunofluorescence analysis.

From the above results, it was clarified that hiPSCs are induced into iMeLCs with increased initial mesoderm genes, and sequentially induced forcibly into a state potentially similar to BTAG positive cells, initial hPGCs.

Example 3

Transcription of BTAG Positive Cell as hPGCLCs and Analysis of Induction Pathway To further understand the property and induction pathway of BTAG positive cells, the technique of Nakamura T, et al., Nucleic Acids Res. 43, e60. 2015 was used and global transcription profile, and global transcription profile relating to the identification of non-human primates (*Macaca fascicularis*) assumed to be similar to human PGCs (global transcription profile of gonad PGCs, and mPGCLCs (mESCs, mEpiLCs, d2, d4, d6 mPGCLCs) were compared in detail for hiPSCs, iMeLCs, BTAG positive cells induced from iMeLCs on day 2 (d2), day 4 (d4), day 6 (d6) and day 8 (d8), and BTAG positive cells directly induced from hiPSCs on day 6 (d6).

Figure 12:
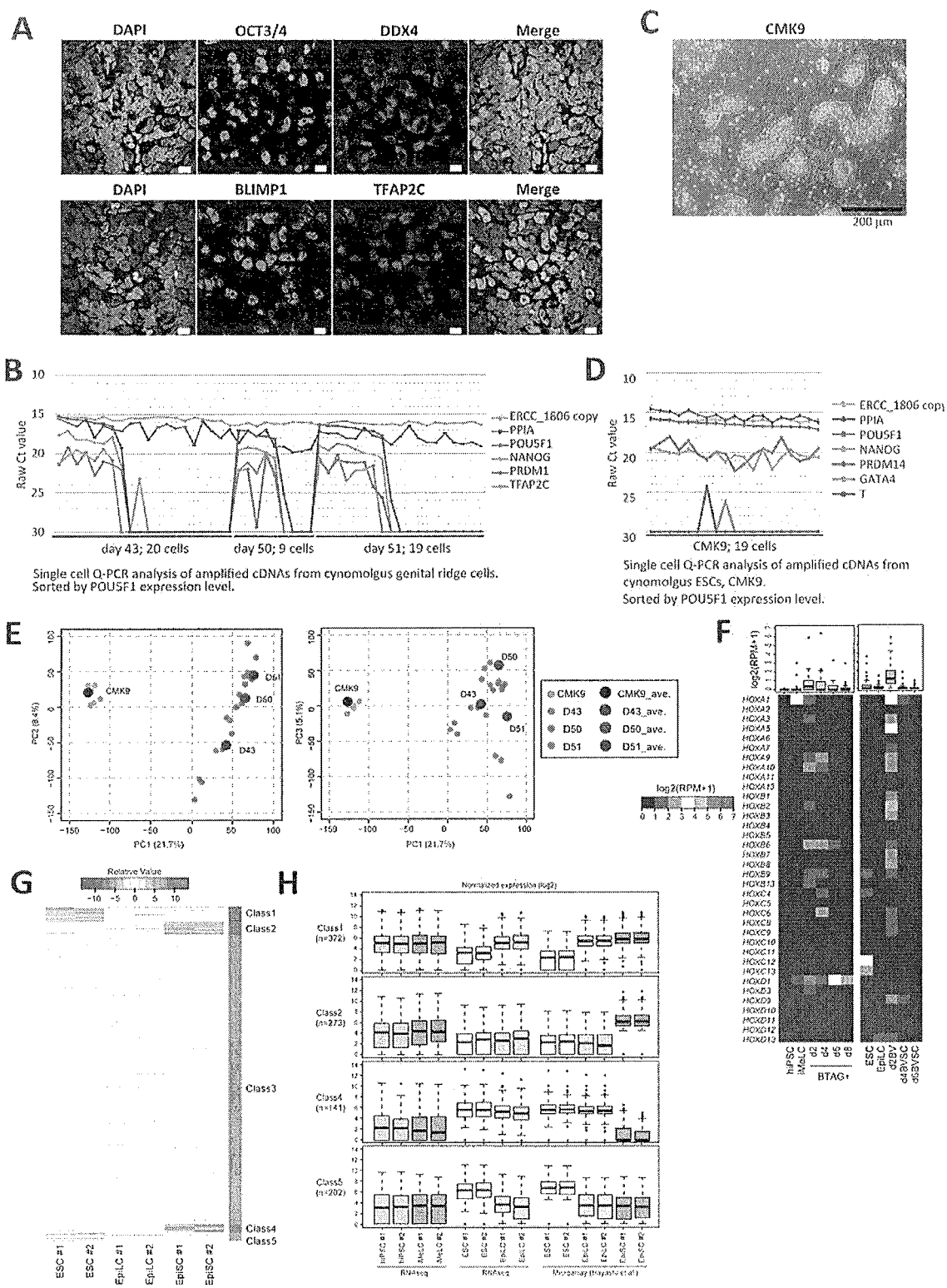
FIG. 12 shows comparison of cyPGCs and cyESCs, and comparison results of mouse pluripotent stem cells and human pluripotent stem cells.

To determine the global transcription profile of gonad PGCs of Macaca fascicularis (cy), E43, 50, and 51 of Macaca fascicularis embryo (almost corresponding to mouse E10.5-13.5) were isolated, gonad was removed (FIG. 12A), and each gonad was separated into single cells. PGCs (POUF51, NANOG, BLIMP1 and TFAP2C positive)-derived single-cell cDNAs were produced and analysis by RNA-seq was performed (FIG. 12B-D).

Figure 3:
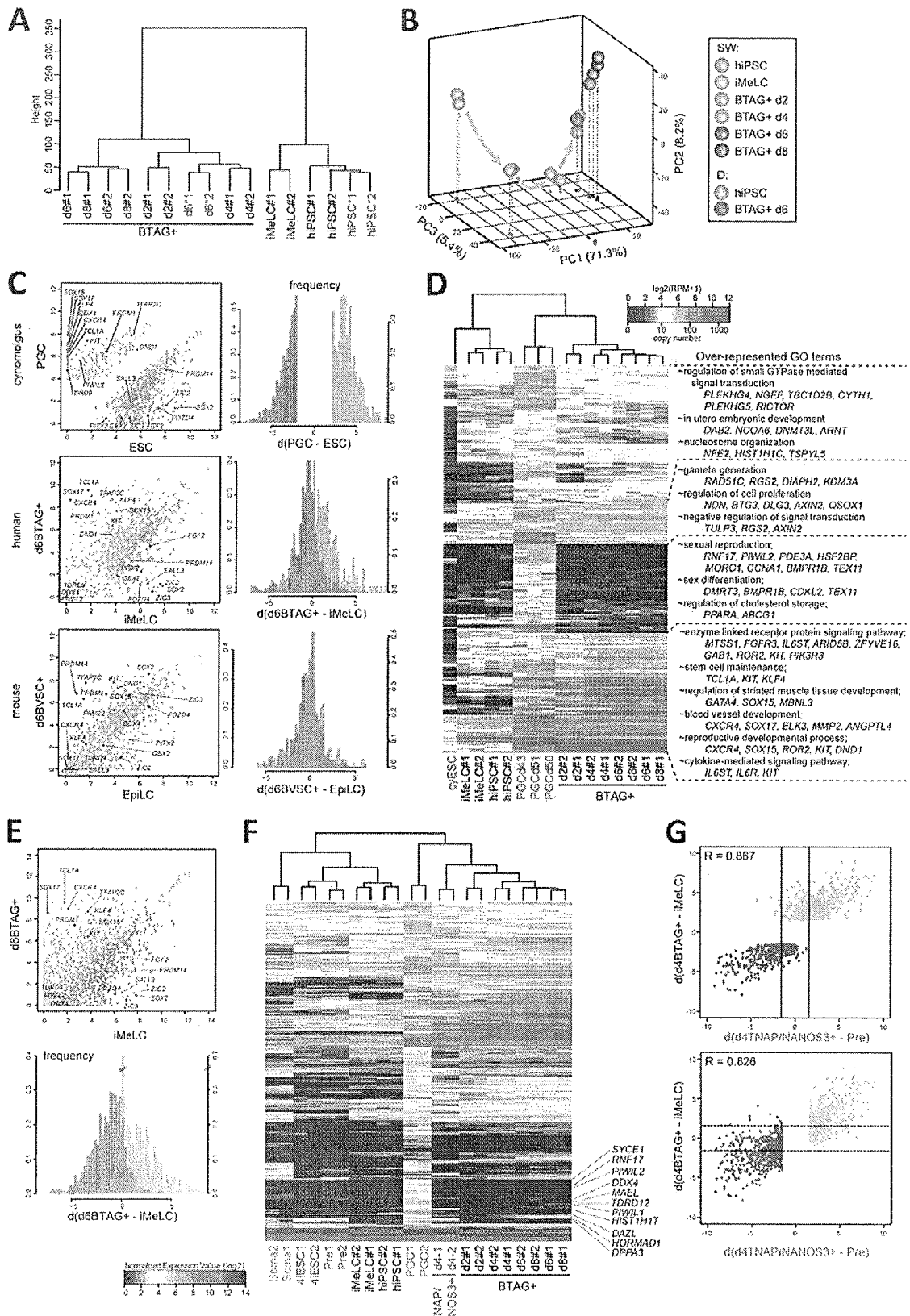
FIG. 3 shows the study results that BTAG(+) cell is hPGCLC.

By unsupervised hierarchical clustering (UHC), cells relating to the induction pathway of BTAG positive cells were classified into two clusters of hiPSCs and iMeLCs each independently constituting a subcluster, and d2-d8 BTAG positive cells having stage dependency subcluster (FIG. 3A). Interestingly, d4 BTAG positive cells induced via iMeL state formed subcluster d6 together with BTAG positive cells directly induced from hiPSCs (FIG. 3A). This shows that, in direct induction from hiPSCs, BTAG positive cells are formed through a pathway similar to BTAG positive cell formation via iMeLCs. By principal component analysis (PCA), iMeLCs were plotted from PC1 negative hiPSCs along PC2 and PC3 axis, and BTAG positive cells which are almost the same PC1 positive were plotted in a stage dependent manner and along the PC2 and PC3 axis (FIG. 3B). As mentioned above, hiPSCs and iMeLCs have comparatively similar properties, BTAG positive cells have properties different from them, and induction of BTAG positive cell is a directional and progressive process to acquire cell phenotype.

Next, the gene expression properties of cyPGCs and BTAG positive cells were compared (FIG. 12D). cyESCs, CMK9 strain-derived single-cell cDNAs were produced and these cDNAs were subjected to RNA-seq analysis. A gene set showing an increase in cyPGCs as compared to cyESCs was identified, and human homologous genes relative to these genes were determined. Formation of cluster by d2-d8 BTAG positive cells together with cyPGCs was shown by UHC analysis. Many of the genes co-expressed in BTAG positive cells and cyPGCs related to the gene ontology (GO) terms of "enzyme linked receptor protein signaling pathway", "stem cell maintenance", "reproductive development process" and "gamete production" and the like (FIG. 3D). A group of genes not expressed in BTAG positive cell but expressed in cyPGCs were mainly constituted of those mainly expressed in late PGCs and having GO terms such as "sexual reproduction", "sexual differentiation" and the like (FIG. 3D). Furthermore, it was clarified by scatter plot analysis that genes up- or down-regulated in cyPGCs as compared to cyESCs are generally up- or down-regulated in d6 BTAG positive cells as compared to iMeLCs. However, even though mPGCLC is known to show a transcription profile highly similar to mPGCs and have the function as authentic PGCs, this tendency was very weak when mPG-CLCs and mEpiLCs were compared (FIG. 3C) (Hayashi K, et al., Science. 338, 971-975, 2012 and Hayashi K, et al., Cell. 146, 519-532, 2011). Except those relating to late PGC gene, these findings demonstrate that BTAG positive cells display gene expression profiles similar to those of cyPGCs and that mPGCLCs exhibit total gene expression significantly different from that of cyPGCs which is assumed to be due to species difference. From the above findings, BTAG positive cells are considered to correspond to initial hPGCs and thereafter show property as hPGCLCs.

Figure 4:
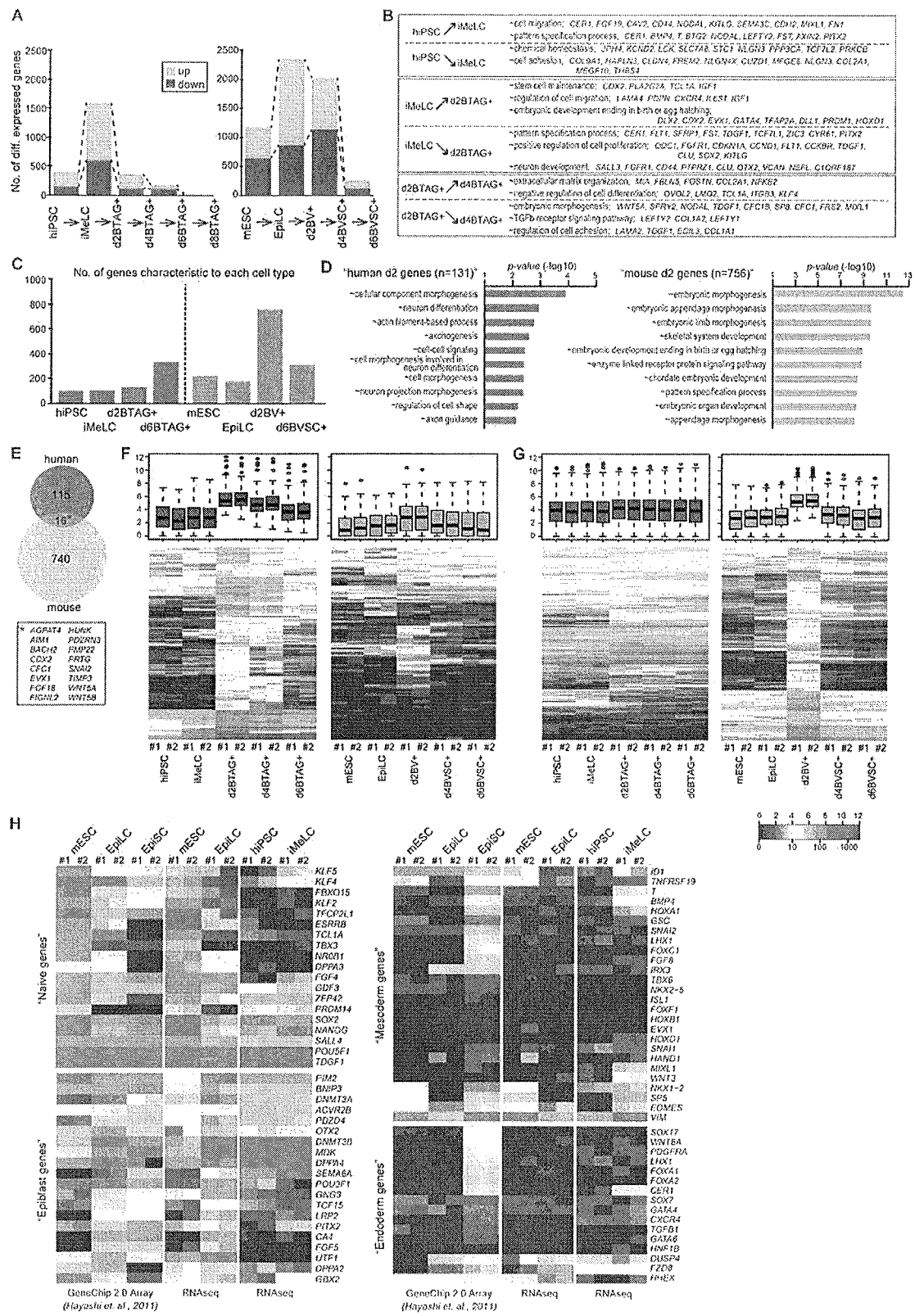
FIG. 4 shows the study results of induction pathway of hPGCLCs.

Next, individual genes that are up- or down-regulated while the cellular state changes in hPGCLC induction were examined and compared to the genes in mPGCLC induction (FIG. 4A). It was noted that the number of genes that are up- or down-regulated while the cellular state changes in hPG-CLC induction was smaller than the genes regulated during mPGCLC induction. During iMeLC-d2 hPGCLC change, 991 and 601 genes were respectively up- or down-regulated, and during mEpiLC-d2 mPGCLC change, 1,482 and 870 genes were respectively up- or down-regulated. During d2-d4 hPGCLC change, 235 and 126 gene alone were respectively up- or down-regulated, and during d2-d4 mPG-CLC change, 888 and 1,141 genes were respectively up- or down-regulated (FIG. 4A). Many of the genes that are up-regulated during hiPSC-iMeL change had GO terms of "cell migration", "pattern specification process" and the like, and include CERI, FGF19, NODAL, KITLG, SEMA3C, MIXL1, BMP4, T, EOMES, LEFTY2, FST, PITX2 and the like. On the other hand, Many of the genes that are down-regulated during hiPSC-iMeL change had GO terms of "chemical homeostasis", "cell adhesion" and the like (FIG. 4B).

The genes that are up-regulated during iMeLC-d2 hPG-CLC change include those having a possibility of playing an important role in the identification of hPGCLC (e.g., TFAP2C, PRDM1, SOX17, SOX15, KLF4, KIT, TCL1A, and DND1) (FIG. 3D and FIG. 4B), and many of them have GO terms of "stem cell maintenance", "control of cell migration" and the like. On the other hand, many of the genes that are down-regulated have GO terms of "pattern specification process", "neuron development" and the like (FIG. 4B). As mentioned above, gene change between d2 and d4 hPGCLCs was comparatively small, d4 hPGCLCs down-regulated some genes for "embryonic morphogenesis" and the total gene expression profile of d6 and d8 hPGCLCs was essentially the same (FIG. 4A and FIG. 4B).

In hPGCLC and mPGCLC induction, genes expressed at the highest level among respective cell types (2-fold or more than other three cell types) were identified (FIG. 4C). It has been reported that the major phenomena of mPGC/PGCLC induction include rapid and powerful activation/subsequent suppression of "somatic mesoderm program" (Kurimoto K, et al., Genes Dev. 22, 1617-1635, 2008, Saitou M, et al., Nature. 418, 293-300, 2002 and Yabuta Y, et al., Biol Reprod. 75, 705-716, 2006). The gene (n=756) of the maximum group was found to be most frequently expressed in d2 mPGCLCs (d2 mPGCLC gene). These genes showed remarkably high P values, had many GO terms such as "embryonic morphogenesis" and "pattern identification process", and the like and the majority thereof were suppressed by d4 rnPGCLCs (FIG. 4C and FIG. 4D). The number of genes most frequently expressed in d2 hPGCLCs (d2 hPG-CLC gene) was comparatively small (104), and the P value was not high. However, many genes had GO terms mainly including "cellular component morphogenesis" and "neuron differentiation" and were gradually suppressed by d4 and d6 hPGCLCs (FIG. 4C and FIG. 4D).

Many of the human homologous genes of d2 mPGCLC gene showed relatively constant expression in hPGCLC induction (no expression or expression at the same level). On the other hand, only a small number of mouse homologous genes of d2 hPGCLC gene showed transient upregulation in d2 mPGCLC gene (FIG. 4E and FIG. 4G). Therefore, only 16 genes containing WNT5A, WNT5B, CFC1, EVX1, SNAI2 and CDX2 but free of Hox gene were common in d2 hPGCLC gene and d2 mPGCLC gene (FIG. 4E and FIG. 12F).

From the above results, transcription programming in hPGCLC and mPGCLC induction was shown and it was shown that hPGCLC induction did not show marked activation/subsequent suppression of "somatic mesoderm program".

Successively, to investigate the precursor state of hPGCLC induction, the relationship between hiPSCs, iMeLCs, mESCs, mEpiLCs, and mEpiSCs was examined. Since the overall transcriptional state varies between species, direct comparison between human and mouse cells is not possible. Thus, representative genes of mice having major function relating to inner cell mass (ICM)/primitive pluripotency, pre-gastrulation ectoderm, mesoderm, and endoderm formation were selected and expression profiles in these cells were examined. As shown in FIG. 4H, genes relating to ICM/primitive pluripotency were highly expressed in mESCs, decreased in mEpiLCs, and further decreased in mEpiSCs, but genes relating to ectoderm increased in both mEpiLCs and mEpiSCs. Genes relating to mesoderm and endoderm were generally low in mESCs and mEpiLCs, but increased to some extent in mEpiSCs (FIG. 4H). These data are not consistent with the idea that mESCs, mEpiLCs and mEpiSCs have properties resembling ICM/initial ectoderm, pre-gastrulation ectoderm, and post-gastrulation ectoderm-precast embryonic ectoderm, and posterior embryonic ectoderm respectively.

The expression patterns of genes relating to ICM/primitive pluripotency in hiPSCs and iMeLCs were similar to mEpiLCs, but not similar to mESCs (FIG. 4H). About half of the genes selected in relation to mouse pre-gastrulation ectoderm were strongly expressed in hiPSCs and iMeLCs but the remaining half did not show remarkable expression, which is considered to be caused by species differences. Similar to the Q-PCR analysis (FIG. 1F, FIG. 2G and FIG. 9C), some genes of mesoderm rather than endoderm formation increased in iMeLCs but not in hiPSCs (FIG. 4H).

From the above results, hiPSCs cultured under this condition had properties most similar to mEpiLCs out of mESCs, mEpiLCs and mEpiSCs, regardless of the species differences, and it was suggested that they can be reproductive cells by human-specific pathway.

Figure 13:
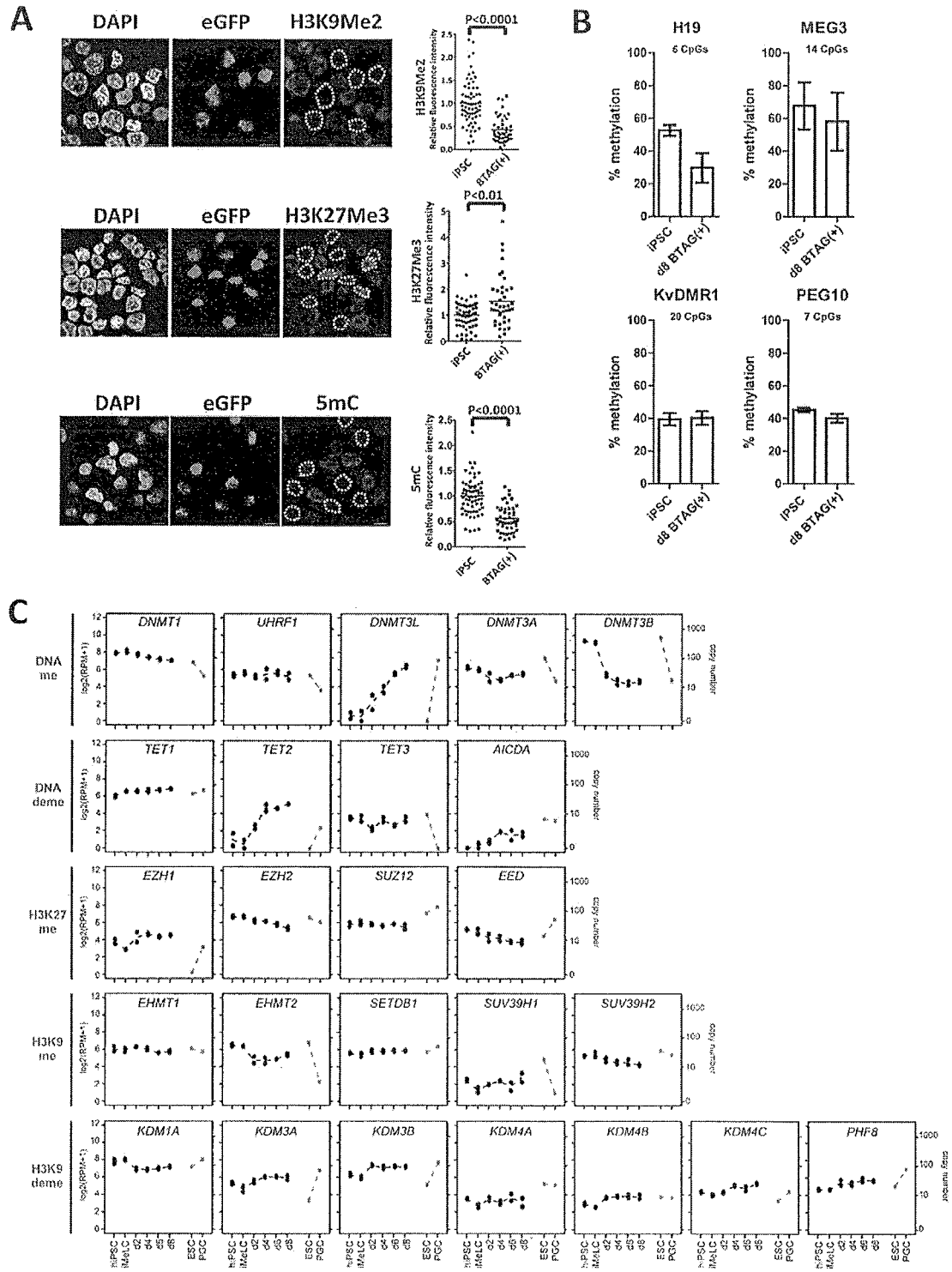
FIG. 13 shows epigenetic analysis results of hPGCLCs.

Next, the epigenetic profile of hPGCLCs was examined. Like mouse migrating PGC, in mPGCLCs, histone H3 lysine 9 dimethylation (H3K9me2) level decreased, histone H3 lysine 27 trimethylation (H3K27me3) level increased, and DNA methylation [5-methylcytosine (5mC)] level decreased, as compared to mEpiLCs, but parental imprints were maintained (Hayashi K, et al., Cell. 146, 519-532, 2011 and Kurimoto K, et al., Genes Dev. 22, 1617-1635, 2008). Next, H3K9me2, H3K27me3 and 5mC levels were compared between hiPSCs and d8 hPGCLCs by immunofluorescence analysis. While H3K9me2 level in d8 hPGCLCs was lower than that in hiPSCs, H3K27me3 level varied. While hPGCLCs showing higher H3K27me3 levels were present, those showing H3K27me3 level similar to hiPSCs were also present (FIG. 13A). Furthermore, 5mC level in d8 hPGCLCs was lower than hiPSCs (FIG. 13A).

To elucidate the mechanism of epigenetic reprogramming by hPGCLCs, the expression of epigenetic modification factor relating to hPGCLC induction was examined by reference to gonad cyPGCs. Among the molecules included in DNA methylation, DNMT3B rapidly decreased in hPGCLCs, but the expression of DNMT1 and UHRF1 was maintained. DNMT3A, DNMT3B and UHRF1 decreased in cyPGCs (FIG. 13C). Among the molecules included in DNA methylation, TET1 was expressed in a relatively constant amount, but other genes were not expressed or low in hPGCLC induction and cyPGCs (FIG. 13C). EHMT2, which is the major enzyme of H3K9me2, was suppressed by hPGCLCs and cyPGCs, and several H3K9me2 demethylases (KDM1A, KDM3A, KDM3B) were expressed (FIG. 13C). Among the molecules included in H3K27me3, EZH2 and SUZ12 showed a constant expression level during PGCLC induction, but EED was suppressed in hPGCLCs. On the other hand, in cyPGCs, EZH2, EED, and SUZ12 were strongly expressed (FIG. 13C).

Example 4

Search for Surface Marker of hPGCLCs

Figure 5:
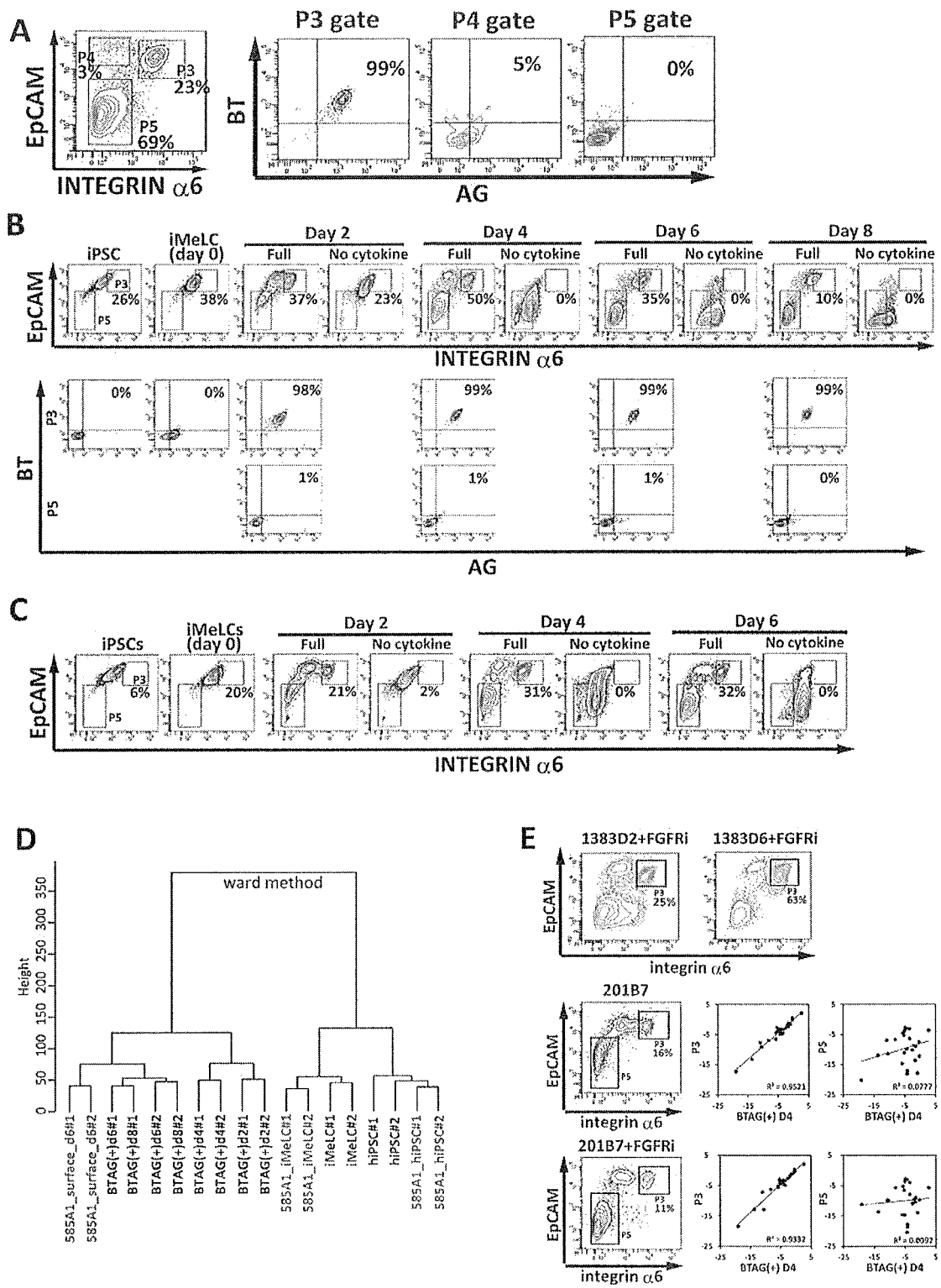
FIG. 5 shows the analysis results of the surface marker of hPGCLCs.

To induce and identify hPGCLCs from hiPSCs without fluorescence reporters, surface markers that identify hPGCLCs were searched for. Among the screened several surface markers, a combination of [PECAM (CD31), INTEGRINα6 (CD49f), INTEGRINβ3 (CD61), KIT (CD117), EpCAM, PODOPLANIN, and TRA1-81], EpCAM (APC-A channel) and INTEGRINα6 (Horizon V450-A channel) separated day 6 cell aggregates induced from BTAG 585B1-868 hiPSCs into three different populations. That is, they were separated into high EpCAM and high INTEGRINα6 (P3 gate), high EpCAM and low INTEGRINα6 (P4 gate), low EpCAM and low INTEGRINα6 (P5 gate) (FIG. 5A). The high EpCAM and high INTEGRINα6 population (P3 gate) was almost the same in BTAG positive hPGCLCs (about 98.9% of high EpCAM and high INTEGRINα6 cells were BTAG positive cells; BT: PE-Texas Red-A channel; AG: FITC-A channel). Other populations were substantially negative/weakly positive for BTAG (FIG. 5A). On day 2 of induction, the high EpCAM and high INTEGRINα6 population was identifiable (about 37%), and substantially the same as the BTAG positive population (about 98% of high EpCAM and high INTEGRINα6 cells were BTAG positive). Thereafter, they remained at least up to day 8 (FIG. 5B).

To investigate whether hPGCLCs can be isolated using surface markers, independent reporter-free strain 585A1 hiPSCs were induced into hPGCLCs via iMeLCs. As shown in FIG. 5C, on day 2 of induction, a high EpCAM and high INTEGRINα6 population (about 21%) emerged in cell aggregates, and this population increased up to day 4 (about 31%) and day 6 (about 32%). To determine whether this population is hPGCLCs, total RNA was extracted from the population on day 6 of induction and the global transcription profile was analyzed by RNA-seq. As shown in FIG. 5D, UHC analysis indicate that high EpCAM and high INTEGRINα6 cells on day 6 confluence with BTAG positive hPGCLCs on days 6 and 8 and it was confirmed that high EpCAM and high INTEGRINα6 cells on day 6 were hPGCLCs.

Example 5

Important Function of BLIMP1 in Identifying hPGCLC

Figure 6:
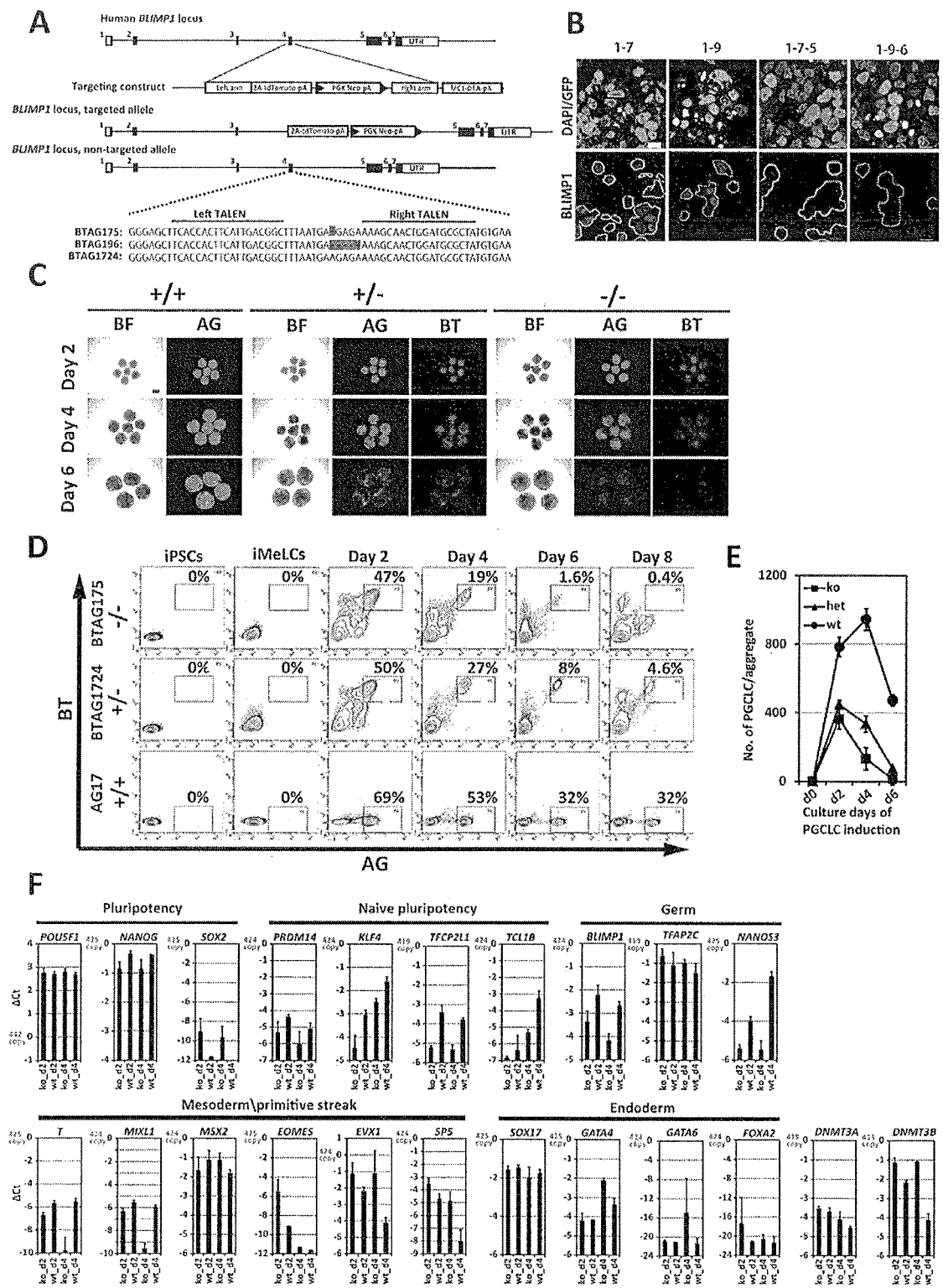
FIG. 6 shows the results showing importance of BLIMP1 in hPGCLCs.

The role of identifying hPGCLC of BLIMP1 which is an important transcription factor for identifying mouse PGC was investigated. Using the TALEN homologous recombination strategy, a hiPSC strain having TFAP2C-2A-EGFP allele was produced (AG 585B1-17,19), and exon 4 of BLIMP1 gene was replaced with tdTomato so that tdTomato would be expressed and BLIMP1 would be knocked out with the target allele (FIG. 6A, FIG. 14A and FIG. 14B). Similar to one replaced by other allele with a frameshift deletion and tdTomato and containing one BLIMP allele (BLIMP1 homozygously knocked out clones: BLIMP1$^{-/-}$), several clones knocked out by heterozygous targeting of BLIMP1 were isolated (BTAG; BLIMP1$^{+/-}$) (FIG. 6A and FIG. 14B).

AG; BLIMP1$^{+/+}$, BTAG; BLIMP1$^{+/-}$, and BTAG; BLIMP1$^{-/-}$ hiPSCs were induced into iMeLCs, and further induced into hPGCLCs. It was confirmed that AG positive cells induced from BTAG; BLIMP1$^{-/-}$ hiPSCs do not express BLIMP1 (FIG. 6B). As shown in FIG. 6C-E, AG; BLIMP1$^{+/+}$ hiPSCs were strongly induced into AG positive hPGCLCs and maintained as hPGCLCs (d2: about 69.3%; d4: about 52.8%; d6: about 32.2%; d8: about 32.2%). In contrast, BTAG; BLIMP1$^{-/-}$ hiPSCs were comparatively efficiently induced into BTAG positive cell on day 2 of induction (about 47.4%), but the cell number of BTAG positive rapidly decreased on day 4 (about 18.8%), and these cells almost disappeared on day 6 (about 1.6%) (FIG. 6C-E). From this, it was shown that BLIMP1 is essential for identification/maintenance of hPGCLCs. Similar to the results of capacity-dependent function of mouse Blimp1 (Ohinata Y, et al., Nature. 436, 207-213, 2005; Vincent S D, et al., Development. 132, 1315-1325, 2005), BTAG; BLIMP1$^{+/-}$ hiPSCs showed an intermediate phenotype between wild-type and BTAG; BLIMP1$^{-/-}$ hiPSCs. That is, the induction rate of BTAG positive cells on days 2, 4, 6, and 8 was respectively about 49.6%, about 27.0%, about 8.1% and about 4.6% (FIG. 6C-E). The same results were obtained when other independent strain BTAG; BLIMP1$^{-/-}$ hiPSCs were used.

To investigate the role of BLIMP1 in hPGCLC induction, RNA was extracted from d2 and d4 (BT) AG positive cells induced from AG; BLIMP1$^{+/+}$ and BTAG; BLIMP1$^{-/-}$ hiPSCs and the expression of major genes was analyzed by Q-PCR (FIG. 6F). BLIMP1$^{-/-}$; BTAG positive cells increased TFAP2C, but an increase of gene NANOS3, KLF4, TFCP2L1, and TCL1B and the like was suppressed (FIG. 6F). BLIMP1$^{+/-}$; BTAG positive cells did not maintain T and MIXL1 but did not suppress EVX1 and SP5, and an effect on EOMES and MSX2 was not found (FIG. 6F). This indicates that BLIMP1 exerts other effect on genes relating to mesoderm development. Similarly, in BLIMP1$^{-/-}$; BTAG positive cells, GATA4 suppressed suppression but a clear effect on SOX17, GATA6, and FOXA2 was not found (FIG. 6F). Particularly, BLIMP1$^{-/-}$; BTAG positive cells did not suppress DNMT3B (FIG. 6F).

Figure 7:
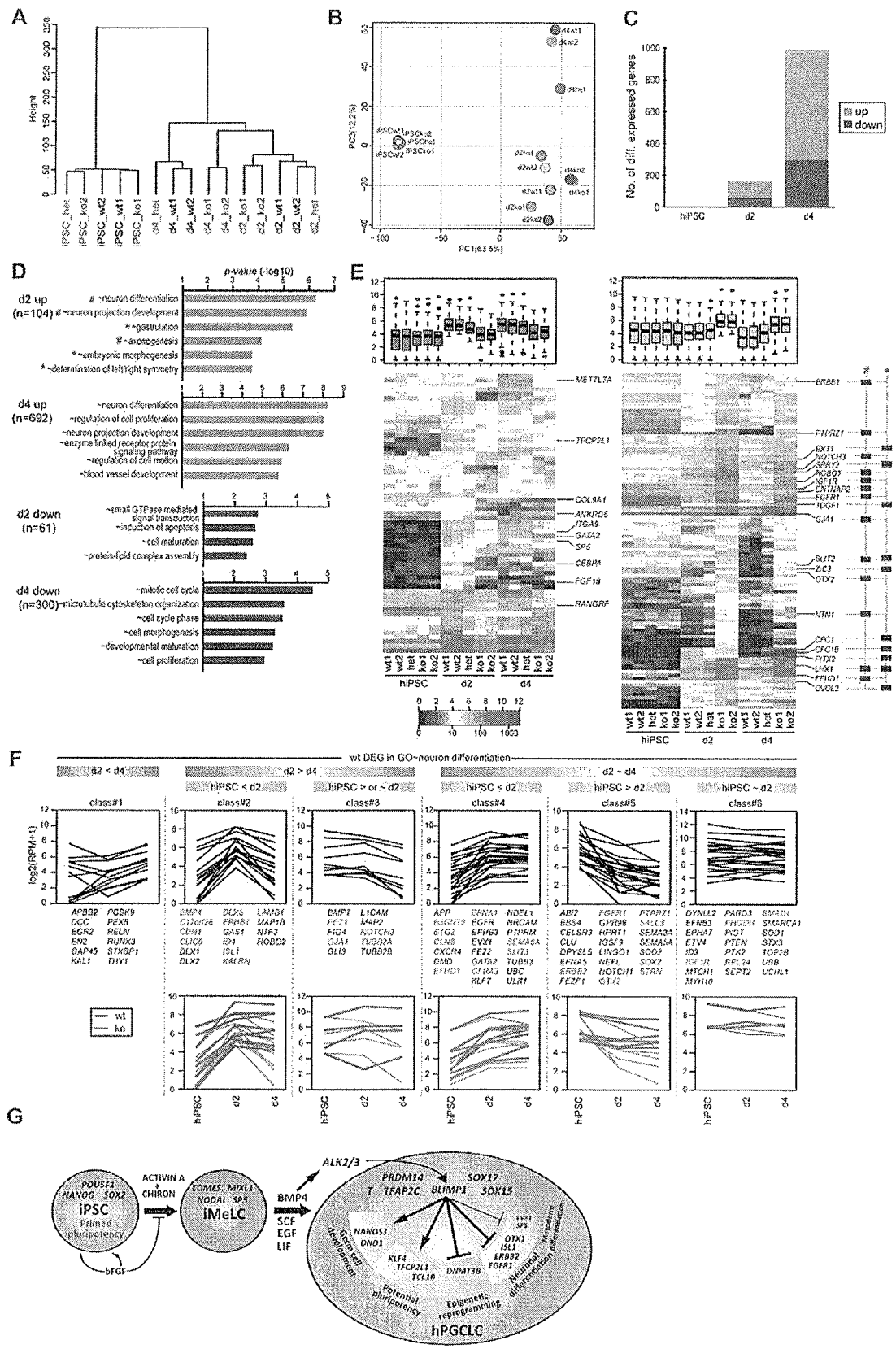
FIG. 7 shows the study results of the role of BLIMP1 in neuron differentiation.

The transcriptome of BLIMP1$^{-/-}$; BTAG positive cells was compared with wild-type and BLIMP1$^{+/-}$ hPGCLCs by RNA-seq. While BLIMP1$^{-/-}$; BTAG positive cells acquired properties similar to those of d2 hPGCLCs, UHC and PCA analysis showed that further differentiation towards d4 PGCLC state did not proceed (FIG. 7A and FIG. 7B). To examine faulty in BLIMP1$^{-/-}$ cells, genes up- or down-regulated in d2 and d4 BLIMP1$^{-/-}$; BTAG positive cells were respectively compared with d2 and d4 PGCLCs. Many of the genes (104 genes) increased in d2 BLIMP1$^{-/-}$; BTAG positive cells had GO terms of "neuron differentiation", "gastrula formation" and "embryonic morphogenesis", and many of the genes (692 genes) increased in d4 BLIMP1$^{-/-}$; BTAG positive cells had higher P values and similar GO terms. This indicates that BLIMP1 functions to suppress such development programs in hPGCLCs (FIG. 7C and FIG. 7D). In contrast, the number of genes suppressed in BLIMP1$^{-/-}$; BTAG positive cells was smaller (61 and 300 genes for d2 and d4, respectively), and many GO terms related to apoptosis and cell cycle. This suggests a misregulation of basic cellular properties in BLIMP1$^{-/-}$; BTAG positive cells (FIG. 7C and FIG. 7D).

the genes up- or down-regulated in BLIMP1$^{-/-}$; BTAG positive cells showed different expression patterns in hPGCLC induction and particularly, in BLIMP1$^{+/-}$; BTAG positive cells, intermediate gene expression pattern between wild-type and BLIMP1$^{-/-}$ cells was shown (FIG. 7E). The genes relating to "neuron differentiation" and "embryonic morphogenesis" and increased in d2 BLIMP1$^{-/-}$; BTAG positive cells expressed little or did not express in wild-type d2 PGCLCs (FIG. 7E). From these data, it was clearly shown that BLIMP1 controls the expression level of genes widely in a dose-dependent manner in hPGCLC induction.

Very many genes relating to "neuron differentiation" and the related GO terms were found in genes that increase in d2 and d4 BLIMP1$^{-/-}$; BTAG positive cells (FIG. 7D). Thus, the dynamics of gene expression of "neuronal differentiation" in wild-type hPGCLC induction and the effect of BLIMP1 deficiency in this expression were investigated. As shown in FIG. 7F, the genes of "neuron differentiation" are classified into several expression categories. The genes that increase in BLIMP1$^{-/-}$ cells were abundant in the expression categories relating to upregulation in d2 hPGCLCs (18/39, about 46%) and expression categories relating to downregulation (6/23, about 26%). 15 genes for "neuronal differentiation" whose expression does not change remarkably in wild-type hPGCLC induction increased in d2 or d4 BLIMP1$^{-/-}$ cells (FIG. 14E).

From the above results, it was suggested that the main function of BLIMP1 is to suppress the "neuronal differentiation" gene that increased in d2 hPGCLCs to a moderate level, and to appropriately suppress such genes that decrease in d2 hPGCLCs.

INDUSTRIAL APPLICABILITY

According to the differentiation induction method of the present invention, human pluripotent stem cells can be induced to differentiate into human PGC-like cells with high efficiency and good reproducibility. In addition, using the cell surface marker of the present invention, human PGC-like cells can be isolated and purified efficiently. Therefore, germ cell differentiation determination pathway from human pluripotent stem cells can be functionally reconstituted in vitro, and the present invention is markedly useful for elucidating the developmental mechanism of germ cells in human and for establishing diagnosis/treatment of diseases caused by defects in human germ cells.

The contents disclosed in any publication stated in the present specification, including patents, patent applications and scientific literatures, are hereby incorporated in their entireties by reference, to the extent that they have been disclosed herein.

This application is based on a patent application No. 2015-130501 filed in Japan (filing date: Jun. 29, 2015), the contents of which are incorporated in full herein.

The invention claimed is:

1. A method for producing a human primordial germ cell-like (PGC-like) cell from a human pluripotent stem cell, comprising the following steps I) and II):
   I) a step of producing a mesoderm-like cell by culturing a human pluripotent stem cell in a culture medium comprising activin A and a GSK3β inhibitor,
   II) a step of culturing the mesoderm-like cell obtained in step I) in a culture medium containing BMP.

2. The method according to claim 1 wherein the culture in said step I) is performed for less than 60 hr.

3. The method according to claim 2 wherein the culture in said step I) is performed for 42 hr.

4. The method according to claim 1 wherein said GSK3β inhibitor is CHIR99021.

5. The method according to claim 1 wherein the culture medium in said step I) further comprises a fibroblast growth factor receptor (FGFR) inhibitor.

6. The method according to claim 5 wherein said FGFR inhibitor is PD173074.

7. The method according to claim 1 wherein the culture medium in said step I) does not contain bFGF or BMP.

8. The method according to claim 1 wherein the culture medium in said step II) further comprises at least one cytokine selected from the group consisting of SCF, EGF and LIF.

9. The method according to claim 1 wherein said pluripotent stem cell is a pluripotent stem cell cultured under serum-free and feeder-free conditions.

10. The method according to claim 9 wherein the culturing under said feeder-free conditions is culturing on laminin511 or laminin511 fragment.

11. The method according to claim 1 further comprising III) a step of selecting a cell positive to at least one cell surface marker selected from the group consisting of PECAM (CD31), INTEGRINα6 (CD49f), INTEGRINβ3 (CD61), KIT (CD117), EpCAM, PODOPLANIN and TRA1-81 from the cells obtained in said step II).

12. The method according to claim 11 wherein said step III) is a step of selecting a double positive cell of INTEGRINα6 (CD49f) and EpCAM.

13. The method according to claim 1 wherein said human pluripotent stem cell is a human iPS cell.

14. A reagent kit for inducing differentiation of a human pluripotent stem cell into a human primordial germ cell-like (PGC-like) cell comprising the following (1) and (2):
   (1) a reagent for inducing a human pluripotent stem cell into a mesoderm-like cell comprising activin A and a GSK3β inhibitor,
   (2) a reagent for inducing a mesoderm-like cell into a human primordial germ cell-like (PGC-like) cell comprising BMP.

15. The kit according to claim 14 wherein said GSK3β inhibitor is CHIR99021.

16. The kit according to claim 14 wherein the induction reagent of said (1) further comprises a fibroblast growth factor receptor (FGFR) inhibitor.

17. The kit according to claim 16 wherein said FGFR inhibitor is PD173074.

18. The kit according to claim 14 wherein the induction reagent of said (2) further comprises at least one cytokine selected from the group consisting of SCF, EGF and LIF.

19. The kit according to claim 14 further comprising (3) a reagent for isolating a human primordial germ cell-like (PGC-like) cell comprising an antibody to at least one cell surface marker selected from the group consisting of PECAM (CD31), INTEGRINα6 (CD49f), INTEGRINβ3 (CD61), KIT (CD117), EpCAM, PODOPLANIN and TRA1-81.

20. The kit according to claim 19 wherein the isolation reagent of said (3) comprises an antibody to INTEGRINα6 (CD49f) and an antibody to EpCAM.

* * * * *